(12) United States Patent  (10) Patent No.: US 6,867,222 B2
Sun et al.  (45) Date of Patent: Mar. 15, 2005

(54) NOCICEPTIN ANALOGS

(75) Inventors: Qun Sun, Belle Mead, NJ (US); R. Richard Goehring, Pipersville, PA (US); Donald Kyle, Newtown, PA (US); Zhengming Chen, Belle Mead, NJ (US); Sam Victory, Newtown, PA (US); John Whitehead, Newtown, PA (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 10/126,471

(22) Filed: Apr. 18, 2002

(65) Prior Publication Data

US 2003/0069249 A1 Apr. 10, 2003

Related U.S. Application Data

(60) Provisional application No. 60/284,666, filed on Apr. 18, 2001, provisional application No. 60/284,667, filed on Apr. 18, 2001, provisional application No. 60/284,668, filed on Apr. 18, 2001, and provisional application No. 60/284,669, filed on Apr. 18, 2001.

(51) Int. Cl.⁷ ..................... A61K 31/495; C07D 401/04
(52) U.S. Cl. ...................................... 514/322; 546/199
(58) Field of Search ........................... 546/199; 514/322

(56) References Cited

U.S. PATENT DOCUMENTS

| | | | |
|---|---|---|---|
| 3,161,645 A | 12/1964 | Adriaan et al. | 260/293.4 |
| 3,318,900 A | 5/1967 | Adriaan et al. | 260/294 |
| 3,325,499 A | 6/1967 | Poos et al. | 260/294 |
| 4,215,119 A | 7/1980 | Mentrup et al. | 424/248.5 |
| 4,329,353 A | 5/1982 | Stokbroekx et al. | 424/267 |
| 4,410,528 A | 10/1983 | Teranishi et al. | 424/251 |
| 5,574,044 A | 11/1996 | Thompson et al. | 514/316 |
| 5,612,335 A | 3/1997 | Himmelsbach et al. | 514/221 |
| 5,661,169 A | 8/1997 | Di Malta et al. | 514/387 |
| 5,760,054 A | 6/1998 | Huff et al. | 514/302 |
| 5,767,118 A | 6/1998 | Nargund et al. | 514/226.4 |
| 6,063,796 A | 5/2000 | Yang et al. | 514/322 |
| 6,166,037 A | 12/2000 | Budhu et al. | 514/326 |
| 6,172,067 B1 | 1/2001 | Ito et al. | 514/252.13 |
| 6,204,265 B1 | 3/2001 | Reichard et al. | 514/235.8 |
| 6,225,052 B1 | 5/2001 | Batz et al. | 435/6 |
| 2002/0049212 A1 | 4/2002 | Ito et al. | 514/252.03 |
| 2003/0171360 A1 | 9/2003 | Gross et al. | 514/217.06 |

FOREIGN PATENT DOCUMENTS

EP        0092391 A2    10/1983    ......... C07D/401/06

(List continued on next page.)

OTHER PUBLICATIONS

Hiroyuki et al, Chemical Abstracts, vol. 99 No. 522375, "Syn. of bensimidazoles and dihydroquinazolines" (1983).*

(List continued on next page.)

Primary Examiner—Cecilia J. Tsang
Assistant Examiner—Raymond Covington
(74) Attorney, Agent, or Firm—Philip C. Strassburger; Alan L. Koller; Stephen J. Sand

(57) ABSTRACT

A compound of the formula (I), (II), (III) or (IV)

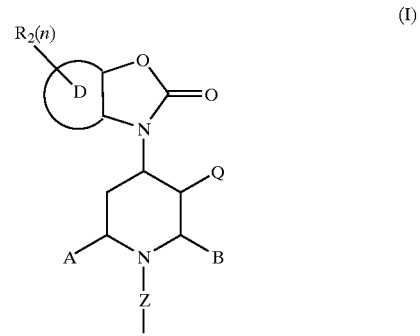

(I)

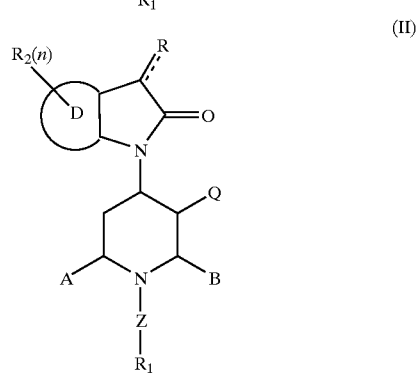

(II)

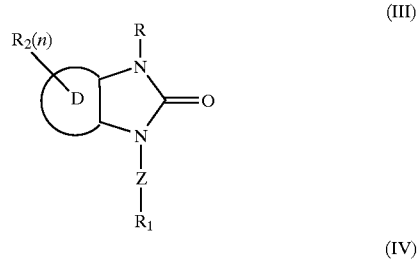

(III)

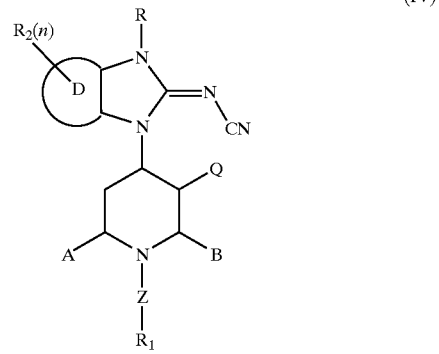

(IV)

wherein
Z, A, B, C, R, $R_1$, $R_2$, Q, and n are as described herein.

31 Claims, No Drawings

FOREIGN PATENT DOCUMENTS

| | | | | |
|---|---|---|---|---|
| EP | 0738726 | A1 | 4/1996 | ......... A61K/31/425 |
| EP | 0738726 | B1 | 4/1996 | ......... A61K/31/425 |
| EP | 0921125 | A1 | 6/1999 | ......... C07D/471/10 |
| EP | 1069124 | A1 | 7/2000 | .......... A61K/31/45 |
| EP | 1167969 | A2 | 5/2001 | ........... G06F/19/00 |
| JP | 60120872 | | 6/1985 | ......... C07D/237/34 |
| JP | 10330377 | | 12/1998 | ......... C07D/401/14 |
| WO | 9515961 | | 6/1995 | ......... C07D/401/04 |
| WO | 9710213 | A1 | 3/1997 | ......... C07D/211/44 |
| WO | 9740035 | A1 | 10/1997 | ......... C07D/401/04 |
| WO | 9740035 | | 10/1997 | ......... C07D/401/04 |
| WO | 9832439 | | 7/1998 | .......... A61K/31/41 |
| WO | 9854168 | A1 | 12/1998 | ......... C07D/401/04 |
| WO | 9932481 | | 1/1999 | ......... C07D/401/14 |
| WO | 9928313 | | 6/1999 | ......... C07D/401/02 |
| WO | 9929696 | A1 | 6/1999 | ....... C07D/491/107 |
| WO | 9936421 | A1 | 7/1999 | ......... C07D/401/04 |
| WO | 9937304 | | 7/1999 | ......... A61K/31/505 |
| WO | 9948492 | A1 | 9/1999 | ......... A61K/31/165 |
| WO | 9959997 | A1 | 11/1999 | ......... C07D/471/10 |
| WO | 0006545 | A1 | 2/2000 | ......... C07D/211/52 |
| WO | 0006545 | | 2/2000 | ......... C07D/211/52 |
| WO | 0013508 | | 3/2000 | .......... A01N/43/36 |
| WO | 0039114 | | 6/2000 | ......... C07D/401/00 |
| WO | 0078716 | A1 | 12/2000 | ......... C07D/209/16 |
| WO | 0107050 | A1 | 2/2001 | ......... A61K/31/445 |
| WO | 0144213 | A1 | 6/2001 | ......... C07D/265/18 |
| WO | 0192207 | A1 | 12/2001 | ......... C07C/231/02 |
| WO | 0220011 | A2 | 3/2002 | ......... A61K/31/347 |
| WO | 0285357 | A1 | 10/2002 | ........... A61K/31/44 |
| WO | 0288094 | A1 | 11/2002 | ......... C07D/235/30 |
| WO | 0335622 | A1 | 5/2003 | ......... C07D/209/52 |
| WO | 0337890 | A2 | 5/2003 | ......... C07D/401/04 |

OTHER PUBLICATIONS

Obase et al, Chemical Abstract, vol. 100 No. 68253, "Syn. od cyclic guanidines fused with aromatic ring throught metal ion promoted cyclization" (1983).*

Custers, F.G.J., et al., "Vesamicol and some of its derivatives: Questionable ligands for selectively labelling acetylcholine transporters in rat brain", European Journal of Pharmacology, 338: 117–183, 1997.

Harrison T, et al., "High Affinity, Selective Neurokinin 2 and Neurokinin 3 Receptor Antagonists from a Common Structural Template," Bioorganic & Medicinal Chemistry Letters., vol. 8, pp 1343–1348, especially compounds 2d and 3d on p. 1345. (1998).

Takai H, et al., Synthesis and Pharmacological Evaluation of Peperidine Derivatives with Various Heterocyclic Rings at the 4–Position, Chemical Pharmaceutical Bulletin, Mar. 1985, vol. 33, No. 3, pp. 1105–1115, especially pp. 1105 and 1106.

Database on STN Casdata (Columbus, Ohio, USA) CA accession: No. 129:54361, Huff, et al., 'Preparation of benzisothiazolones and analogs as alpha. 1C. adrenergic receptor antagonist', 1998, 392146 CAPLUS (Abstract).

Database on STN Casdata (Columbus, Ohio, USA) CA accession: No. 130:95479, Sasaki, et al., 'Preparation of piperidine derivatives as cell adhesion inhibitors for inflammation inhibitors, metastasis inhibitors, etc.', 1998, 795478 CAPLUS (Abstract).

Database on STN Cadata (Columbus, Ohio, USA) CA accession: No. 124:176079, Huff, et al., 'Preparation of heterocycles as alpha–1c adrenergic receptor antagonists', 1995, 998362 CAPLUS (Abstract).

Database on STN Casdata (Columbus, Ohio, USA) CA accession: No. 81:77786, Klein, et al., 'Potential analgesics. 3. 1–(4–Piperidinyl) –2–indolinones and –3, 4–dihydrocarbostyrils', Arch. Pharm. vol. 307 (5), pp 360–365. (1974), 1974, 47786 CAPLUS (Abstract).

Database on STN Casdata (Columbus, Ohio, USA) CA accession: No. 136:53656, Forbes I.T., 'A short and efficient syntheisis of N–substituted indol–2–ones (oxindoles)', Tetrahedron Let., (2001),vol. 42 (39), pp. 6943–6945, 2001:674545 CAPLUS (Abstract).

Database on STN Casdata (Columbus, Ohio, USA) CA accession: No. 135:195564, Tsushima, et al., 'Preparation of phenoxalkylamine derivatives useful as opioid delta receptor agonists', WO 2001/60796 (2001), 2001, 617978 CAPLUS (Abstract).

Database on STN Casdata (Columbus, Ohio, USA) CA accession: No. 135:272955, Tsushima, et al., 'Preparation of diphenylalkylpiperidine derivatives useful as opioid delta receptor agoinsts', 2001:713309 CAPLUS (Abstract).

Database on STN Casdata (Columbus, Ohio, USA) CA accession: No. 130:223167, Budhu, et al., 'Preparation of piperidinylpyrrolidins as modulators of chemokine receptor activity', 1999:172595 CAPLUS (Abstract).

Database on STN Casdata (Columbus, Ohio, USA) CA accession: No. 95:203828, Bianchi, et al., 'Compounds with antiulcer and antisecretory activity. I. 3–Aryl–benzimidazolin–2–ones and –thiones', Eur. J. Med. Chem, 16(4), pp. 321–326 (1981), 1981:203828 CAPLUS (Abstract).

Database on STN Casdata (Columbus, Ohio, USA) CA accession: No. 73:445405, Ogata, et al., 'Organic photochemical reactions. VII. Photolysis of 1–benzyl–2–ethylbenzimidazole 3–oxide', Chem. Pharm Bull, 18(5), pp. 964–969. (1970), 1970:445405 CAPLUS (Abstract).

Database on STN Casdata (Columbus, Ohio, USA) CA accession: No. 95:177993, Guiliano, et al., 'Spectroscopic studies of 2–oxo–2, 3–dihydrobenzimidazole and some N–monosubstituted o r N,N' –disubstituted derivatives', App. Spectrosc., (1981), 35(5), pp. 486–488, 1981:577993 CAPLUS (Abstract).

Database on STN Casdata (Columbus, Ohio, USA) CA accession: No. 134:353434, Nakamura, et al., 'Synthesis of a regio–isomer of kealiiquinone, a marine benzimidazole alkaloid', J. Chem. Soc. Japan, (2001), (4), pp. 429–436, 2001:112633 CAPLUS (Abstract).

Database on STN Casdata (Columbus, Ohio) CA accession: No. 125:58298, Suzuki, et al., 'Preparation of hetererocycle– containing amides as 5–HT4 agonists', PCT Int. Appl., p. 122 (WO 96/05166), 1996: 393911 CAPLUS (Abstract).

Obase, Hiroyuki, et al. "Synthesis of (1–Substituted Piperidin–4–yl)–1H–benzimidazoles and (1–Substituted Piperidein–4–yl)–3,4–dihydroquinazolines as Possible Antihypertensive Agents" Journal of Heterocyclic Chemistry; May–Jun. 1983 pp. 565–573.

Obase, Hiroyuki, et al. "Synthesis of Cyclic Guanidines Fused with Aromatic Ring through Metal Ion Promoted Cyclization" The Chemical Society of Japan, Oct. 1983, pp. 3189–3190.

* cited by examiner

NOCICEPTIN ANALOGS

This application claims priority from U.S. Provisional Application Ser. Nos. 60/284,666; 60/284,667; 60/284,668; 60/284,669 all filed Apr. 18, 2001, the disclosures of which are hereby incorporated by reference.

BACKGROUND OF THE INVENTION

Chronic pain is a major contributor to disability and is the cause of an untold amount of suffering. The successful treatment of severe and chronic pain is a primary goal of the physician with opioid analgesics being preferred drugs.

Until recently, there was evidence of three major classes of opioid receptors in the central nervous system (CNS), with each class having subtype receptors. These receptor classes were designated as $\mu$, $\delta$ and $\kappa$. As opiates had a high affinity to these receptors while not being endogenous to the body, research followed in order to identify and isolate the endogenous ligands to these receptors. These ligands were identified as enkephalins, endorphins and dynorphins.

Recent experimentation has led to the identification of a cDNA encoding an opioid receptor-like (ORL1) receptor with a high degree of homology to the known receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL1. This characteristic, along with the fact that an endogenous ligand had not yet been discovered, led to the term "orphan receptor".

Subsequent research led to the isolation and structure of the endogenous ligand of the ORL1 receptor. This ligand is a seventeen amino acid peptide structurally similar to members of the opioid peptide family.

The discovery of the ORL1 receptor presents an opportunity in drug discovery for novel compounds which can be administered for pain management or other syndromes modulated by this receptor.

All documents cited herein, including the foregoing, are incorporated by reference in their entireties for all purposes.

OBJECTS AND SUMMARY OF THE INVENTION

It is accordingly an object of certain embodiments of the present invention to provide new compounds which exhibit affinity for the ORL1 receptor, It is an object of certain embodiments of the present invention to provide new compounds which exhibit affinity for the ORL1 receptor and one or more of the $\mu$, $\delta$ or $\kappa$ receptors.

It is an object of certain embodiments of the present invention to provide new compounds for treating a patient suffering from chronic or acute pain by administering a compound having affinity for the ORL1 receptor.

It is an object of certain embodiments of the present invention to provide new compounds which have agonist activity at the $\mu$, $\delta$ and $\kappa$ receptors which is greater than compounds currently available e.g. morphine.

It is an object of certain embodiments of the present invention to provide methods of treating chronic and acute pain by administering compounds which have agonist activity at the $\mu$, $\delta$ and $\kappa$ receptors which is greater than compounds currently available.

It is an object of certain embodiments of the present invention to provide methods of treating chronic and acute pain by administering non-opioid compounds which have agonist activity at the $\mu$, $\delta$ and $\kappa$ receptors and which produce less side effects than compounds currently available.

It is an object of certain embodiments of the present invention to provide compounds useful as analgesics, anti-inflammatories, diuretics, anesthetics and neuroprotective agents, anti-hypertensives, anti-anxioltics; agents for appetite control; hearing regulators; anti-tussives, anti-asthmatics, modulators of locomotor activity, modulators of learning and memory, regulators of neurotransmitter and hormone release, kidney function modulators, anti-depressants, agents to treat memory loss due to Alzheimer's disease or other dementias, anti-epileptics, anti-convulsants, agents to treat withdrawal from alcohol and drugs of addiction, agents to control water balance, agents to control sodium excretion and agents to control arterial blood pressure disorders and methods for administering said compounds.

The compounds of the present invention are useful for modulating a pharmacodynamic response from one or more opioid receptors (ORL-1, $\mu$, $\delta$ and $\kappa$) centrally and/or peripherally. The response can be attributed to the compound stimulating (agonist) or inhibiting (antagonist) the one or more receptors. Certain compounds can stimulate one receptor (e.g., a $\mu$ agonist) and inhibit a different receptor (e.g., an ORL-1 antagonist).

Other objects and advantages of the present invention will become apparent from the following detailed description thereof. The present invention in certain embodiments comprises compounds having the general formula (I):

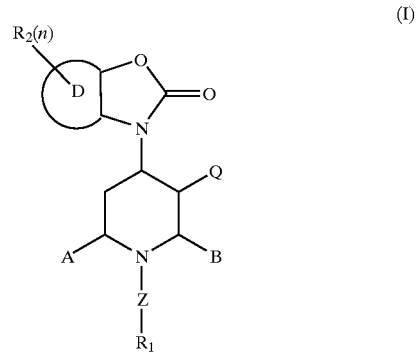

(I)

wherein

D is a 5–8 membered cycloalkyl, 5–8 membered heterocyclic or a 6 membered aromatic or heteroaromatic group;

n is an integer from 0 to 3;

A, B and Q are independently hydrogen, $C_{1-10}$ alkyl, $C_{3-12}$ cycloalkyl, $C_{1-10}$ alkoxy, $C_{3-12}$ cycloalkoxy, —$CH_2OH$, —$NHSO_2$, hydroxy$C_{1-10}$alkyl-, aminocarbonyl-, $C_{1-4}$alkylaminocarbonyl-, di$C_{1-4}$alkylaminocarbonyl-, acylamino-, acylaminoalkyl-, amide, sulfonylamino$C_{1-10}$ alkyl-, or A—B can together form a $C_{2-6}$ bridge, or B—Q can together form a $C_{3-7}$ bridge, or A—Q can together form a $C_{1-5}$ bridge;

Z is selected from the group consisting of a bond, straight or branched $C_{1-6}$ alkylene, —NH—, —$CH_2O$—, —$CH_2NH$—, —$CH_2N(CH_3)$—, —$NHCH_2$—, —$CH_2CONH$—, —$NHCH_2CO$—, —$CH_2CO$—, —$COCH_2$—, —$CH_2COCH_2$—, —$CH(CH_3)$—, —$CH$=, —O— and —HC=CH—, wherein the carbon and/or nitrogen atoms are unsubstituted or substituted with one or more lower alkyl, hydroxy, halo or alkoxy group;

$R_1$ is selected from the group consisting of hydrogen, $C_{1-10}$ alkyl, $C_{3-12}$cycloalkyl, $C_{2-10}$alkenyl, amino, $C_{1-10}$alkylamino-, $C_{3-12}$cycloalkylamino-, —COOV$_1$, —C$_{1-4}$ COOV$_1$, cyano, cyanoC$_{1-10}$alkyl-, cyanoC$_{3-10}$cycloalkyl-, NH$_2$SO$_2$—, NH$_2$SO$_2$C$_{1-4}$alkyl-, NH$_2$SOC$_{1-4}$alkyl-, aminocarbonyl-, C$_{1-4}$alkylaminocarbonyl-, diC$_{1-4}$alkylaminocarbonyl-, benzyl, C$_{3-12}$ cycloalkenyl-, a monocyclic, bicyclic or tricyclic aryl or heteroaryl ring, a hetero-monocyclic ring, a hetero-bicyclic ring system, and a spiro ring system of the formula (V):

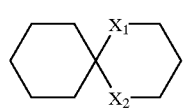

(V)

wherein $X_1$ and $X_2$ are independently selected from the group consisting of NH, O, S and CH$_2$; and wherein said alkyl, cycloalkyl, alkenyl, C$_{1-10}$alkylamino-, C$_{3-12}$cycloalkylamino-, or benzyl of $R_1$ is optionally substituted with 1–3 substituents selected from the group consisting of halogen, hydroxy, C$_{1-10}$ alkyl, C$_{1-10}$ alkoxy, nitro, trifluoromethyl-, cyano, —COOV$_1$, —C$_{1-4}$COOV$_1$, cyanoC$_{1-10}$alkyl-, —C$_{1-5}$(=O)W$_1$, —C$_{1-5}$NHS(=O)$_2$W$_1$, —C$_{1-5}$NHS(=O)W$_1$, a 5-membered heteroaromaticC$_{0-4}$ alkyl-, phenyl, benzyl, benzyloxy, said phenyl, benzyl, and benzyloxy optionally being substituted with 1–3 substituents selected from the group consisting of halogen, C$_{1-10}$ alkyl-, C$_{1-10}$ alkoxy-, and cyano; and wherein said C$_{3-12}$ cycloalkyl, C$_{3-12}$ cycloalkenyl, monocyclic, bicyclic or tricyclic aryl, heteroaryl ring, hetero-monocyclic ring, hetero-bicyclic ring system, or spiro ring system of the formula (V) is optionally substituted with 1–3 substituents selected from the group consisting of halogen, C$_{1-10}$ alkyl, C$_{1-10}$ alkoxy, nitro, trifluoromethyl-, phenyl, benzyl, phenyloxy and benzyloxy, wherein said phenyl, benzyl, phenyloxy or benzyloxy is optionally substituted with 1–3 substituents selected from the group consisting of halogen, C$_{1-10}$ alkyl, C$_{1-10}$ alkoxy, and cyano;

$W_1$ is hydrogen, $C_{1-10}$ alkyl, $C_{3-12}$ cycloalkyl, $C_{1-10}$ alkoxy, $C_{3-12}$ cycloalkoxy, —CH$_2$OH, amino, $C_{1-4}$alkylamino-, diC$_{1-4}$alkylamino-, or a 5-membered heteroaromatic ring optionally substituted with 1–3 lower alkyl;

$V_1$ is H, $C_{1-6}$ alkyl, $C_{3-6}$ cycloalkyl, benzyl or phenyl;

$R_2$ is selected from the group consisting of hydrogen, $C_{1-10}$ alkyl, $C_{3-12}$ cycloalkyl- and halogen, said alkyl or cycloalkyl optionally substituted with an oxo, amino, alkylamino or dialkylamino group;

and pharmaceutically acceptable salts thereof and solvates thereof.

The present invention in certain embodiments comprises compounds having the general formula (IA) as follows:

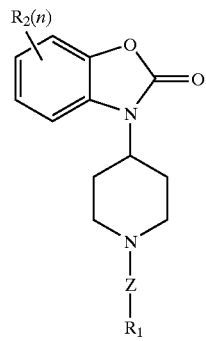

(IA)

wherein n is an integer from 0 to 3;

Z is selected from the group consisting of a bond, —CH$_2$—, —NH—, —CH$_2$O—, —CH$_2$CH$_2$—, —CH$_2$NH—, —CH$_2$N(CH$_3$)—, —NHCH$_2$—, —CH$_2$CONH—, —NHCH$_2$CO—, —CH$_2$CO—, —COCH$_2$—, —CH$_2$COCH$_2$—, —CH(CH$_3$)—, —CH=, and —HC=CH—, wherein the carbon and/or nitrogen atoms are unsubstituted or substituted with a lower alkyl, halogen, hydroxy or alkoxy group;

$R_1$ is selected from the group consisting of hydrogen, $C_{1-10}$alkyl, $C_{3-12}$cycloalkyl, $C_{2-10}$alkenyl, amino, $C_{1-10}$alkylamino, $C_{3-12}$cycloalkylamino, benzyl, $C_{3-12}$ cycloalkenyl, a monocyclic, bicyclic or tricyclic aryl or heteroaryl ring, a hetero-monocyclic ring, a hetero-bicyclic ring system, and a spiro ring system of the formula (V):

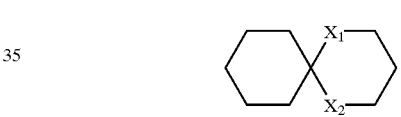

(V)

wherein $X_1$ and $X_2$ are independently selected from the group consisting of NH, O, S and CH$_2$;

wherein said monocyclic aryl is preferably phenyl;

wherein said bicyclic aryl is preferably naphthyl;

wherein said alkyl, cycloalkyl, alkenyl, C$_{1-10}$alkylamino, C$_{3-12}$cycloalkylamino, or benzyl is optionally substituted with 1–3 substituents selected from the group consisting of halogen, C$_{1-10}$ alkyl C$_{1-10}$ alkoxy, nitro, trifluoromethyl, cyano, phenyl, benzyl, benzyloxy, said phenyl, benzyl, and benzyloxy optionally being substituted with 1–3 substituents selected from the group consisting of halogen, C$_{1-10}$ alkyl, C$_{1-10}$ alkoxy, and cyano;

wherein said $C_{3-12}$ cycloalkyl, $C_{3-12}$ cycloalkenyl, monocyclic, bicyclic or tricyclic aryl, heteroaryl ring, hetero-monocyclic ring, hetero-bicyclic ring system, and spiro ring system of the formula (V) are optionally substituted with 1–3 substituents selected from the group consisting of halogen, C$_{1-10}$ alkyl, C$_{1-10}$ alkoxy, nitro, trifluoromethyl, phenyl, benzyl, phenyloxy and benzyloxy, wherein said phenyl, benzyl, phenyloxy and benzyloxy are optionally substituted with 1–3 substituents selected from the group consisting of halogen, C$_{1-10}$ alkyl, C$_{1-10}$ alkoxy, and cyano;

$R_2$ is selected from the group consisting of hydrogen, $C_{1-10}$ alkyl $C_{3-12}$ cycloalkyl and halogen, said alkyl optionally substituted with an oxo group;

and pharmaceutically acceptable salts thereof and solvates thereof.

In certain preferred embodiments of formula (I), D is phenyl or a 6 membered heteroaromatic group containing 1–3 nitrogen atoms.

In certain preferred embodiments of formula (I) or (IA), the $R_1$ alkyl is methyl, ethyl, propyl, butyl, pentyl, or hexyl.

In certain preferred embodiments of formula (I) or (IA), the $R_1$ cycloalkyl is cyclohexyl, cycloheptyl, cyclooctyl, cyclononyl, cyclodecyl, or norbornyl.

In other preferred embodiments of formula (I) or (IA), the $R_1$ bicyclic ring system is naphthyl. In other preferred embodiments of formula (I) or (IA), the $R_1$ bicyclic ring system is tetrahydronaphthyl, or decahydronaphthyl and the $R_1$ tricyclic ring system is dibenzocycloheptyl. In other preferred embodiments $R_1$ is phenyl or benzyl.

In other preferred embodiments of formula (I) or (IA), the $R_1$ bicyclic aromatic ring is a 10-membered ring, preferably quinoline or naphthyl.

In other preferred embodiments of formula (I) or (IA), the $R_1$ bicyclic aromatic ring is a 9-membered ring, preferably indenyl.

In certain embodiments of formula (I) or (IA), Z is a bond, methyl, or ethyl.

In certain embodiments of formula (I) or (IA), the Z group is maximally substituted as not to have any hydrogen substitution on the base Z group. For example, if the base Z group is —$CH_2$—, substitution with two methyl groups would remove hydrogens from the —$CH_2$— base Z group.

In other preferred embodiments of formula (I) or (IA), n is 0.

In certain embodiments of formula (I) or (IA), $X_1$ and $X_2$ are both 0.

In certain embodiments of formula (I), $ZR_1$ is cyclohexylethyl-, cyclohexylmethyl-, cyclopentylmethyl-, dimethylcyclohexylmethyl-, phenylethyl-, pyrrolyltrifluoroethyl-, thienyltrifluoroethyl-, pyridylethyl-, cyclopentyl-, cyclohexyl-, methoxycyclohexyl-, tetrahydropyranyl-, propylpiperidinyl-, indolylmethyl-, pyrazoylpentyl-, thiazolylethyl-, phenyltrifluoroethyl-, hydroxyhexyl-, methoxyhexyl-, isopropoxybutyl-, hexyl-, or oxocanylpropyl-.

In certain embodiments of formula (I), $ZR_1$ is —$CH_2COOV_1$, tetrazolylmethyl-, cyanomethyl-, $NH_2SO_2$methyl-, $NH_2SO$methyl-, aminocarbonylmethyl-, $C_{1-4}$alkylaminocarbonylmethyl-, or di$C_{1-4}$alkylaminocarbonylmethyl-.

In certain embodiments of formula (I), $ZR_1$ is 3,3 diphenylpropyl optionally substituted at the 3 carbon of the propyl with —$COOV_1$, tetrazolyl$C_{0-4}$alkyl-, cyano-, aminocarbonyl-, $C_{1-4}$alkylaminocarbonyl-, or di$C_{1-4}$alkylaminocarbonyl-.

The present invention in certain embodiments comprises compounds having the general formula (II):

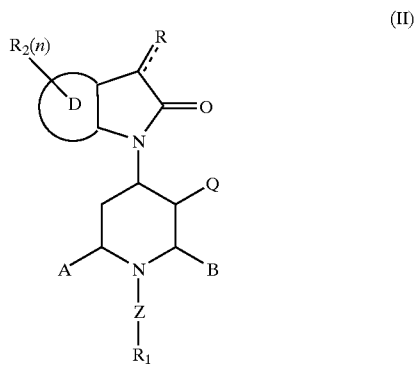

(II)

wherein
the dotted line represents an optional double bond;
R is hydrogen, $C_{1-10}$ alkyl, $C_{3-12}$ cycloalkyl, $C_{3-12}$ cycloalkyl$C_{1-4}$alkyl-, $C_{1-10}$ alkoxy, $C_{3-12}$ cycloalkoxy-, $C_{1-10}$ alkenyl, $C_{1-10}$ alkylidene, oxo, $C_{1-10}$ alkyl substituted with 1–3 halogen, $C_{3-12}$ cycloalkyl substituted with 1–3 halogen, $C_{3-12}$ cycloalkyl$C_{1-4}$alkyl-substituted with 1–3 halogen, $C_{1-10}$ alkoxy substituted with 1–3 halogen, $C_{3-12}$ cycloalkoxy-substituted with 1–3 halogen, —$COOV_1$, —$C_{1-4}COOV_1$, —$CH_2OH$, —$SO_2N(V_1)_2$, hydroxy$C_{1-10}$ alkyl-, hydroxy$C_{3-10}$cycloalkyl-, cyano$C_{1-10}$alkyl-, cyano$C_{3-10}$cycloalkyl-, —$CON(V_1)_2$, $NH_2SO_2C_{1-4}$alkyl-, $NH_2SOC_{1-4}$alkyl-, sulfonylamino$C_{1-10}$alkyl-, diaminoalkyl-, -sulfonyl$C_{1-4}$alkyl, a 6-membered heterocyclic ring, a 6-membered heteroaromatic ring, a 6-membered heterocyclic$C_{1-4}$alkyl-, a 6-membered heteroaromatic$C_{1-4}$alkyl-, a 6-membered aromatic ring, a 6-membered aromatic$C_{1-4}$ alkyl-, a 5-membered heterocyclic ring optionally substituted with an oxo or thio, a 5-membered heteroaromatic ring, a 5-membered heterocyclic$C_{1-4}$alkyl-optionally substituted with an oxo or thio, a 5-membered heteroaromatic$C_{1-4}$alkyl-, —$C_{1-5}(=O)W_1$, —$C_{1-5}(=NH)W_1$, —$C_{1-5}NHC(=O)W_1$, —$C_{1-5}NHS(=O)_2W_1$, —$C_{1-5}NHS(=O)W_1$, wherein $W_1$ is hydrogen, $C_{1-10}$ alkyl, $C_{3-12}$ cycloalkyl, $C_{1-10}$ alkoxy, $C_{3-12}$ cycloalkoxy, —$CH_2OH$, amino, $C_{1-4}$alkylamino-, di$C_{1-4}$alkylamino-, or a 5-membered heteroaromatic ring optionally substituted with 1–3 lower alkyl;
wherein each $V_1$ is independently selected from H, $C_{1-6}$ alkyl, $C_{3-6}$ cycloalkyl, benzyl and phenyl;
n is an integer from 0 to 3;
D is a 5–8 membered cycloalkyl, 5–8 membered heterocyclic or a 6 membered aromatic or heteroaromatic group;
n is an integer from 0 to 3;
A, B and Q are independently hydrogen, $C_{1-10}$ alkyl, $C_{3-12}$ cycloalkyl, $C_{1-10}$ alkoxy, $C_{3-12}$ cycloalkoxy, $C_{1-10}$ alkenyl, $C_{1-10}$ alkylidene, oxo, —$CH_2OH$, —$NHSO_2$, hydroxy$C_{1-10}$ alkyl-, aminocarbonyl-, $C_{1-4}$alkylaminocarbonyl-, di$C_{1-4}$ alkylaminocarbonyl-, acylamino-, acylaminoalkyl-, amide, sulfonylamino$C_{1-10}$alkyl-, or A—B can together form a $C_{2-6}$ bridge, or B—Q can together form a $C_{3-7}$ bridge, or A—Q can together form a $C_{1-5}$ bridge;
Z is selected from the group consisting of a bond, straight or branched $C_{1-6}$ alkylene, —NH—, —$CH_2O$—, —$CH_2NH$—, —$CH_2N(CH_3)$—, —$NHCH_2$—, —$CH_2CONH$—, —$NHCH_2CO$—, —$CH_2CO$—, —$COCH_2$—, —$CH_2COCH_2$—, —$CH(CH_3)$—, —CH=, —O— and —HC=CH—, wherein the carbon and/or nitrogen atoms are unsubstituted or substituted with one or more lower alkyl, hydroxy, halo or alkoxy group;

$R_1$ is selected from the group consisting of hydrogen, $C_{1-10}$ alkyl, $C_{3-12}$cycloalkyl, $C_{2-10}$alkenyl, amino, $C_{1-10}$alkylamino-, $C_{3-12}$cycloalkylamino-, —COOV$_1$, —$C_{1-4}$ COOV$_1$, cyano, cyano$C_{1-10}$alkyl-, cyano$C_{3-10}$cycloalkyl-, NH$_2$SO$_2$—, NH$_2$SO$_2$C$_{1-4}$alkyl-, NH$_2$SOC$_{1-4}$alkyl-, aminocarbonyl-, $C_{1-4}$alkylaminocarbonyl-, diC$_{1-4}$ alkylaminocarbonyl-, benzyl, $C_{3-12}$ cycloalkenyl-, a monocyclic, bicyclic or tricyclic aryl or heteroaryl ring, a hetero-monocyclic ring, a hetero-bicyclic ring system, and a spiro ring system of the formula (V):

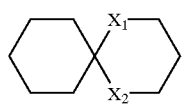
(V)

wherein $X_1$ and $X_2$ are independently selected from the group consisting of NH, O, S and CH$_2$; and wherein said alkyl, cycloalkyl, alkenyl, $C_{1-10}$alkylamino-, $C_{3-12}$cycloalkylamino-, or benzyl of $R_1$ is optionally substituted with 1–3 substituents selected from the group consisting of halogen, hydroxy, $C_{1-10}$ alkyl, $C_{1-10}$ alkoxy, nitro, trifluoromethyl-, cyano, —COOV$_1$, —C$_{1-4}$COOV$_1$, cyanoC$_{1-10}$alkyl-, —C$_{1-5}$(=O)W$_1$, —C$_{1-5}$NHS(=O)$_2$W$_1$, —C$_{1-5}$NHS(=O)W$_1$, a 5-membered heteroaromaticC$_{0-4}$ alkyl-, phenyl, benzyl, benzyloxy, said phenyl, benzyl, and benzyloxy optionally being substituted with 1–3 substituents selected from the group consisting of halogen, $C_{1-10}$ alkyl $C_{1-10}$ alkoxy-, and cyano; and wherein said $C_{3-12}$ cycloalkyl, $C_{3-12}$ cycloalkenyl, monocyclic, bicyclic or tricyclic aryl, heteroaryl ring, hetero-monocyclic ring, hetero-bicyclic ring system, or spiro ring system of the formula (V) is optionally substituted with 1–3 substituents selected from the group consisting of halogen, $C_{1-10}$ alkyl, $C_{1-10}$ alkoxy, nitro, trifluoromethyl-, phenyl, benzyl, phenyloxy and benzyloxy, wherein said phenyl, benzyl, phenyloxy or benzyloxy is optionally substituted with 1–3 substituents selected from the group consisting of halogen, $C_{1-10}$ alkyl, $C_{1-10}$ alkoxy, and cyano;

$R_2$ is selected from the group consisting of hydrogen, $C_{1-10}$ alkyl $C_{3-12}$ cycloalkyl- and halogen, said alkyl or cycloalkyl optionally substituted with an oxo, amino, alkylamino or dialkylamino group;

and pharmaceutically acceptable salts thereof and solvates thereof.

The present invention in certain embodiments comprises compounds having the formula (IIA):

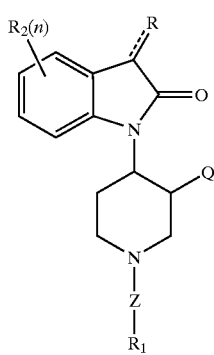
(IIA)

wherein
the dotted line represents an optional double bond;
Z is selected from the group consisting of a bond, —CH$_2$—, —NH—, —CH$_2$O—, —CH$_2$CH$_2$—, —CH$_2$NH—, —CH$_2$N(CH$_3$)—, —NHCH$_2$—, —CH$_2$CONH—, —NHCH$_2$CO—, —CH$_2$CO—, —COCH$_2$—, —CH$_2$COCH$_2$—, —CH(CH$_3$)—, —CH=, and —HC=CH—, wherein the carbon and/or nitrogen atoms are unsubstituted or substituted with a lower alkyl, halogen, hydroxy or alkoxy group;

R and Q are the same or different and are each selected from the group consisting of hydrogen, halogen, $C_{1-10}$ alkyl, $C_{1-10}$ alkenyl, $C_{1-10}$ alkylidene, $C_{3-12}$ cycloalkyl, $C_{1-10}$ alkoxy, and oxo;

$R_1$ is selected from the group consisting of hydrogen, $C_{1-10}$alkyl, $C_{3-12}$cycloalkyl, $C_{2-10}$alkenyl, amino, $C_{1-10}$alkylamino, $C_{3-12}$cycloalkylamino, benzyl, $C_{3-12}$ cycloalkenyl, a monocyclic, bicyclic or tricyclic aryl or heteroaryl ring, a heteromonocyclic ring, a bicyclic ring system, and a spiro ring system of the formula (V):

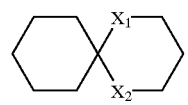
(V)

wherein $X_1$ and $X_2$ are independently selected from the group consisting of NH, O, S and CH$_2$;
wherein said monocyclic aryl is preferably phenyl;
wherein said bicyclic aryl is preferably naphthyl;
wherein said alkyl, cycloalkyl, alkenyl, $C_{1-10}$alkylamino, $C_{3-12}$cycloalkylamino, or benzyl is optionally substituted with 1–3 substituents selected from the group consisting of halogen, $C_{1-10}$ alkyl, $C_{1-10}$ alkoxy, nitro, trifluoromethyl, cyano, phenyl, benzyl, benzyloxy, said phenyl, benzyl, and benzyloxy optionally being substituted with 1–3 substituents selected from the group consisting of halogen, $C_{1-10}$ alkyl, $C_{1-10}$ alkoxy, and cyano;

wherein said $C_{3-12}$ cycloalkyl, $C_{3-12}$ cycloalkenyl, monocyclic, bicyclic or tricyclic aryl, heteroaryl ring, heteromonocyclic ring, heterobicyclic ring system, and spiro ring system of the formula (V) are optionally substituted with 1–3 substituents selected from the group consisting of halogen, $C_{1-10}$ alkyl, $C_{1-10}$ alkoxy, nitro, trifluoromethyl, phenyl, benzyl, phenyloxy and benzyloxy, wherein said phenyl, benzyl, phenyloxy and benzyloxy are optionally substituted with 1–3 substituents selected from the group consisting of halogen, $C_{1-10}$ alkyl, $C_{1-10}$ alkoxy, and cyano;

$R_2$ is selected from the group consisting of hydrogen, $C_{1-10}$ alkyl, $C_{3-12}$ cycloalkyl and halogen, said alkyl optionally substituted with an oxo group;

and pharmaceutically acceptable salts thereof.

In certain preferred embodiments Q of formula (II) or (IIA), is hydrogen or methyl.

In certain preferred embodiments, R of formula (II) or (IIA), is hydrogen, methyl, ethyl, or ethylidene.

In certain preferred embodiments of formula (II), D is phenyl or a 6 membered heteroaromatic group containing 1–3 nitrogen atoms.

In certain preferred embodiments of formula (II) or (IIA), the $R_1$ alkyl is methyl, ethyl, propyl, butyl, pentyl, or hexyl.

In certain preferred embodiments of formula (II) or (IIA), the $R_1$ cycloalkyl is cyclohexyl, cycloheptyl, cyclooctyl, cyclononyl, cyclodecyl, or norbornyl.

In other preferred embodiments of formula (II) or (IIA), the R₁ bicyclic ring system is naphthyl. In other preferred embodiments of formula (II) or (IIA), the R₁ bicyclic ring system is tetrahydronaphthyl, or decahydronaphthyl and the R₁ tricyclic ring system is dibenzocycloheptyl. In other preferred embodiments R₁ is phenyl or benzyl.

In other preferred embodiments of formula (II) or (IIA), the R₁ bicyclic aromatic ring is a 10-membered ring, preferably quinoline or naphthyl.

In other preferred embodiments of formula (II) or (IIA), the R₁ bicyclic aromatic ring is a 9-membered ring, preferably indenyl.

In certain embodiments of formula (II) or (IIA), Z is a bond, methyl, or ethyl.

In certain embodiments of formula (II) or (IIA), the Z group is maximally substituted as not to have any hydrogen substitution on the base Z group. For example, if the base Z group is —CH₂—, substitution with two methyl groups would remove hydrogens from the —CH₂— base Z group.

In other preferred embodiments of formula (II) or (IIA), n is 0.

In certain embodiments of formula (II) or (IIA), X₁ and X₂ are both 0.

In other preferred embodiments, the dotted line is a double bond.

In certain embodiments of formula (II), R is —CH₂C(=O)NH₂, —C(NH)NH₂, pyridylmethyl, cyclopentyl, cyclohexyl, furanylmethyl, —C(=O)CH₃, —CH₂CH₂NHC(=O)CH₃, —SO₂CH₃, CH₂CH₂NHSO₂CH₃, furanylcarbonyl-, methylpyrrolylcarbonyl-, diazolecarbonyl-, azolemethyl-, trifluoroethyl-, hydroxyethyl-, cyanomethyl-, oxo-oxazolemethyl-, or diazolemethyl-.

In certain embodiments of formula (II), ZR₁ is cyclohexylethyl-, cyclohexylmethyl-, cyclopentylmethyl-, dimethylcyclohexylmethyl-, phenylethyl-, pyrrolyltrifluoroethyl-, thienyltrifluoroethyl-, pyridylethyl-, cyclopentyl-, cyclohexyl-, methoxycyclohexyl-, tetrahydropyranyl-, propylpiperidinyl-, indolylmethyl-, pyrazoylpentyl-, thiazolylethyl-, phenyltrifluoroethyl-, hydroxyhexyl-, methoxyhexyl-, isopropoxybutyl-, hexyl-, or oxocanylpropyl-.

In certain embodiments of formula (II), at least one of ZR₁ or R is —CH₂COOV₁, tetrazolylmethyl-, cyanomethyl-, NH₂SO₂methyl-, NH₂SOmethyl-, aminocarbonylmethyl-, C₁₋₄alkylaminocarbonylmethyl-, or diC₁₋₄alkylaminocarbonylmethyl-.

In certain embodiments of formula (II), ZR₁ is 3,3 diphenylpropyl optionally substituted at the 3 carbon of the propyl with —COOV₁, tetrazolylC₀₋₄alkyl-, cyano-, aminocarbonyl-, C₁₋₄alkylaminocarbonyl-, or diC₁₋₄alkylaminocarbonyl-.

The present invention in certain embodiments comprises compounds having the general formula (III):

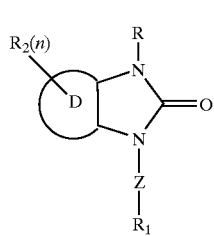

(III)

wherein R is hydrogen, C₁₋₁₀ alkyl, C₃₋₁₂ cycloalkyl, C₃₋₁₂ cycloalkylC₁₋₄alkyl-, C₁₋₁₀ alkoxy, C₃₋₁₂ cycloalkoxy-, C₁₋₁₀ alkyl substituted with 1–3 halogen, C₃₋₁₂ cycloalkyl substituted with 1–3 halogen, C₃₋₁₂ cycloalkylC₁₋₄alkyl-substituted with 1–3 halogen, C₁₋₁₀ alkoxy substituted with 1–3 halogen, C₃₋₁₂ cycloalkoxy-substituted with 1–3 halogen, —COOV₁, —C₁₋₄COOV₁, —CH₂OH, —SO₂N(V₁)₂, hydroxyC₁₋₁₀alkyl-, hydroxyC₃₋₁₀ cycloalkyl-, cyanoC₁₋₁₀alkyl-, cyanoC₃₋₁₀cycloalkyl-, —CON(V₁)₂, NH₂SO₂C₁₋₄alkyl-, NH₂SOC₁₋₄alkyl-, sulfonylaminoC₁₋₁₀alkyl-, diaminoalkyl-, -sulfonylC₁₋₄alkyl, a 6-membered heterocyclic ring, a 6-membered heteroaromatic ring, a 6-membered heterocyclicC₁₋₄alkyl-, a 6-membered heteroaromaticC₁₋₄alkyl-, a 6-membered aromatic ring, a 6-membered aromaticC₁₋₄ alkyl-, a 5-membered heterocyclic ring optionally substituted with an oxo or thio, a 5-membered heteroaromatic ring, a 5-membered heterocyclicC₁₋₄alkyl-optionally substituted with an oxo or thio, a 5-membered heteroaromaticC₁₋₄ alkyl-, —C₁₋₅(=O)W₁, —C₁₋₅(=NH)W₁, —C₁₋₅NHC(=O)W₁, —C₁₋₅NHS(=O)₂W₁, —C₁₋₅NHS(=O)W₁, wherein W₁ is hydrogen, C₁₋₁₀ alkyl, C₃₋₁₂ cycloalkyl, C₁₋₁₀ alkoxy, C₃₋₁₂ cycloalkoxy, —CH₂OH, amino, C₁₋₄alkylamino-, diC₁₋₄alkylamino-, or a 5-membered heteroaromatic ring optionally substituted with 1–3 lower alkyl;

wherein each V₁ is independently selected from H, C₁₋₆ alkyl, C₃₋₆ cycloalkyl, benzyl and phenyl;

n is an integer from 0 to 3;

D is a 5–8 membered cycloalkyl, 5–8 membered heterocyclic or a 6 membered aromatic or heteroaromatic group;

Z is selected from the group consisting of a bond, straight or branched C₁₋₆ alkylene, —NH—, —CH₂O—, —CH₂NH—, —CH₂N(CH₃)—, —NHCH₂—, —CH₂CONH—, —NHCH₂CO—, —CH₂CO—, —COCH₂—, —CH₂COCH₂—, —CH(CH₃)—, —CH=, —O— and —HC=CH—, wherein the carbon and/or nitrogen atoms are unsubstituted or substituted with one or more lower alkyl, hydroxy, halo or alkoxy group; or Z is a cycloalkylamino system of the formula (VI):

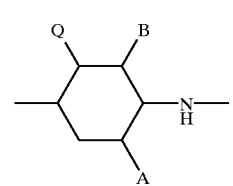

(VI)

wherein A, B and Q are independently hydrogen, C₁₋₁₀ alkyl, C₃₋₁₂ cycloalkyl, C₁₋₁₀ alkoxy, C₃₋₁₂ cycloalkoxy, —CH₂OH, —NHSO₂, hydroxyC₁₋₁₀alkyl-, aminocarbonyl-, C₁₋₄alkylaminocarbonyl-, diC₁₋₄alkylaminocarbonyl-, acylamino-, acylaminoalkyl-, amide, sulfonylaminoC₁₋₁₀alkyl-, or A—B can together form a C₂₋₆ bridge, or B—Q can together form a $C_{3-7}$ bridge, or A—Q can together form a $C_{1-5}$ bridge;

$R_1$ is selected from the group consisting of hydrogen, $C_{1-10}$ alkyl, $C_{3-12}$cycloalkyl, $C_{2-10}$alkenyl, amino, $C_{1-10}$alkylamino-, $C_{3-12}$cycloalkylamino-, —COOV$_1$, —$C_{1-4}$ COOV$_1$, cyano, cyanoC$_{1-10}$alkyl-, cyanoC$_{3-10}$cycloalkyl-, NH$_2$SO$_2$—, NH$_2$SO$_2$C$_{1-4}$alkyl-, NH$_2$SOC$_{1-4}$alkyl-, aminocarbonyl-, C$_{1-4}$alkylaminocarbonyl-, diC$_{1-4}$alkylaminocarbonyl-, benzyl, C$_{3-12}$ cycloalkenyl-, a monocyclic, bicyclic or tricyclic aryl or heteroaryl ring, a hetero-monocyclic ring, a hetero-bicyclic ring system, and a Spiro ring system of the formula (V):

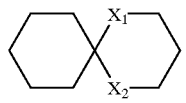

(V)

wherein $X_1$ and $X_2$ are independently selected from the group consisting of NH, O, S and CH$_2$; and wherein said alkyl, cycloalkyl, alkenyl, C$_{1-10}$alkylamino-, C$_{3-12}$cycloalkylamino-, or benzyl of R$_1$ is optionally substituted with 1–3 substituents selected from the group consisting of halogen, hydroxy, C$_{1-10}$ alkyl, C$_{1-10}$ alkoxy, nitro, trifluoromethyl-, cyano, —COOV$_1$, —C$_{1-4}$COOV$_1$, cyanoC$_{1-10}$alkyl-, —C$_{1-5}$(=O)W$_1$, —C$_{1-5}$NHS(=O)$_2$W$_1$, —C$_{1-5}$NHS(=O)W$_1$, a 5-membered heteroaromaticC$_{0-4}$alkyl-, phenyl, benzyl, benzyloxy, said phenyl, benzyl, and benzyloxy optionally being substituted with 1–3 substituents selected from the group consisting of halogen, C$_{1-10}$ alkyl-, C$_{1-10}$ alkoxy-, and cyano; and wherein said C$_{3-12}$ cycloalkyl, C$_{3-12}$ cycloalkenyl, monocyclic, bicyclic or tricyclic aryl, heteroaryl ring, hetero-monocyclic ring, hetero-bicyclic ring system, or spiro ring system of the formula (V) is optionally substituted with 1–3 substituents selected from the group consisting of halogen, C$_{1-10}$ alkyl, C$_{1-10}$ alkoxy, nitro, trifluoromethyl-, phenyl, benzyl, phenyloxy and benzyloxy, wherein said phenyl, benzyl, phenyloxy or benzyloxy is optionally substituted with 1–3 substituents selected from the group consisting of halogen, C$_{1-10}$ alkyl, C$_{1-10}$ alkoxy, and cyano;

$R_2$ is selected from the group consisting of hydrogen, $C_{1-10}$ alkyl, $C_{3-12}$ cycloalkyl- and halogen, said alkyl or cycloalkyl optionally substituted with an oxo, amino, alkylamino or dialkylamino group;

and pharmaceutically acceptable salts thereof and solvates thereof.

The present invention in certain embodiments comprises compounds having the formula (IIIA):

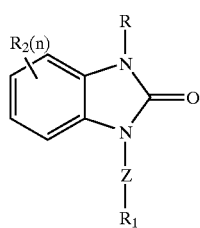

(IIIA)

wherein n is an integer from 0 to 3;

Z is selected from the group consisting of a bond, —CH$_2$—, —NH—, —CH$_2$O—, —CH$_2$CH$_2$—, —CH$_2$NH—, —CH$_2$N(CH$_3$)—, —NHCH$_2$—, —CH$_2$CONH—, —NHCH$_2$CO—, —CH$_2$CO—, —COCH$_2$—, —CH$_2$COCH$_2$—, —CH(CH$_3$)—, —CH=, —HC=CH—, and a cycloalkylamino system of the formula (VI):

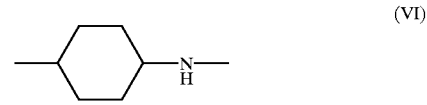

(VI)

wherein the carbon and/or nitrogen atoms are unsubstituted or substituted with a lower alkyl, halogen, hydroxy, phenyl, benzyl, or alkoxy group;

R is selected from the group consisting of hydrogen, C$_{1-10}$ alkyl, C$_{1-10}$ alkoxy, and C$_{3-12}$cycloalkyl;

$R_1$ is selected from the group consisting of hydrogen, C$_{1-10}$alkyl, C$_{3-12}$cycloalkyl, C$_{2-10}$alkenyl, amino, C$_{1-10}$alkylamino, C$_{3-12}$cycloalkylamino, benzyl, C$_{3-12}$ cycloalkenyl, a monocyclic, bicyclic or tricyclic aryl or heteroaryl ring, a heteromonocyclic ring, a heterobicyclic ring system, and a spiro ring system of the formula (V):

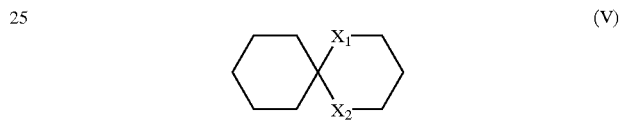

(V)

wherein $X_1$ and $X_2$ are independently selected from the group consisting of NH, O, S and CH$_2$;

wherein said monocyclic aryl is preferably phenyl;

wherein said bicyclic aryl is preferably naphthyl;

wherein said alkyl, cycloalkyl, alkenyl, C$_{1-10}$alkylamino, C$_{3-12}$cycloalkylamino, or benzyl is optionally substituted with 1–3 substituents selected from the group consisting of halogen, C$_{1-10}$ alkyl, C$_{1-10}$ alkoxy, nitro, trifluoromethyl, cyano, phenyl, benzyl, benzyloxy, said phenyl, benzyl, and benzyloxy optionally being substituted with 1–3 substituents selected from the group consisting of halogen, C$_{1-10}$ alkyl, C$_{1-10}$ alkoxy, and cyano;

wherein said C$_{3-12}$ cycloalkyl, C$_{3-12}$ cycloalkenyl, monocyclic, bicyclic or tricyclic aryl, heteroaryl ring, heteromonocyclic ring, heterobicyclic ring system, and spiro ring system of the formula (V) are optionally substituted with 1–3 substituents selected from the group consisting of halogen, C$_{1-10}$ alkyl, C$_{1-10}$ alkoxy, nitro, trifluoromethyl, phenyl, benzyl, phenyloxy and benzyloxy, wherein said phenyl, benzyl, phenyloxy and benzyloxy are optionally substituted with 1–3 substituents selected from the group consisting of halogen, C$_{1-10}$ alkyl, C$_{1-10}$ alkoxy, and cyano;

$R_2$ is selected from the group consisting of hydrogen, C$_{1-10}$ alkyl, C$_{3-12}$ cycloalkyl and halogen, said alkyl optionally substituted with an oxo group;

and pharmaceutically acceptable salts thereof.

In certain preferred embodiments of formula (III), D is phenyl or a 6 membered heteroaromatic group containing 1–3 nitrogen atoms.

In certain preferred embodiments of formula (III) or (IIIA), the R$_1$ alkyl is methyl, ethyl, propyl, butyl, pentyl, or hexyl.

In certain preferred embodiments of formula (III) or (IIIA), the R$_1$ cycloalkyl is cyclohexyl, cycloheptyl, cyclooctyl, cyclononyl, cyclodecyl, or norbornyl.

In other preferred embodiments of formula (III) or (IIIA), the $R_1$ bicyclic ring system is naphthyl. In other preferred embodiments of formula (III) or (IIIA), the $R_1$ bicyclic ring system is tetrahydronaphthyl, or decahydronaphthyl and the $R_1$ tricyclic ring system is dibenzocycloheptyl. In other preferred embodiments $R_1$ is phenyl or benzyl.

In other preferred embodiments of formula (III) or (IIIA), the $R_1$ bicyclic aromatic ring is a 10-membered ring, preferably quinoline or naphthyl.

In other preferred embodiments of formula (111) or (IIIA), the $R_1$ bicyclic aromatic ring is a 9-membered ring, preferably indenyl.

In certain embodiments of formula (III) or (IIIA), Z is a bond, methyl, or ethyl.

In certain embodiments of formula (III) or (IIIA), the Z group is maximally substituted as not to have any hydrogen substitution on the base Z group. For example, if the base Z group is —CH$_2$—, substitution with two methyl groups would remove hydrogens from the —CH$_2$— base Z group.

In certain embodiments of formula (III) or (IIIA), Z is a cycloalkylamino system of the formula (VI):

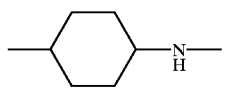

(VI)

wherein the nitrogen atom is optionally substituted with a $C_{1-3}$alkyl, phenyl, or benzyl.

In other preferred embodiments of formula (III) or (IIIA), n is 0.

In certain embodiments of formula (III) or (IIIA), $X_1$ and $X_2$ are both O.

In certain embodiments of formula (III), R is —CH$_2$C(=O)NH$_2$, —C(H)NH$_2$, pyridylmethyl, cyclopentyl, cyclohexyl, furanylmethyl, —C(=O)CH$_3$, —CH$_2$CH$_2$NHC(=O)CH$_3$, —SO$_2$CH$_3$, CH$_2$CH$_2$NHSO$_2$CH$_3$, furanylcarbonyl, methylpyrrolylcarbonyl-, diazolecarbonyl-, azolemethyl-, trifluoroethyl-, hydroxyethyl-, cyanomethyl-, oxo-oxazolemethyl-, or diazolemethyl-.

In certain embodiments of formula (III), $ZR_1$ is cyclohexylethyl-, cyclohexylmethyl-, cyclopentylmethyl-, dimethylcyclohexylmethyl-, phenylethyl-, pyrrolyltrifluoroethyl-, thienyltrifluoroethyl-, pyridylethyl-, cyclopentyl-, cyclohexyl-, methoxycyclohexyl-, tetrahydropyranyl-, propylpiperidinyl-, indolylmethyl-, pyrazoylpentyl-, thiazolylethyl-, phenyltrifluoroethyl-, hydroxyhexyl-, methoxyhexyl-, isopropoxybutyl-, hexyl-, or oxocanylpropyl-.

In certain embodiments of formula (III), at least one of $ZR_1$ or R is —CH$_2$COOV$_1$, tetrazolylmethyl-, cyanomethyl-, NH$_2$SO$_2$methyl-, NH$_2$SOmethyl-, aminocarbonylmethyl-, $C_{1-4}$alkylaminocarbonylmethyl-, or $diC_{1-4}$alkylaminocarbonylmethyl-.

In certain embodiments of formula (III), $ZR_1$ is 3,3 diphenylpropyl optionally substituted at the 3 carbon of the propyl with —COOV$_1$, tetrazolyl$C_{0-4}$alkyl-, cyano-, aminocarbonyl-, $C_{1-4}$alkylaminocarbonyl-, or $diC_{1-4}$ alkylaminocarbonyl-.

The present invention in certain embodiments comprises compounds having the general formula (IV):

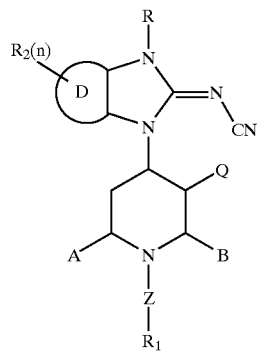

(IV)

wherein R is hydrogen, $C_{1-10}$ alkyl, $C_{3-12}$ cycloalkyl, $C_{3-12}$ cycloalkyl$C_{1-4}$alkyl-, $C_{1-10}$ alkoxy, $C_{3-12}$ cycloalkoxy-, $C_{1-10}$ alkyl substituted with 1–3 halogen, $C_{3-12}$ cycloalkyl substituted with 1–3 halogen, $C_{3-12}$ cycloalkyl$C_{1-4}$alkyl-substituted with 1–3 halogen, $C_{1-10}$ alkoxy substituted with 1–3 halogen, $C_{3-12}$ cycloalkoxy-substituted with 1–3 halogen, —COOV$_1$, —$C_{1-4}$COOV$_1$, —CH$_2$OH, —SO$_2$N(V$_1$)$_2$, hydroxyC$_{1-10}$alkyl-, hydroxyC$_{3-10}$ cycloalkyl-, cyanoC$_{1-10}$alkyl-, cyanoC$_{3-10}$cycloalkyl-, —CON(V$_1$)$_2$, NH$_2$SO$_2$C$_{1-4}$alkyl-, NH$_2$SOC$_{1-4}$alkyl-, sulfonylaminoC$_{1-10}$alkyl-, diaminoalkyl-, -sulfonylC$_{1-4}$ alkyl, a 6-membered heterocyclic ring, a 6-membered heteroaromatic ring, a 6-membered heterocyclicC$_{1-4}$alkyl-, a 6-membered heteroaromaticC$_{1-4}$alkyl-, a 6-membered aromatic ring, a 6-membered aromaticC$_{1-4}$ alkyl-, a 5-membered heterocyclic ring optionally substituted with an oxo or thio, a 5-membered heteroaromatic ring, a 5-membered heterocyclicC$_{1-4}$alkyl-optionally substituted with an oxo or thio, a 5-membered heteroaromaticC$_{1-4}$ alkyl-, —$C_{1-5}$(=O)W$_1$, —$C_{1-5}$(=NH)W$_1$, —$C_{1-5}$NHC(=O)W$_1$, —$C_{1-5}$NHS(=O)$_2$W$_1$, —$C_{1-5}$NHS(=O)W$_1$, wherein $W_1$ is hydrogen, $C_{1-10}$alkyl, $C_{3-12}$ cycloalkyl, $C_{1-10}$ alkoxy, $C_{3-12}$ cycloalkoxy, —CH$_2$OH, amino, $C_{1-4}$alkylamino-, $diC_{1-4}$alkylamino-, or a 5-membered heteroaromatic ring optionally substituted with 1–3 lower alkyl;

wherein each $V_1$ is independently selected from H, $C_{1-6}$ alkyl, $C_{3-6}$ cycloalkyl, benzyl and phenyl;

D is a 5–8 membered cycloalkyl, 5–8 membered heterocyclic or a 6 membered aromatic or heteroaromatic group;

n is an integer from 0 to 3;

A, B and Q are independently hydrogen, $C_{1-10}$ alkyl, $C_{3-12}$ cycloalkyl, $C_{1-10}$ alkoxy, $C_{3-12}$ cycloalkoxy, —CH$_2$OH, —NHSO$_2$, hydroxyC$_{1-10}$alkyl-, aminocarbonyl-, $C_{1-4}$alkylaminocarbonyl-, $diC_{1-4}$alkylaminocarbonyl-, acylamino-, acylaminoalkyl-, amide, sulfonylaminoC$_{1-10}$ alkyl-, or A—B can together form a $C_{2-6}$ bridge, or B—Q can together form a $C_{3-7}$ bridge, or A—Q can together form a $C_{1-5}$ bridge;

Z is selected from the group consisting of a bond, straight or branched $C_{1-6}$ alkylene, —NH—, —CH$_2$O—, —CH$_2$NH—, —CH$_2$N(CH$_3$)—, —NHCH$_2$—, —CH$_2$CONH—, —NHCH$_2$CO—, —CH$_2$CO—, —COCH$_2$—, —CH$_2$COCH$_2$—, —CH(CH$_3$)—, —CH=, —O— and —HC=CH—, wherein the carbon and/or nitrogen atoms are unsubstituted or substituted with one or more lower alkyl, hydroxy, halo or alkoxy group;

$R_1$ is selected from the group consisting of hydrogen, $C_{1-10}$ alkyl, $C_{3-12}$cycloalkyl, $C_{2-10}$alkenyl, amino, $C_{1-10}$alkylamino-, $C_{3-12}$cycloalkylamino-, —COOV$_1$, —$C_{1-4}$ COOV$_1$, cyano, cyanoC$_{1-10}$alkyl-, cyanoC$_{3-10}$cycloalkyl-, $NH_2SO_2$—, $NH_2SO_2C_{1-4}$alkyl-, $NH_2SOC_{1-4}$alkyl-, aminocarbonyl-, $C_{1-4}$alkylaminocarbonyl-, di$C_{1-4}$alkylaminocarbonyl-, benzyl, $C_{3-12}$ cycloalkenyl-, a monocyclic, bicyclic or tricyclic aryl or heteroaryl ring, a hetero-monocyclic ring, a hetero-bicyclic ring system, and a spiro ring system of the formula (V):

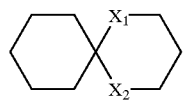

(V)

wherein $X_1$ and $X_2$ are independently selected from the group consisting of NH, O, S and $CH_2$; and wherein said alkyl, cycloalkyl, alkenyl, $C_{1-10}$alkylamino-, $C_{3-12}$cycloalkylamino-, or benzyl of $R_1$ is optionally substituted with 1–3 substituents selected from the group consisting of halogen, hydroxy, $C_{1-10}$ alkyl, $C_{1-10}$ alkoxy, nitro, trifluoromethyl-, cyano, —$COOV_1$, —$C_{1-4}COOV_1$, cyano$C_{1-10}$alkyl-, —$C_{1-5}$(=O)$W_1$, —$C_{1-5}NHS(=O)_2W_1$, —$C_{1-5}NHS(=O)W_1$, a 5-membered heteroaromatic$C_{0-4}$alkyl-, phenyl, benzyl, benzyloxy, said phenyl, benzyl, and benzyloxy optionally being substituted with 1–3 substituents selected from the group consisting of halogen, $C_{1-10}$ alkyl-, $C_{1-10}$ alkoxy-, and cyano; and wherein said $C_{3-12}$ cycloalkyl, $C_{3-12}$ cycloalkenyl, monocyclic, bicyclic or tricyclic aryl, heteroaryl ring, hetero-monocyclic ring, hetero-bicyclic ring system, or spiro ring system of the formula (V) is optionally substituted with 1–3 substituents selected from the group consisting of halogen, $C_{1-10}$ alkyl $C_{1-10}$ alkoxy, nitro, trifluoromethyl-, phenyl, benzyl, phenyloxy and benzyloxy, wherein said phenyl, benzyl, phenyloxy or benzyloxy is optionally substituted with 1–3 substituents selected from the group consisting of halogen, $C_{1-10}$ alkyl, $C_{1-10}$ alkoxy, and cyano;

$R_2$ is selected from the group consisting of hydrogen, $C_{1-10}$ alkyl $C_{3-12}$ cycloalkyl- and halogen, said alkyl or cycloalkyl optionally substituted with an oxo, amino, alkylamino or dialkylamino group;

and pharmaceutically acceptable salts thereof and solvates thereof.

The present invention in certain embodiments comprises compounds having the formula (IVA):

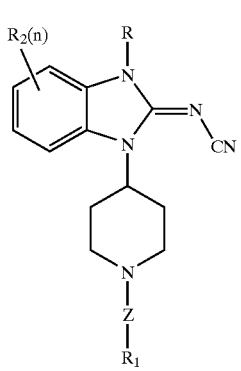

(IVA)

wherein
n is an integer from 0 to 3;
Z is selected from the group consisting of a bond, —$CH_2$—, —NH—, —$CH_2O$—, —$CH_2CH_2$—, —$CH_2NH$—, —$CH_2N(CH_3)$—, —$NHCH_2$—, —$CH_2CONH$—, —$NHCH_2CO$—, —$CH_2CO$—, —$COCH_2$—, —$CH_2COCH_2$—, —$CH(CH_3)$—, —CH=, and —HC=CH—, wherein the carbon and/or nitrogen atoms are unsubstituted or substituted with a lower alkyl, halogen, hydroxy or alkoxy group;

R is selected from the group consisting of hydrogen, $C_{1-10}$ alkyl, $C_{1-10}$ alkoxy, and $C_{3-12}$cycloalkyl;

$R_1$ is selected from the group consisting of hydrogen, $C_{1-10}$alkyl, $C_{3-12}$cycloalkyl, $C_{2-10}$alkenyl, amino, $C_{1-10}$alkylamino, $C_{3-12}$cycloalkylamino, benzyl, $C_{3-12}$ cycloalkenyl, a monocyclic, bicyclic or tricyclic aryl or heteroaryl ring, a heteromonocyclic ring, a heterobicyclic ring system, and a Spiro ring system of the formula (V):

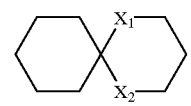

(V)

wherein $X_1$ and $X_2$ are independently selected from the group consisting of NH, O, S and $CH_2$;

wherein said monocyclic aryl is preferably phenyl;
wherein said bicyclic aryl is preferably naphthyl;
wherein said alkyl, cycloalkyl, alkenyl, $C_{1-10}$alkylamino, $C_{3-12}$cycloalkylamino, or benzyl is optionally substituted with 1–3 substituents selected from the group consisting of halogen, $C_{1-10}$ alkyl, $C_{1-10}$ alkoxy, nitro, trifluoromethyl, cyano, phenyl benzyl, benzyloxy, said phenyl, benzyl, and benzyloxy optionally being substituted with 1–3 substituents selected from the group consisting of halogen, $C_{1-10}$ alkyl, $C_{1-10}$ alkoxy, and cyano;

wherein said $C_{3-12}$ cycloalkyl, $C_{3-12}$ cycloalkenyl, monocyclic, bicyclic or tricyclic aryl, heteroaryl ring, heteromonocyclic ring, heterobicyclic ring system, and spiro ring system of the formula (V) are optionally substituted with 1–3 substituents selected from the group consisting of halogen, $C_{1-10}$ alkyl, $C_{1-10}$ alkoxy, nitro, trifluoromethyl, phenyl, benzyl, phenyloxy and benzyloxy, wherein said phenyl, benzyl, phenyloxy and benzyloxy are optionally substituted with 1–3 substituents selected from the group consisting of halogen, $C_{1-10}$ alkyl, $C_{1-10}$ alkoxy, and cyano;

$R_2$ is selected from the group consisting of hydrogen, $C_{1-10}$ alkyl, $C_{3-12}$ cycloalkyl and halogen, said alkyl optionally substituted with an oxo group;

and pharmaceutically acceptable salts thereof.

In certain preferred embodiments of formula (IV), D is phenyl or a 6 membered heteroaromatic group containing 1–3 nitrogen atoms.

In certain preferred embodiments of formula (IV) or (IVA), the $R_1$ alkyl is methyl, ethyl, propyl, butyl, pentyl, or hexyl.

In certain preferred embodiments of formula (IV) or (IVA), the $R_1$ cycloalkyl is cyclohexyl, cycloheptyl, cyclooctyl, cyclononyl, cyclodecyl, or norbornyl.

In other preferred embodiments of formula (IV) or (IVA), the $R_1$ bicyclic ring system is naphthyl. In other preferred embodiments of formula (IV) or (IVA), the $R_1$ bicyclic ring system is tetrahydronaphthyl, or decahydronaphthyl and the $R_1$ tricyclic ring system is dibenzocycloheptyl. In other preferred embodiments $R_1$ is phenyl or benzyl.

In other preferred embodiments of formula (IV) or (IVA), the $R_1$ bicyclic aromatic ring is a 10-membered ring, preferably quinoline or naphthyl.

In other preferred embodiments of formula (IV) or (IVA), the $R_1$ bicyclic aromatic ring is a 9-membered ring, preferably indenyl.

In certain embodiments of formula (IV) or (IVA), Z is a bond, methyl, or ethyl.

In certain embodiments of formula (IV) or (IVA), the Z group is maximally substituted as not to have any hydrogen substitution on the base Z group. For example, if the base Z group is —$CH_2$—, substitution with two methyl groups would remove hydrogens from the —$CH_2$— base Z group.

In other preferred embodiments of formula (IV) or (IVA), n is 0.

In certain embodiments of formula (IV) or (IVA), $X_1$ and $X_2$ are both 0.

In certain embodiments of formula (IV), R is —$CH_2C(=O)NH_2$, —$C(NH)NH_2$, pyridylmethyl, cyclopentyl, cyclohexyl, furanylmethyl, —$C(=O)CH_3$, —$CH_2CH_2NHC(=O)CH_3$, —$SO_2CH_3$, $CH_2CH_2NHSO_2CH_3$, furanylcarbonyl-, methylpyrrolylcarbonyl-, diazolecarbonyl-, azolemethyl-, trifluoroethyl-, hydroxyethyl-, cyanomethyl-, oxo-oxazolemethyl-, or diazolemethyl-.

In certain embodiments of formula (IV), $ZR_1$ is cyclohexylethyl-, cyclohexylmethyl-, cyclopentylmethyl-, dimethylcyclohexylmethyl-, phenylethyl-, pyrrolyltrifluoroethyl-, thienyltrifluoroethyl-, pyridylethyl-, cyclopentyl-, cyclohexyl-, methoxycyclohexyl-, tetrahydropyranyl-, propylpiperidinyl-, indolylmethyl-, pyrazoylpentyl-, thiazolylethyl-, phenyltrifluoroethyl-, hydroxyhexyl-, methoxyhexyl-, isopropoxybutyl-, hexyl-, or oxocanylpropyl-.

In certain embodiments of formula (IV), at least one of $ZR_1$ or R is —$CH_2COOV_1$, tetrazolylmethyl-, cyanomethyl-, $NH_2SO_2$methyl-, $NH_2SO$methyl-, aminocarbonylmethyl-, $C_{1-4}$alkylaminocarbonylmethyl-, or di$C_{1-4}$alkylaminocarbonylmethyl-.

In certain embodiments of formula (IV), $ZR_1$ is 3,3 diphenylpropyl optionally substituted at the 3 carbon of the propyl with —$COOV_1$, tetrazolyl$C_{0-4}$alkyl-, cyano-, aminocarbonyl-, $C_{1-4}$alkylaminocarbonyl-, or di$C_{1-4}$alkylaminocarbonyl-.

In alternate embodiments of formulae (I), (IA), (II), (IIA), (III), (IIIA), (IV), and (IVA), $ZR_1$ can be the following

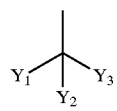

wherein $Y_1$ is $R_3$—($C_1$-$C_{12}$)alkyl, $R_4$-aryl, $R_5$-heteroaryl, $R_6$—($C_3C_{12}$)cyclo-alkyl, $R_7$—($C_3$-$C_7$)heterocycloalkyl, —$CO_2$($C_1$-$C_6$)alkyl, CN or —$C(O)NR_8R_9$; $Y_2$ is hydrogen or $Y_1$; $Y_3$ is hydrogen or ($C_1$-$C_6$)alkyl; or $Y_1$, $Y_2$ and $Y_3$, together with the carbon to which they are attached, form one of the following structures:

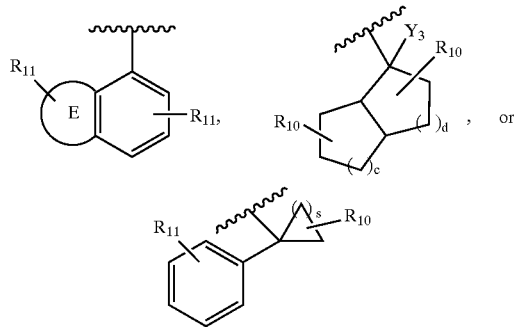

wherein r is 0 to 3; w and u are each 0–3, provided that the sum of w and u is 1–3; c and d are independently 1 or 2; s is 1 to 5; and ring E is a fused $R_4$-phenyl or $R_5$-heteroaryl ring;

$R_{10}$ is 1 to 3 substituents independently selected from the group consisting of H, ($C_1$-$C_6$)alkyl, —$OR_8$, —($C_1$-$C_6$)alkyl-$OR_8$, —$NR_8R_9$ and —($C_1$-$C_6$)alkyl-$NR_8R_9$;

$R_{11}$ is 1 to 3 substituents independently selected from the group consisting of $R_{10}$, —$CF_3$, —$OCF_3$, $NO_2$ and halo, or $R_{11}$ substituents on adjacent ring carbon atoms may together form a methylenedioxy or ethylenedioxy ring;

$R_8$ and $R_9$ are independently selected from the group consisting of hydrogen, ($C_1$-$C_6$) alkyl, ($C_3$-$C_{12}$)cycloalkyl, aryl and aryl($C_1$-$C_6$)alkyl;

$R_3$ is 1 to 3 substituents independently selected from the group consisting of H, $R_4$-aryl, $R_6$—($C_3$-$C_{12}$)cycloalkyl, $R_5$-heteroaryl, $R_7$—($C_3$-$C_7$)heterocycloalkyl, —$NR_8 R_9$, —$OR_{12}$ and —$S(O)_{0-2}R_{12}$;

$R_6$ is 1 to 3 substituents independently selected from the group consisting of H, ($C_1$-$C_6$)alkyl, $R_4$-aryl, —$NR_8R_9$, —$OR_{12}$ and —$SR_{12}$;

$R_4$ is 1 to 3 substituents independently selected from the group consisting of hydrogen, halo, ($C_1$-$C_6$)alkyl, $R_{13}$-aryl, ($C_3$-$C_{12}$)cycloalkyl, —CN, —$CF_3$, —$OR_8$, —($C_1$-$C_6$) alkyl-$OR_8$, —$OCF_3$, —$NR_8R_9$, —($C_1$-$C_6$)alkyl —$NR_8R_9$, —$NHSO_2R_8$, —$SO_2N(R_{14})_2$, —$SO_2R_8$, —$SOR_8$, —$SR_8$, —$NO_2$, —$CONR_8R_9$, —$NR_9COR_8$, —$COR_8$, —$COCF_3$, —$OCOR_8$, —$OCO_2R_8$, —$COOR_8$, —($C_1$-$C_6$)alkyl-NHCOOC($CH_3$)$_3$, —($C_1$-$C_6$)alkyl-NHCOC$F_3$, —($C_1$-$C_6$) alkyl-$NHSO_2$—($C_1$-$C_6$)alkyl, —($C_1$-$C_6$)alkyl-NHCONH—($C_1$-$C_6$)-alkyl and

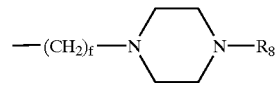

wherein f is 0 to 6; or $R_4$ substituents on adjacent ring carbon atoms may together form a methylenedioxy or ethylenedioxy ring;

$R_5$ is 1 to 3 substituents independently selected from the group consisting of hydrogen, halo, ($C_1$-$C_6$)alkyl, $R_{13}$-aryl, ($C_3$-$C_{12}$)cycloalkyl, —CN, —$CF_3$, —$OR_8$, —($C_1$-$C_6$) alkyl-$OR_8$, —$OCF_3$, —$NR_8R_9$, —($C_1$-$C_6$)alkyl-$NR_8R_9$, —$NHSO_2R_8$, —$SO_2N(R_{14})_2$, —$NO_2$, —$CONR_8R_9$, —$NR_9COR_8$, —$COR_8$, —$OCOR_8$, —$OCO_2R_8$ and —$COOR_8$;

$R_7$ is H, ($C_1$-$C_6$)alkyl, —$OR_8$, —($C_1$-$C_6$)alkyl-$OR_8$, —$NR_8R_9$ or —($C_1$-$C_6$)alkyl-$NR_8R_9$;

$R_{12}$ is H, ($C_1$-$C_6$)alkyl, $R_4$-aryl, —($C_1$-$C_6$)alkyl-$OR_8$, —($C_1$-$C_6$)alkyl-$NR_8R_9$, —($C_1$-$C_6$)alkyl-$SR_8$, or aryl ($C_1$-$C_6$)alkyl;

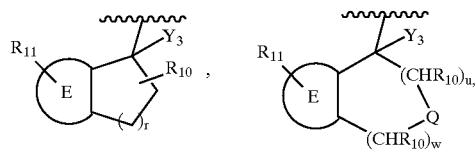

$R_{13}$ is 1–3 substituents independently selected from the group consisting of H, $(C_1-C_6)$alkyl, $(C_1-C_6)$alkoxy and halo;

$R_{14}$ is independently selected from the group consisting of H, $(C_1-C_6)$alkyl and $R_{13}-C_6H_4-CH_2-$.

As used herein, the term "alkyl" means a linear or branched saturated aliphatic hydrocarbon group having a single radical and 1–10 carbon atoms. Examples of alkyl groups include methyl, propyl, isopropyl, butyl, n-butyl, isobutyl, sec-butyl, tert-butyl, and pentyl. A branched alkyl means that one or more alkyl groups such as methyl, ethyl or propyl, replace one or both hydrogens in a $-CH_2-$ group of a linear alkyl chain. The term "lower alkyl" means an alkyl of 1–3 carbon atoms.

The term "alkoxy" means an "alkyl" as defined above connected to an oxygen radical.

The term "cycloalkyl" means a non-aromatic mono- or multicyclic hydrocarbon ring system having a single radical and 3–12 carbon atoms. Exemplary monocyclic cycloalkyl rings include cyclopropyl, cyclopentyl, and cyclohexyl. Exemplary multicyclic cycloalkyl rings include adamantyl and norbornyl.

The term "alkenyl" means a linear or branched aliphatic hydrocarbon group containing a carbon-carbon double bond having a single radical and 2–10 carbon atoms.

A "branched" alkenyl means that one or more alkyl groups such as methyl, ethyl or propyl replace one or both hydrogens in a $-CH_2-$ or $-CH=$ linear alkenyl chain. Exemplary alkenyl groups include ethenyl, 1- and 2-propenyl, 1-, 2- and 3-butenyl, 3-methylbutyl-2-enyl, 2-propenyl, heptenyl, octenyl and decenyl.

The term "cycloalkenyl" means a non-aromatic monocyclic or multicyclic hydrocarbon ring system containing a carbon-carbon double bond having a single radical and 3 to 12 carbon atoms. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "aryl" means a carbocyclic aromatic ring system containing one, two or three rings which may be attached together in a pendent manner or fused, and containing a single radical. Exemplary aryl groups include phenyl, naphthyl and acenaphthyl.

The term "heterocyclic" means cyclic compounds having one or more heteroatoms (atoms other than carbon) in the ring, and having a single radical. The ring may be saturated, partially saturated or unsaturated, and the heteroatoms may be selected from the group consisting of nitrogen, sulfur and oxygen. Examples of saturated heterocyclic radicals include saturated 3 to 6-membered hetero-monocyclic groups containing 1 to 4 nitrogen atoms, such as pyrrolidinyl, imidazolidinyl, piperidino, piperazinyl; saturated 3- to 6-membered hetero-monocyclic groups containing 1 to 2 oxygen atoms and 1 to 3 nitrogen atoms, such as morpholinyl; saturated 3- to 6-membered hetero-monocyclic groups containing 1 to 2 sulfur atoms and 1 to 3 nitrogen atoms, such as thiazolidinyl. Examples of partially saturated heterocyclic radicals include dihydrothiophene, dihydropyran, and dihydrofuran. Other heterocyclic groups can be 7 to 10 carbon rings substituted with heteroatoms such as oxocanyl and thiocanyl. When the heteroatom is sulfur, the sulfur can be a sulfur dioxide such as thiocanyldioxide.

The term "heteroaryl" means unsaturated heterocyclic radicals, wherein "heterocyclic" is as previously described. Exemplary heteroaryl groups include unsaturated 3 to 6 membered hetero-monocyclic groups containing 1 to 4 nitrogen atoms, such as pyrrolyl, pyridyl, pyrimidyl, and pyrazinyl; unsaturated condensed heterocyclic groups containing 1 to 5 nitrogen atoms, such as indolyl, quinolyl and isoquinolyl; unsaturated 3 to 6-membered hetero-monocyclic groups containing an oxygen atom, such as furyl; unsaturated 3 to 6 membered hetero-monocyclic groups containing a sulfur atom, such as thienyl; unsaturated 3 to 6 membered hetero-monocyclic groups containing 1 to 2 oxygen atoms and 1 to 3 nitrogen atoms, such as oxazolyl; unsaturated condensed heterocyclic groups containing 1 to 2 oxygen atoms and 1 to 3 nitrogen atoms, such as benzoxazolyl; unsaturated 3 to 6 membered hetero-monocyclic groups containing 1 to 2 sulfur atoms and 1 to 3 nitrogen atoms, such as thiazolyl; and unsaturated condensed heterocyclic group containing 1 to 2 sulfur atoms and 1 to 3 nitrogen atoms, such as benzothiazolyl. The term "heteroaryl" also includes unsaturated heterocyclic radicals, wherein "heterocyclic" is as previously described, in which the heterocyclic group is fused with an aryl group, in which aryl is as previously described. Exemplary fused radicals include benzofuran, benzdioxole and benzothiophene.

As used herein, the term "heterocyclic$_{1-4}$alkyl", "heteroaromatic$_{1-4}$alkyl" and the like refer to the ring structure bonded to a $C_{1-4}$ alkyl radical.

All of the cyclic ring structures disclosed herein can be attached at any point where such connection is possible, as recognized by one skilled in the art.

As used herein, the term "patient" includes a human or an animal such as a companion animal or livestock.

As used herein, the term "halogen" includes fluoride, bromide, chloride, iodide or alabamide.

The invention disclosed herein is meant to encompass all pharmaceutically acceptable salts thereof of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, fumarate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass all prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Some of the compounds disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The term "modulate" as used herein with respect to the ORL-1 receptor means the mediation of a pharmacodynamic response (e.g., analgesia) in a subject from (i) inhibiting or activating the receptor, or (ii) directly or indirectly affecting the normal regulation of the receptor activity. Compounds which modulate the receptor activity include agonists, antagonists, mixed agonists/antagonists and compounds which directly or indirectly affect regulation of the receptor activity.

Certain preferred compounds of formula (I) and (IA) include:
3-[1-(naphth-2-yl-methyl)-4-piperidinyl]-2H-benzoxazol-2-one;
3-[1-(naphth-1-yl-methyl)-4-piperidinyl]-2H-benzoxazol-2-one;
3-[1-(p-phenylbenzyl)-4-piperidinyl]-2H-benzoxazol-2-one;
3-[1-(p-benzyloxybenzyl)-4-piperidinyl]-2H-benzoxazol-2-one,
3-[1(p-cyanobenzyl)-4-piperidinyl]-2H-benzoxazol-2-one;
3-[1-(3,3-diphenylpropyl)-4-piperidinyl]-2H-benzoxazol-2-one;
3-[1-[4,4-Bis-(4-fluorophenyl)butyl]-4-piperidinyl]-2H-benzoxazol-2-one;
3-[1-(2-phenylethyl)-4-piperidinyl]-2H-benzoxazol-2-one;
3-[1-(cyclooctylmethyl)-4-piperidinyl]-2H-benzoxazol-2-one;
3-[1-(1,2,3,4-tetrahydro-2-naphthyl)-4-piperidinyl]-2H-benzoxazol-2-one;
3-[1-(5-methylhex-2-yl)-4-piperidinyl]-2H-benzoxazol-2-one;
3-[1-(10,11-Dihydro-5H-dibenzo[a,d]-cyclohepten-5-yl)-4-piperidinyl]-2H-benzoxazol-2-one;
3-[1-(4-propyl-cyclohexyl)-4-piperidinyl]-2H-benzoxazol-2-one;
3-[1-(norbornan-2-yl)-4-piperidinyl]-2H-benzoxazol-2-one;
3-[1-(decahydro-2-naphthyl)-4-piperidinyl]-2H-benzoxazol-2-one;
3-[1-(3,3-dimethyl-1,5-dioxaspiro[5.5]undeca-9-yl)-4-piperidinyl]-2H-benzoxazol-2-one;
3-[1-[4-(1-methylethyl)-cyclohexyl]-4-piperidinyl]-2H-benzoxazol-2-one;
3-[1-(1,3-dihydroinden-2-yl)-4-piperidinyl]-2H-benzoxazol-2-one;
3-[1-(cyclooctyl)-4-piperidinyl]-2H-benzoxazol-2-one; and pharmaceutically acceptable salts thereof and solvates thereof.

Certain preferred compounds of formula (II) and (IIA) include:
3-ethylidene-1-[1-(5-methylhex-2-yl)-4-piperidinyl]-1,3-dihydro-2H-indole-2-one;
3-ethylidene-1-[1-(4-propylcyclohexyl)-4-piperidinyl]-1,3-dihydro-2H-indole-2-one;
3-ethylidene-1-[1-(1,2,3,4-tetrahydro-2-naphthyl)-4-piperidinyl]-1,3-dihydro-2H-indole-2-one;
3-ethylidene-1-[1-(1,3-dihydroinden-2-yl)-4-piperidinyl]-1,3-dihydro-2H-indole-2one;
3-ethylidene-1-[1-(naphth-2-yl-methyl)-4-piperidinyl]-1,3-dihydro-2H-indole-2-one;
3-ethylidene-1-[1-(p-benzyloxybenzyl)-4-piperidinyl]-1,3-dihydro-2H-indole-2-one;
3-ethylidene-1-[1-(benzyl)-4-piperidinyl]-1,3-dihydro-2H-indole-2-one;
3-ethylidene-1-[1-(cyclooctylmethyl)-4-piperidinyl]-1,3-dihydro-2H-indole-2-one;
3-ethylidene-1-[1-(norbornan-2-yl)-4-piperidinyl]-1,3-dihydro-2H-indole-2-one;
3-ethylidene-1-[1-(3,3-diphenylpropyl)-4-piperidinyl]-1,3-dihydro-2H-indole-2-one;
3-ethylidene-1-[1-(p-cyanobenzyl)-4-piperidinyl]-1,3-dihydro-2H-indole-2-one;
3-ethyl-1-[1-(5-methylhex-2-yl)-4-piperidinyl]-1,3-dihydro-2H-indole-2-one;
3-ethyl-1-[1-[4-(1-methylethyl)-cyclohexyl]-4-piperidinyl]-1,3-dihydro-2H-indole-2-one;
3-ethyl-1-[1(4-propylcyclohexyl)-4-piperidinyl]-1,3-dihydro-2H-indole-2-one;
3-ethyl-1-[1-(1,2,3,4-tetrahydro-2-naphthyl)-4-piperidinyl]-1,3-dihydro-2H-indole-2-one;
3-ethyl-1-[1-(decahydro-2-naphthyl)-4-piperidinyl]-1,3-dihydro-2H-indole-2-one;
3-ethyl-1-[1-(1,3-dihydroinden-2-yl)-4-piperidinyl]-1,3-dihydro-2H-indole-2-one;
3-ethyl-1-[1-(cyclooctylmethyl)-4-piperidinyl]-1,3-dihydro-2H-indole-2-one;
3-ethyl-1-[1-(norbornan-2-yl)-4-piperidinyl]-1,3-dihydro-2H-indole-2-one;
1-[1-(naphth-1-yl-methyl)-4-piperidinyl]-1,3-dihydro-2H-indole-2-one;
1-[1-(naphth-2-yl-methyl)-4-piperidinyl]-1,3-dihydro-2H-indole-2-one;
1-[1-(p-phenylbenzyl)-4-piperidinyl]-1,3-dihydro-2H-indole-2-one;
1-[1-(3,3-Bis(phenyl)propyl)-4-piperidinyl]-1,3-dihydro-2H-indole-2-one;
1-[1-(p-cyanobenzyl)-4-piperidinyl]-1,3-dihydro-2H-indole-2-one;
1-[1-(p-benzyloxybenzyl)-4-piperidinyl]-1,3-dihydro-2H-indole-2-one;

1-[1-(1,2,3,4-tetrahydronaphth-2-yl)-4-piperidinyl]-1,3-dihydro-2H-indole-2-one;
1-[1(5-methylhex-2-yl)-4-piperidinyl]-1,3-dihydro-2H-indole-2-one;
1-[1-(norbornan-2-yl)-4-piperidinyl]-1,3-dihydro-2H-indole-2-one;
1-[1-(1,3-dihydroinden-2-yl)-4-piperidinyl]-1,3-dihydro-2H-indole-2-one;
1-[1-(cycooctylmethyl)-4-piperidinyl]-1,3-dihydro-2H-indole-2-one;
1-[1-(benzyl)-3-(methyl)-4-piperidinyl]-1,3-dihydro-2H-indole-2-one;
1-[1-(4-propyl-cyclohexyl)-3-(methyl)-4-piperidinyl]-1,3-dihydro-2H-indole-2-one
1-[1-(5-methylhex-2-yl)-3-(methyl)-4-piperidinyl]-1,3-dihydro-2H-indole-2-one;
1-[1-(decahydro-2-naphthyl)-3-(methyl)-4-piperidinyl]-1,3-dihydro-2H-indole-2-one;
1-[1-(4-(1-methylethyl)-cyclohexyl)-3-(methyl)-4-piperidinyl]-1,3-dihydro-2H-indole-2-one;
1-[1-(cyclooctylmethyl)-3-(methyl)-4-piperidinyl]-1,3-dihydro-2H-indole-2-one;
1-[1-(3,3-Bis(phenyl)propyl)-3-(methyl)-4-piperidinyl]-1,3-dihydro-2H-indole-2-one;
3-ethyl-1-[1-(3,3-Bis(phenyl)propyl)-3-(methyl)-4-piperidinyl]-1,3-dihydro-2H-indole-2-one;
3-ethyl-1-[1-(4-propylcyclohexyl)-3-(methyl)-4-piperidinyl]-1,3-dihydro-2H-indole-2-one;
3-ethyl-1-[1-(5-methylhex-2-yl)-3-(methyl)-4-piperidinyl]-1,3-dihydro-2H-indole-2-one;
3-ethyl-1-[1-[4-(1-methylethyl)cyclohexyl]-3-methyl-4-piperidinyl]-1,3-dihydro-2H-indole-2-one;
3-ethyl-1-[1-(decahydro-2-naphthyl)-3-(methyl)-4-piperidinyl]-1,3-dihydro-2H-indole-2-one; and
mpharmaceutically acceptable salts thereof and solvates thereof.

Certain preferred compounds of formula (III) and (IIIA) include:
3-ethyl-1-(p-phenylbenzyl)-1,3-dihydro-2H-benzimidazol-2-one;
3-ethyl-1-(5-methylhex-2-yl)-1,3-dihydro-2H-benzimidazol-2-one;
3-ethyl-1-(4-propylcyclohexyl)-1,3-dihydro-2H-benzimidazol-2-one;
3-ethyl-1-(decahydro-2-naphthyl)-1,3-dihydro-2H-benzimidazol-2-one;
3-ethyl-1-(naphth-2-yl-methyl)-1,3-dihydro-2H-benzimidazol-2-one;
1-(p-benzyloxybenzyl)-3-ethyl-1,3-dihydro-2H-benzimidazol-2-one;
1-benzyl-3-ethyl-1,3-dihydro-2H-benzimidazol-2-one;
1-[4-(benzylamino)-cyclohexyl]-3-ethyl-1,3-dihydro-2H-benzimidazol-2-one;
3-ethyl-1-(naphthylmethyl)-1,3-dihydro-2H-benzimidazol-2-one;
3-ethyl-1-[5-(3-fluorophenyl)-5-(4-fluorophenyl)-hexyl]-1,3-dihydro-2H-benzimidazol-2-one;
1-[4-[(naphth-2-yl-methyl)ethylamino]-cyclohexyl]-1,3-dihydro-2H-benzimidazol-2-one;
1-[4-(norbornan-2-ylamino)-cyclohexyl]-1,3-dihydro-2H-benzimidazol-2-one;
1-[4-[[4-(1-methylethyl)-cyclohexyl]amino]-cyclohexyl]-1,3-dihydro-2H-benzimidazol-2-one;
1-[4-[(decahydro-2-naphthyl)amino]-cyclohexyl]-1,3-dihydro-2H-benzimidazol-2-one;
1-[4-(ethylamino)-cyclohexyl]-1,3-dihydro-2H-benzimidazol-2-one;
1-[4-(benzylamino)-cyclohexyl]-1,3-dihydro-2H-benzimidazol-2-one;
1-[4-[(indan-2-yl)benzylamino]-cyclohexyl]-3-ethyl-1,3-dihydro-2H-benzimidazol-2-one;
1-[4-[(cyclooctylmethyl)amino]-cyclohexyl]-3-ethyl-1,3-dihydro-2H-benzimidazol-2-one;
1-[4-[(naphth-2-yl)amino]-cyclohexyl]-3-ethyl-1,3-dihydro-2H-benzimidazol-2-one;
1-[4-[(p-benzyloxybenzyl)amino]-cyclohexyl]-3-ethyl-1,3-dihydro-2H-benzimidazol-2-one;
1-[4-[(cyclooctylmethyl)amino]-cyclohexyl]-3-ethyl-1,3-dihydro-2H-benzimidazol-2-one;
1-[4-[(decahydro-2-naphthyl)amino]-cyclohexyl]-3-ethyl-1,3-dihydro-2H-benzimidazol-2-one;
1-[4-(benzylamino)-cyclohexyl]-5-carbamoyl-1,3-dihydro-2H-benzimidazol-2-one;
1-[4-(dibenzylamino)-cyclohexyl]-5-carbamoyl-1,3-dihydro-2H-benzimidazol-2-one;
1-[4-[(p-phenylbenzyl)amino]-cyclohexyl]-5-carbamoyl-1,3-dihydro-2H-benzimidazol-2-one;
1-[4-[(1,2,3,4-tetrahydronaphthyl)amino]-cyclohexyl]-5-carbamoyl-1,3-dihydro-2H-benzimidazol-2-one;
1-[4-[(4-propyl-cyclohexyl)amino]-cyclohexyl]-5-carbamoyl-1,3-dihydro-2H-benzimidazol-2-one;
1-[4-[(5-methylhex-2-yl)amino]-cyclohexyl]-5-carbamoyl-1,3-dihydro-2H-benzimidazol-2-one;
1-[4-[(decahydro-2-naphthyl)amino]-cyclohexyl]-5-carbamoyl-1,3-dihydro-2H-benzimidazol-2-one;
1-[4-(cyclooctylamino)-cyclohexyl]-5-carbamoyl-1,3-dihydro-2H-benzimidazol-2-one;
1-[4-[(indan-2-yl)amino]-cyclohexyl]-5-carbamoyl-1,3-dihydro-2H-benzimidazol-2-one;
1-[4-[(4-phenyl-cyclohexyl)amino]-cyclohexyl]-5-carbamoyl-1,3-dihydro-2H-benzimidazol-2-one;
1-[4-[(5-methylhex-2-yl)amino]-cyclohexyl]-7-carbamoyl-1,3-dihydro-2H-benzimidazol-2-one; and
pharmaceutically acceptable salts thereof and solvates thereof.

Other preferred compounds formula (IV) and (IVA) include:
2-cyanoimino-3-ethyl-1-[1-(p-phenylbenzyl)-4-piperidinyl]-1,3-dihydro-2H-benzimidazole;
2-cyanoimino-3-ethyl-1-[1-(p-benzyloxybenzyl)-4-piperidinyl]1,3-dihydro-2H-benzimidazole;
2-cyanoimino-3-ethyl-1-[1-(naphth-2-yl-methyl)-4-piperidinyl]1,3-dihydro-2H-benzimidazole;
2-cyanoimino-3-ethyl-1-[1-(4-propylcyclohexyl)-4-piperidinyl]-1,3-dihydro-2H-benzimidazole;
2-cyanoimino-3-ethyl-1-[1-[4-(2-propyl)-cyclohexyl]-4-piperidinyl]-1,3-dihydro-2H-benzimidazole;
2-cyanoimino-3-ethyl-1-[1-(decahydro-2-naphthyl)-4-piperidinyl]-1,3-dihydro-2H-benzimidazole;
2-cyanoimino-3-ethyl-1-[1-(cyclooctyl)-4-piperidinyl]-1,3-dihydro-2H-benzimidazole;
2-cyanoimino-3-ethyl-1-[1-(10,11-dihydro-5H-dibenzo[a,d]-cyclohepten-5-yl)-4-piperidinyl]-1,3-dihydro-2H-benzimidazole;
2-cyanoimino-3-ethyl-1-[1-(3,3-Bis(phenyl)propyl)-4-piperidinyl]-1,3-dihydro-2H-benzimidazole;
2-cyanoimino-3-ethyl-1-[1-(1,2,3,4-tetrahydronaphthyl)-4-piperidinyl]-1,3-dihydro-2H-benzimidazole;
2-cyanoimino-3-ethyl-1-[1-(5-methylhex-2-yl)-4-piperidinyl]-1,3-dihydro-2H-benzimidazole;
2-cyanoimino-3-ethyl-1-[1-(norbornan-2-yl)-4-piperidinyl]-1,3-dihydro-2H-benzimidazole;
2-cyanoimino-3-ethyl-1-[1-(1,3-dihydroinden-2-yl)-4-piperidinyl]-1,3-dihydro-2H-benzimidazole;

2-cyanoimino-3-ethyl-1-[1-(cyclooctylmethyl)-4-piperidinyl]-1,3-dihydro-2H-benzimidazole; and pharmaceutically acceptable salts thereof and solvates thereof.

Other preferred compounds of formula (IV) include 2-cyanoimino-3-(2-hydroxy)ethyl-1-[1-(cyclooctyl)-4-piperidinyl]-1,3-dihydro-2H-benzimidazole;

2-cyanoimino-3-methoxycarbonylmethyl-1-[1-(cyclooctyl)-4-piperidinyl]-1,3-dihydro-2H-benzimidazole;

2-cyanoimino-3-cyanomethyl-1-[1-(cyclooctyl)-4-piperidinyl]-1,3-dihydro-2H-benzimidazole;

2-cyanoimino-3-butyl-1-[1-(cyclooctyl)-4-piperidinyl]-1,3-dihydro-2H-benzimidazole;

2-cyanoimino-3-(2-methanesulfonamido)ethyl-1-[1-(cyclooctyl)-4-piperidinyl]-1,3-dihydro-2H-benzimidazole;

2-cyanoimino-3-acetomido-1-[1-(cyclooctyl)-4-piperidinyl]-1,3-dihydro-2H-benzimidazole;

2-cyanoimino-3-carboxymethyl-1-[1-(cyclooctyl)-4-piperidinyl]-1,3-dihydro-2H-benzimidazole;

2-cyanoimino-3-(2-dimethylamino)ethyl-1-[1-(cyclooctyl)-4-piperidinyl]-1,3-dihydro-2H-benzimidazole;

2-cyanoimino-1-[1-(cyclooctyl)-3-hydroxymethyl-4-piperidinyl]-1,3-dihydro-2H-benzimidazole;

2-cyanoimino-1-[1-(cyclooctyl)-4-piperidinyl]-1,3-dihydro-2H-7-azabenzimidazole;

2-cyanoimino-1-[1-(cyclooctyl)-2,6-ethano-4-one-4-piperidinyl]-1,3-dihydro-2H-benzimidazole; and pharmaceutically acceptable salts thereof and solvates thereof.

The present invention also provides use of any of the disclosed compounds in the preparation of a medicament for treating pain and other disease states modulated by an opioid receptor, e.g., the ORL-1 receptor.

DETAILED DESCRIPTION OF THE INVENTION

The compounds of the present invention can be administered to anyone requiring modulation of the opioid and ORL-1 receptors. Administration may be orally, topically, by suppository, inhalation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients*, American Pharmaceutical Association (1986). Techniques and compositions for making solid oral dosage forms are described in *Pharmaceutical Dosage Forms: Tablets* (Lieberman, Lachman and Schwartz, editors) 2nd edition, published by Marcel Dekker, Inc. Techniques and compositions for making tablets (compressed and molded), capsules (hard and soft gelatin) and pills are also described in *Remington's Pharmaceutical Sciences* (Arthur Osol, editor), 1553B1593 (1980). Techniques and composition for making liquid oral dosage forms are described in *Pharmaceutical Dosage Forms: Disperse Systems*, (Lieberman, Rieger and Banker, editors) published by Marcel Dekker, Inc.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

In certain embodiments, the compounds of the present invention can be used in combination with at least one other therapeutic agent. Therapeutic agents include, but are not limited to, μ-opioid agonists; non-opioid analgesics; non-steroid antiinflammatory agents; Cox-II inhibitors; antiemetics; β-adrenergic blockers; anticonvulsants; antidepressants; Ca2+-channel blockers; anticancer agent and mixtures thereof.

In certain embodiments, the compounds of the present invention can be formulated in a pharmaceutical dosage form in combination with a μ-opioid agonist. μ-opioid agonists, which may be included in the formulations of the present invention include but are not limited to include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain preferred embodiments, the μ-opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

In another embodiment of the invention, the medicament comprises a mixture of a Cox-II inhibitor and an inhibitor of 5-lipoxygenase for the treatment of pain and/or inflammation. Suitable Cox-II inhibitors and 5-lipoxygenase inhibitors, as well as combinations thereof are described in U.S. Pat. No. 6,136,839, which is hereby incorporated by reference in its entirety. Cox-II inhibitors include, but are not limited to rofecoxib (Vioxx), celecoxib (Celebrex), DUP-697, flosulide, meloxicam, 6-MNA, L-745337, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib and parecoxib or pharmaceutically acceptable salts, enantiomers or tautomers thereof.

The compounds of the present invention can also be combined in dosage forms with non-opioid analgesics, e.g., non-steroidal anti-inflammatory agents, including aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam or isoxicam, pharmaceutically acceptable salts thereof, and mixtures thereof. Other suitable non-opioid analgesics which may be included in the dosage forms of the present invention include the following, non-limiting, chemical classes of analgesic, antipyretic, non-steroidal antifinflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs that may be included within the medicaments employed in the present invention, see Paul A. Insel Analgesic-Antipyretic and Antiinflammatory Agents and Drugs Employed in the treatment of Gout in Goodman & Gilman's The Pharmacological Basis of Therapeutics, 617–57 (Perry B. Molinhoff and Raymond W. Ruddon, Eds., Ninth Edition, 1996), and Glen R. Hanson Analgesic, Antipyretic and Anit-Inflammatory Drugs in Remington: The Science and Practice of Pharmacy Vol II, 1196–1221 (A. R. Gennaro, Ed. 19th Ed. 1995) which are hereby incorporated by reference in their entireties.

In certain embodiments, the compounds of the present invention can be formulated in a pharmaceutical dosage form in combination with antimigraine agents. Antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

The other therapeutic agent can also be an adjuvant to reduce any potential side effects such as, for example, an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

In certain embodiments, the compounds of the present invention can be formulated in a pharmaceutical dosage form in combination with β-adrenergic blockers. Suitable β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

In certain embodiments, the compounds of the present invention can be formulated in a pharmaceutical dosage form in combination with anticonvulsants. Suitable anticonvulsants include, but are not limited to, acetylpheneturide, albutoin, aloxidone, aminoglutethimide, 4-amino-3-hydroxybutyric acid, atrolactamide,beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

In certain embodiments, the compounds of the present invention can be formulated in a pharmaceutical dosage form in combination with antidepressants. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

In certain embodiments, the compounds of the present invention can be formulated in a pharmaceutical dosage form in combination with Ca2+-channel blockers. Suitable Ca2+-channel blockers include, but are not limited to, bepridil, clentiazem, diltiazem, fendiline, gallopamil, mibefradil, prenylamine, semotiadil, terodiline, verapamil, amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

In certain embodiments, the compounds of the present invention can be formulated in a pharmaceutical dosage form in combination with anticancer agents. Suitable anticancer agents include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluoroutacil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethnyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The compounds of the present invention and the other therapeutic agent can act additively or, more preferably, synergistically. In a preferred embodiment, a composition comprising a compounds of the present invention is administered concurrently with the administration of another therapeutic agent, which can be part of the same composition or in a different composition from that comprising the compounds of the present invention. In another embodiment, a composition comprising the compounds of the present invention is administered prior to or subsequent to administration of another therapeutic agent.

The compounds of the present invention when administered, e.g., via the oral, parenteral or topical routes to mammals, can be in a dosage in the range of about 0.01 mg/kg to about 3000 mg/kg body weight of the patient per day, preferably about 0.01 mg/kg to about 1000 mg/kg body weight per day administered singly or as a divided dose. However, variations will necessarily occur depending upon the weight and physical condition (e.g., hepatic and renal function) of the subject being treated, the affliction to be treated, the severity of the symptoms, the route of administration, the frequency of the dosage interval, the presence of any deleterious side-effects, and the particular compound utilized, among other things.

The compounds of the present invention preferably have a binding affinity $K_i$ for the human ORL-1 receptor of about 500 nM or less; 100 nM or less; 50 nM or less; 20 nM or less or 5 nM or less. The binding affinity $K_i$ can be measured by one skilled in the art by an assay utilizing membranes from recombinant HEK-293 cells expressing the human opioid receptor-like receptor (ORL-1) as described below.

The following examples illustrate various aspects of the present invention, and are not to be construed to limit the claims in any manner whatsoever.

EXAMPLE 1

Synthesis of Benzoxazolone Head Groups

The head groups of the present invention were synthesized according to the following procedure:

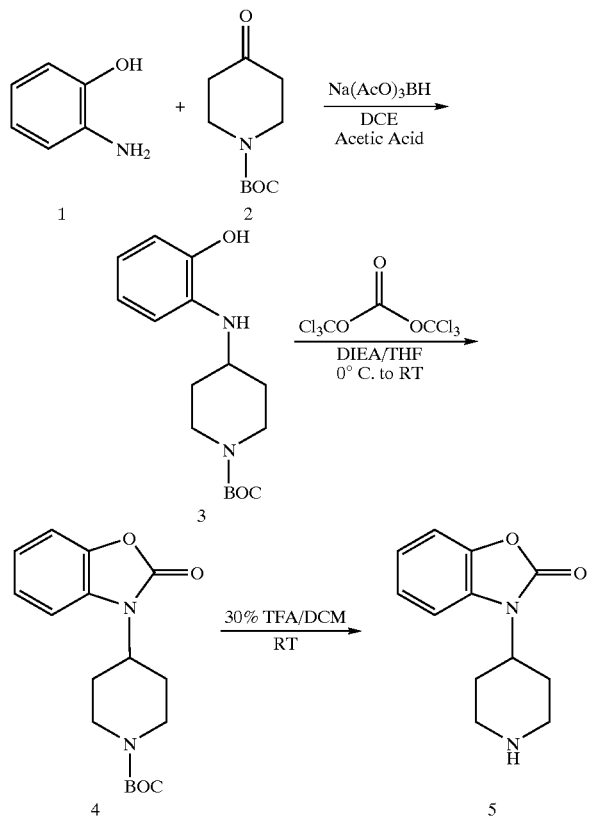

Procedure:

To a mixture of 1 (1.09 g, 10 mmol), 2 (1.99 g, 10 mmol) and acetic acid (0.60 g, 10 mmol) in 50 mL of dichloroethane, was added sodium triacetoxyborohydride (2.97 g, 14 mmol). The mixture was stirred at room temperature overnight. The mixture was filtered through Celite and 1 N NaOH (50 mL) was added to quench the reaction. The organic layer was separated and the aqueous layer was extracted with EtOAc (2×30 mL). The combined organic layers were dried over $K_2CO_3$, filtered and evaporated in vacuum to give crude 3 as a brown solid (2.75 g, yield: 94%).

$^1$H NMR (CDCl$_3$): d 1.20–1.60 (m, 11H), 2,00 (dd, 2H), 2.9 (m, 2H), 3.40 (m, 1H), 4.00 (m, 2H), 6.60–6.85 (m, 4H).

To an ice cooled solution of crude 3 (12.0 g, 40 mmol) and DIEA (20.8 mL, 120 mmol) in 200 mL of THF, was added a solution of triphosgene (4.32 g, 14.4 mmol) in 200 mL of THF. After the addition was complete the ice bath was removed and the mixture stirred at room temperature overnight. The solids were filtered off and the filtrate evaporated in vacuum. The residual brown oil was dissolved in EtOAc and washed with saturated aqueous $K_2CO_3$. The organic phase was dried over $K_2CO_3$, filtered and evaporated in vacuum to give a red oil which was filtered through a column of silica gel eluting with a mixture of 5% Et$_3$N, 25% EtOAc and 70% hexane. The selected fractions were combined and the solvent evaporated in vacuum to give a brown solid which was crystallized from EtOAc to give pure 4 (10.0 g, 78% yield).

$^1$H NMR (CDCl$_3$): d 1.50 (s, 9H), 1.85 (d, 2H), 2.25 (m, 2H), 2.85 (m, 2H), 4.20–4.45 (m, 3H), 7.00–7.25 (m, 4H).

A solution of 4 (4.0 g, 17.2 mmol) in 30% TFA/dichloromethane (25 mL) was stirred at room temperature for 3 h. The solvent was evaporated in vacuum and saturated aqueous $K_2CO_3$ was added to the oily residue. The resulting mixture was extracted with dichloromethane (3×50 mL). The combined organic extracts were dried over $K_2CO_3$, filtered and evaporated in vacuum to give the crude product. Chromatography on silica gel eluting with a mixture of 10% Et$_3$N, 60% EtOAc and 30% hexane gave 5 as a yellow solid (1.82 g, 66% yield).

MS: m/z 450 $^1$H NMR (CDCl$_3$): d 1.75–2.10 (m, 3H), 2.30 (d, 2H), 2.80 (m, 2H), 3.20 (m, 2H), 4.25 (m, 1H), 7.00–7.25 (m, 4H).

EXAMPLE 2

Attachment of Tail Groups

Tail groups were attached to the head groups according to the following procedures:

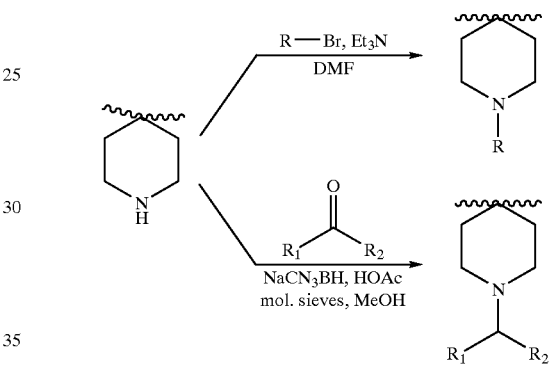

General Procedure for Alkylation:

To a solution of the amine (1 eq) and triethylamine (1 eq) in dimethylformamide, was added 1 eq of alkyl bromide or chloride in one portion. The mixture was stirred and heated at 80° C. over night. TLC indicated the reaction was complete. The reaction was quenched by the addition of water followed by 1 N NaOH to pH 10. The mixture was extracted 2× with Et$_2$O. The combined organic extracts were dried over potassium carbonate and the solvent evaporated, followed by chromatography to give the pure product.

General Procedure for Reductive Amination:

To a mixture of ketone or aldehyde (1 eq), amine (1 eq), and acetic acid (1 eq) in methanol, was added sodium cyanoborohydride (1.4 eq) in one portion. The mixture was stirred over night at room temperature. TLC indicated the reaction was complete. The reaction was quenched by the addition of water followed by 1 N NaOH to pH 10. The mixture was extracted 2× with Et$_2$O. The combined organic extracts were dried over potassium carbonate and the solvent evaporated, followed by chromatography to give the pure product.

The following compounds were prepared by attaching the tail groups using the general procedures described:

3-[1-(naphth-2-yl-methyl)-4-piperidinyl]-2H-benzoxazol-2-one
3-[1-(naphth-1-yl-methyl)-4-piperidinyl]-2H-benzoxazol-2-one
3-[1-(p-phenylbenzyl)-4-piperidinyl]-2H-benzoxazol-2-one
3-[1-(p-benzyloxybenzyl)-4-piperidinyl]-2H-benzoxazol-2-one 3-[1-(p-cyanobenzyl)-4-piperidinyl]-2H-benzoxazol-2-one
MS: m/z 334.4 (M+1)
3-[1-(3,3-diphenylpropyl)-4-piperidinyl]-2H-benzoxazol-2-one
3-[1-[4,4-Bis-(4-fluorophenyl)butyl]-4-piperidinyl]-2H-benzoxazol-2-one
MS: m/z 463.6 (M+1).
3-[1-(2-phenylethyl)-4-piperidinyl]-2H-benzoxazol-2-one
3-[1-(cyclooctylmethyl)-4-piperidinyl]-2H-benzoxazol-2-one
LC: 100%
MS: m/z 343.6 (M+1).
$^1$H—NMR (CDCl$_3$): d 1.25 (m, 2H), 1.40–1.7 (m, 17H), 2.10 (m, 4H), 3.10 (m, 2H), 4.20 (m, 1H), 7.10–7.20 (4H).
13C—NMR (CDCl$_3$): d 26.02, 26.87, 27.55, 29.27, 31.23, 35.31, 53.39, 53.70, 66.28, 110.45, 110.51, 122.45, 123.96, 130.45, 143.08, 154.51.
3-[1-(1,2,3,4-tetrahydro-2-naphthyl)-4-piperidinyl]-2H-benzoxazol-2-one
LC: 100%
MS: 349.6 (M+1)
$^1$H—NMR (CDCl$_3$): d 1.70 (m, 1H), 2.00 (b, 2H), 2.10 (b, 1H), 2.40 (m, 4H), 2.90 (m, 5H), 3.10 (m, 2H), 4.20 (m, 1H), 7.10–7.30 (m, 8H).
3-[1-(5-methylhex-2-yl)-4-piperidinyl]-2H-benzoxazol-2-one
LC: 100%
MS: 317.4 (M+1)
$^1$H—NMR (CDCl$_3$): d 0.90 (d, 6H), 1.00 (d, 3H), 1.20 (m, 3H), 1.50–1.60 (m, 4H), 1.80 (m, 2H), 2.20–2.60 (m, 5H), 2.90 (b, 2H), 4.2 (m, 1H), 6.90–7.30 (m, 4H).
3-[1-(10,11-Dihydro-5H-dibenzo[a,d]-cyclohepten-5-yl)-4-piperidinyl]-2H-benzoxazol-2-one
LC: 96.4%
$^1$H—NMR (CDCl$_3$): d 1.80 (dd, 2H), 2.00 (dt, 2H), 2.30 (dq, 2H), 2.80–2.95 (m, 4H), 4.01 (s, 1H), 4.05–4.22 (m, 3H), 7.05–7.25 (m, 12H).
3-[1-(4-propyl-cyclohexyl)-4-piperidinyl]-2H-benzoxazol-2-one
MS: m/z 343.0
3-[1-(norbornan-2-yl)-4-piperidinyl]-2H-benzoxazol-2-one
LC: 97%
MS: m/z 313.41 (M+1)
$^1$H—NMR (CDCl$_3$): d 0.90 (m,1H), 1.30–2.50 (m,17H), 3.20 (m,2H), 4.3 (m, 1H), 6.90–7.30 (m, 4H).
3-[1-(decahydro-2-naphthyl)-4-piperidinyl]-2H-benzoxazol-2-one
MS: m/z 355.4
3-[1-(3,3-dimethyl-1,5-dioxaspiro[5.5]undeca-9-yl)-4-piperidinyl]-2H-benzoxazol-2-one
MS: m/z 401.3
3-[1-[4-(1-methylethyl)-cyclohexyl]-4-piperidinyl]-2H-benzoxazol-2-one
MS: m/z 343.0
3-[1-(1,3-dihydroinden-2-yl)-4-piperidinyl]-2H-benzoxazol-2-one
LC: 100%
MS: m/z 335.4 (M+1)
$^1$H—NMR (CDCl$_3$): d 1.90 (m, 1H), 2.40 (m, 2H), 2.50 (m, 2H), 2.90 (m, 2H), 3.10–3.40 (m, 6H), 4.20 (m, 1H), 7.10–7.30 (m, 8H).
3-[1-(cyclooctyl)-4-piperidinyl]-2H-benzoxazol-2-one
LC: 100%
MS: m/z 329.2 (M+1)
$^1$H—NMR (CDCl$_3$): d 1.40–2.00 (m, 16H), 2.40–2.65 (m, 4H), 2.80 (m, 1H), 3.05 (m, 2H), 4.25 (m, 1H), 7.10–7.40 (m, 4H).

Other compounds within the scope of formula (I) or (IA) of the present invention can be synthesized by analogous techniques.

EXAMPLE 3

Nociceptin affinity at the ORL1 receptor for preferred compounds was obtained using the following assay:

Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 ml/10 cm dish) followed by homogenization with a tissue grinder/teflon pestle. Membranes were collected by centrifugation at 30,000× g for 15 min at 4° C. and pellets resuspended in hypotonic buffer to a final concentration of 1–3 mg/ml. Protein concentrations were determined using the BioRad protein assay reagent with bovine serum albumen as standard. Aliquots of the ORL-1 receptor membranes were stored at –80° C.

Functional SGTPgS binding assays were conducted as follows. ORL-1 membrane solution was prepared by sequentially adding final concentrations of 0.066 mg/ml ORL-1 membrane protein, 10 mg/ml saponin, 3 mM GDP and 0.20 nM [$^{35}$S]GTPgS to binding buffer (100 mM NaCl, 10 mM MgCl$_2$, 20 mM HEPES, pH 7.4) on ice. The prepared membrane solution (190 ml/well) was transferred to 96-shallow well polypropylene plates containing 10 ml of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 200 ml ice-cold binding buffer (10 mM NaH$_2$PO$_4$, 10 mM Na$_2$HPO$_4$, pH 7.4). Filter plates were subsequently dried at 50° C. for 2–3 hours. Fifty ml/well scintillation cocktail (BetaScint; Wallac) was added and plates were counted in a Packard Top-Count for 1 min/well.

Data was analyzed using the curve fitting functions in GraphPad PRISMÔ, v.3.0 and the results are set forth in table 1 below:

TABLE 1

Nociceptin Affinity

| Compound | Calc K$_i$ (nM) |
|---|---|
| 3-[1-(naphth-2-yl-methyl)-4-piperidinyl]-2H-benzoxazol-2-one | 3030 |
| 3-[1-(naphth-1-yl-methyl)-4-piperidinyl]-2H-benzoxazol-2-one | 370 |
| 3-[1-(p-phenylbenzyl)-4-piperidinyl]-2H-benzoxazol-2-one | >10,000 |
| 3-[1-(p-benzyloxybenzyl)-4-piperidinyl]-2H-benzoxazol-2-one | 2173 |
| 3-[1-(p-cyanobenzyl)-4-piperidinyl]-2H-benzoxazol-2-one | >10,000 |
| 3-[1-(3,3-diphenylpropyl)-4-piperidinyl]-2H-benzoxazol-2-one | 726 |
| 3-[1-[4,4-Bis-(4-fluorophenyl)butyl]-4-piperidinyl]-2H-benzoxazol-2-one | 3070 |
| 3-[1-(2-phenylethyl)-4-piperidinyl]-2H-benzoxazol-2-one | 7087 |
| 3-[1-(cyclooctylmethyl)-4-piperidinyl]-2H-benzoxazol-2-one | 64 |
| 3-[1-(1,2,3,4-tetrahydro-2-naphthyl)-4-piperidinyl]-2H-benzoxazol-2-one | 93 |
| 3-[1-(5-methylhex-2-yl)-4-piperidinyl]-2H-benzoxazol-2-one | 60 |
| 3-[1-(10,11-Dihydro-5H-dibenzo[a,d]-cyclohepten-5-yl)-4-piperidinyl]-2H-benzoxazol-2-one | >10,000 |
| 3-[1-(3,3-dimethyl-1,5-dioxaspiro[5.5]undeca-9-yl)-4-piperidinyl]-2H-benzoxazol-2-one | >10,000 |
| 3-[1-(1,3-dihydroinden-2-yl)-4-piperidinyl]-2H-benzoxazol-2-one | 512 |
| 3-[1-(cyclooctyl)-4-piperidinyl]-2H-benzoxazol-2-one | 16 |

EXAMPLE 4

Synthesis of Substituted Indole Head Groups

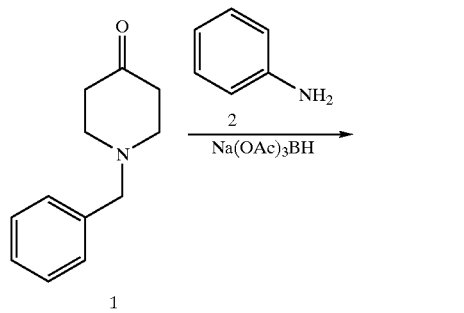

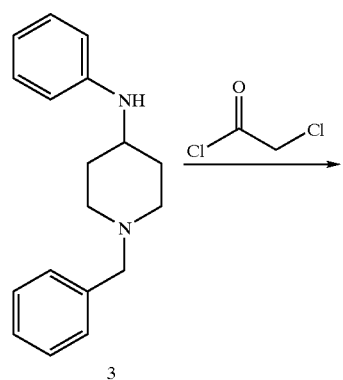

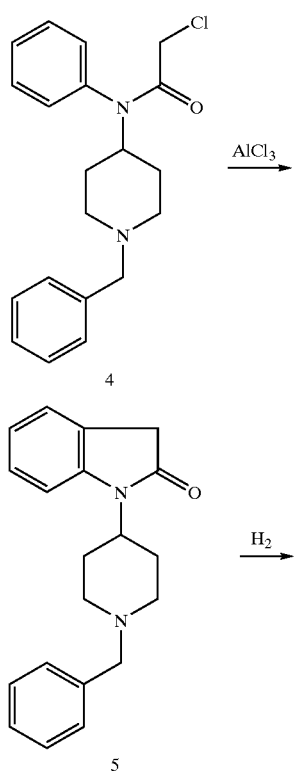

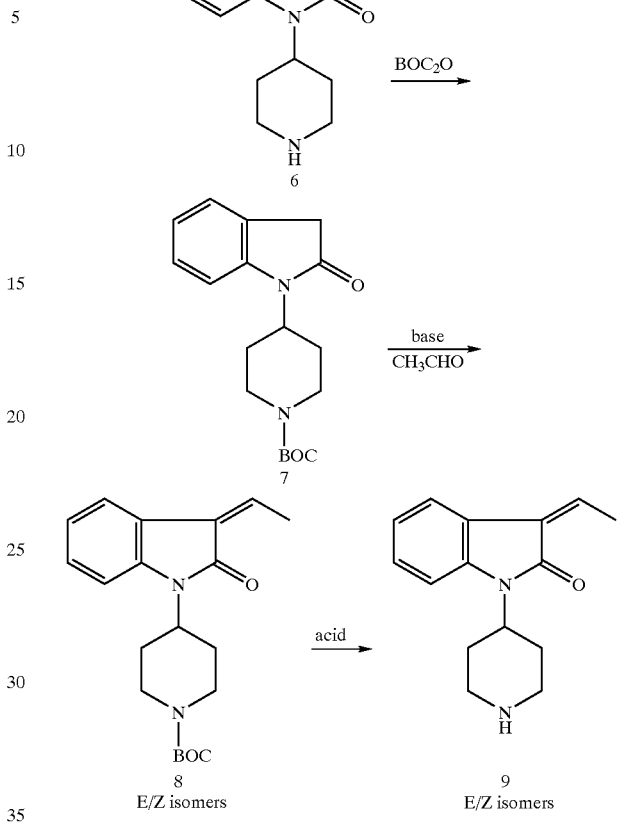

Procedure:

To a mixture of 2 (23.3 g, 0.25 mol), 1 (47.3 g, 0.25 mol), acetic acid (15 g, 0.25 mol) and molecular sieves (15 g) in 500 mL of dichloroethane, sodium triacetoxyborohydride (74.2 g, 0.35 mol) was added in one portion and the mixture stirred overnight. The molecular sieves were filtered off and 1 N NaOH (500 mL) was added to quench the reaction. The organic layer was separated and the aqueous layer extracted with EtOAc (2×300 mL). The combined organic extracts were dried over $K_2CO_3$, filtered and the solvent evaporated under vacuum to give crude 3 as a brown solid which was directly used in next step.

Compound 3

$^1$H—NMR (CDCl$_3$): d 1.50 (m, 2H), 2.05 (m, 2H), 2.20 (bt, 2H), 2.85 (m, 2H), 3.30 (m, 1H), 3.52 (s, 2H), 6.60 (d, 2H), 6.70 (t, 1H), 7.20 (m, 2H), 7.25–7.40 (m, 5H).

To an ice cooled solution of crude 3 (0.25 mol, 100% yield assumed) and DIEA (48.4 g, 0.38 mol) in 500 mL of dichloromethane, was added dropwise chloroacetyl chloride (42.4 g, 0.375 mol). After the addition was complete the ice bath was removed and the reaction mixture stirred overnight. The solvent was removed in vacuum and the residue dissolved in dichloromethane. The organic phase was washed with saturated aqueous $K_2CO_3$, dried over $K_2CO_3$, filtered and the solvent removed in vaccum to give a brown gum which was filtered through a column of silica gel eluting with a mixture of 10% Et$_3$N, 40% EtOAc and 50% hexane. The selected fractions were combined and the solvent evaporated in vacuum to give a brown solid which was further crystallized from EtOAc to give 42.2 g of 4 (49.2%, 2 steps).

Compound 4

$^1$H NMR (DMSO): d 1.22 (m, 2H), 1.70 (b, 2H), 2.00 (t, 2H), 2.80 (b, 2H), 3.40 (s, 2H), 3.80 (s, 2H), 4.40 (m, 1H), 7.15–7.30 (m, 7H), 7.45 (m, 3H).

A mixture of 4 (42.2 g, 0.12 mol) and AlCl$_3$ (49.2 g, 0.369 mol) was mixed in a flask by rapid stirring. The mixture was then heated in an oil bath at 130° C. Within a few minutes the solids melted and became a dark liquid with concomitant gas evolution. After heating for 1 h the reaction mixture was cooled somewhat and while still mobile poured into a beaker containing 500 mL of ice water. The solution was basified and extracted with dichloromethane. The organic layer was dried over Na$_2$SO$_4$, filtered and the solvent evaporated in vacuum to give a dark oil which was filtered through a column of silica gel eluting with a mixture of 10% Et$_3$N, 40% EtOAc and 50% hexane. The selected fractions were combined and the solvent evaporated in vacuum to give 5 as a red oil which set to a pale solid (22.0 g, 58.5%).

Compound 5

$^1$H NMR (CDCl$_3$): d 1.70 (m, 2H), 2.17 (m 2H), 2.50 (m, 2H), 3.05 (m, 2H), 3.55 (s, 2H), 3.60 (s, 2H), 4.33 (m, 1H), 7.00–7.40 (m, 9H).

To a solution of 5 (16.0 g, 0.052 mol) in 35 mL of methanol was added Pd(OH)$_2$ (4.0 g). The resulting suspension was hydrogenated at 50 psi for 12 h at room temperature. The solution was filtered through a pad of Celite and the pad washed with methanol (2×20 mL). Evaporation of the solvent in vacuum gave 6 as a pale solid (11.2 g, 100%).

Compound 6

LC: 100%

MS: m/z 217 (M+1).

$^1$H NMR (CDCl$_3$): d 1.75 (m, 3H), 2.35 (m 2H), 2.75 (m, 2H), 3.25 (m, 2H), 3.50 (s, 2H), 4.33 (m, 1H), 7.00–7.30 (m, 4H)

To a solution of 6 (8.0 g, 37.0 mmol) in 50 mL of dichloromethane was added Et$_3$N (4.07 g, 40.7 mmol) and BOC anhydride (8.87 g, 40.7 mmol). After stirring for 3 h saturated aqueous K$_2$CO$_3$ was added and the layers separated. The aqueous phase was extracted with dichloromethane (2×50 mL). The combined organic phase was dried over K$_2$CO$_3$, filtered and evaporated in vacuum to give a brown oil which was filtered through a column of silica gel eluting with a mixture of 10% Et$_3$N, 40% EtOAc and 50% hexane. The selected fractions were combined and the solvent evaporated in vacuum to give 7 as an off white solid (8.50 g, 73%).

Compound 7

$^1$H NMR (CDCl$_3$): d 1.50 (m, 9H), 1.70 (m 2H), 2.20–2.50 (m, 2H), 2.80–3.00 (m, 2H), 3.50 (s, 2H), 4.20–4.50 (m, 3H), 6.90–7.60 (m, 5H).

To a mixture of 7 (6.0 g, 19.0 mmol) and sodium acetate (2.58 g, 19.0 mmol) in 150 mL of methanol was added acetaldehyde (1.67 g, 38.0 mmol). The mixture was refluxed for 2 h. The solvent was evaporated in vacuum to give a dark oil which was filtered through a column of silica gel eluting with a mixture of 10% Et$_3$N, 40% EtOAc and 50% hexane. The selected fractions were combined and the solvent evaporated in vacuum to give 8 as a red oil (5.90 g, 91%).

Compound 8

LC: 2 isomers in a ratio of 2:1.

$^1$H NMR (CDCl$_3$): (mixture of 2 isomers) d 1.50 (m, 9H), 1.70 (m 2H), 2.20–2.50 (m, 6H), 2.60–3.00 (m, 2H), 4.20–4.50 (m, 3H), 6.90–7.60 (m, 5H).

A solution of 8 (5.90 g, 17.2 mmol) in 30% TFA/dichloromethane (100 mL) was stirred at room temperature for 3 h. The solvent was evaporated in vacuum and saturated aqueous K$_2$CO$_3$ was added to the oily residue. The resulting mixture was extracted with dichloromethane (3×150 mL). The combined organic extracts were dried over K$_2$CO$_3$, filtered and evaporated in vacuum to give the crude product. Chromatography on silica gel eluting with a mixture of 10% Et$_3$N, 50% EtOAc and 40% hexane gave 9 (E/Z isomers) as a yellow foam (3.60 g, 82%).

Compound 9

LC: 2 isomers in a ratio of 2:1.

MS: m/z 243.1 (M+1).

$^1$H NMR (CDCl$_3$): (mixture of 2 isomers) d 0.85 (m, 1H), 1.50–2.00 (m, 4H), 2.20–2.50 (m, 5H), 2.60 (m, 1H), 3.10–3.50 (m, 2H), 4.30 (m, 1H), 6.90–7.60 (m, 5H).

EXAMPLE 5

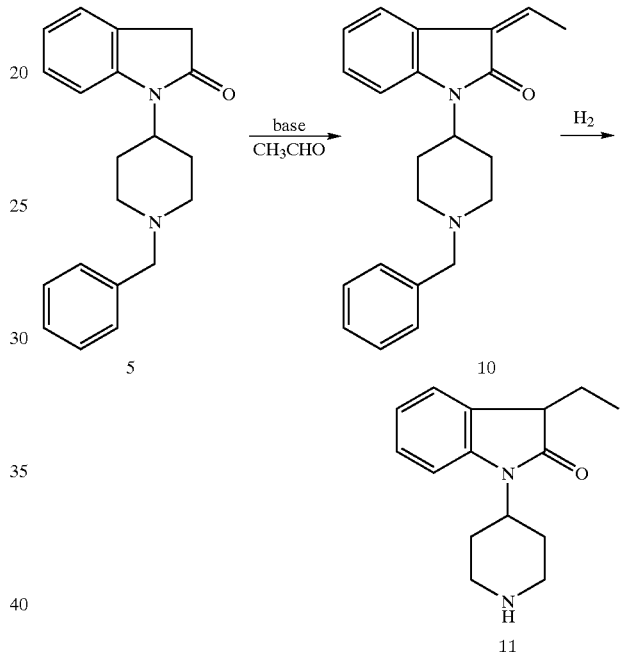

To a mixture of 5 (5.50 g, 18 mmol) and sodium acetate (2.45 g, 18 mmol) in 150 mL of methanol was added acetaldehyde (1.58 g, 36 mmol). The mixture was refluxed for 2 h. The solvent was evaporated in vacuum to give a dark oil which was filtered through a column of silica gel eluting with a mixture of 10% Et$_3$N, 40% EtOAc and 50% hexane. The selected fractions were combined and the solvent evaporated in vacuum to give 10 as a red oil (5.90 g, 98%).

Compound 10

LC: 2 isomers in a ratio of 2:1.

MS: m/z 333.2 (M+1).

$^1$H NMR (CDCl$_3$): d 1.70 (m, 2H), 2.17 (m 2H), 2.30 (d, 3H), 2.50 (m, 2H), 3.05 (m, 2H), 3.55 (s, 2H), 4.33 (m, 1H), 7.00–7.40 (m, 9H), 7.6 (d, 1H).

To a solution of 10 (5.90 g, 17.7 mmol) in 30 mL of methanol was added Pd(OH)$_2$ (3.0 g). The resulting suspension was hydrogenated at 50 psi for 12 h at room temperature. The solution was filtered through a pad of Celite and the pad washed with methanol (2×20 mL). Evaporation of the solvent in vacuum gave a pale solid which was purified by chromatography on silica gel eluting with a mixture of 10% methanol and 90% EtOAc to give 11 as an off white solid (2.02 g, 50%).

Compound 11
  LC: 97%
  MS: m/z 245.2 (M+1)
  ¹H NMR (CDCl₃): d 0.85 (t, 3H), 1.26 (m, 2H), 2.00 (m, 2H), 2.43 (m, 2H), 2.90 (m, 2), 3.3 (m, 2H), 3.4 (m, 1H), 4.4 (m, 1H), 7.05 (m, 1H), 7.15–7.30 (m, 3H).

EXAMPLE 6

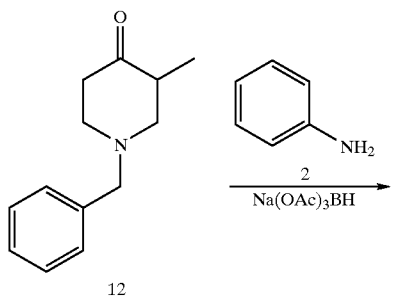

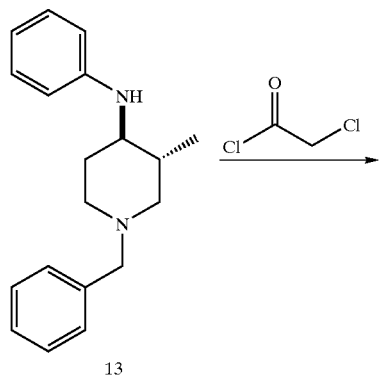

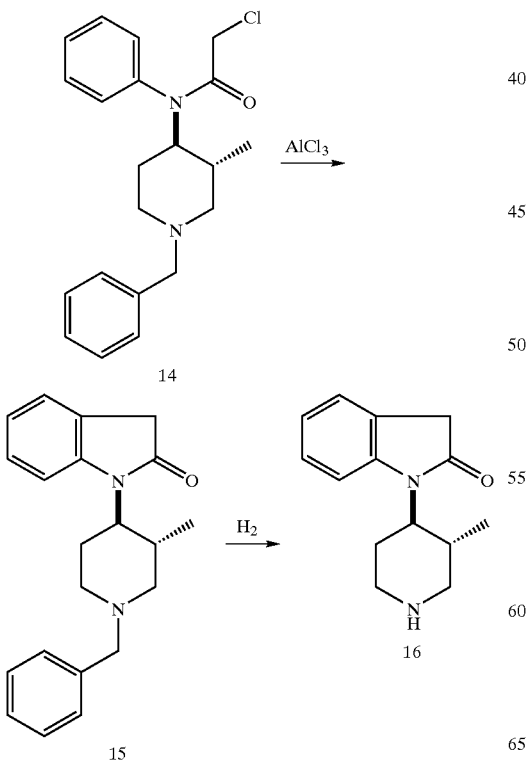

Procedure:
  In a manner similar to the preparation of 6, compound 16 was prepared.

Compound 13
  LC: 89.4%
  MS: m/z 281.2 (M+1)
  ¹H—NMR (mixture of trans and cis) (CDCl₃): d 0.95 (m, 3H), 1.50–2.75 (m, 5H), 2.80–3.20 (m, 1H), 3.50 (m, 2H), 3.60 (minor)+3.70 (major) (two s, 2H), 6.55–6.80 (m, 2H), 7.05–7.45 (m, 8H).

Compound 14
  MS: m/z 357.2 (M+1)
  ¹H—NMR (mixture of trans and cis) (CDCl₃): d 1.10 (m, 3H), 1.40–4.20 (m, 11H), 4.40 (m, 1H), 7.05–7.50 (m, 10H).

Compound 15
  LC: 90.0%
  MS: m/z 321.2 (M+1)
  ¹H—NMR (CDCl₃): d 1.20 (d, 3H), 1.75 (m, 1H), 2.10 (dt, 1H), 2.25 (b, 1H), 2.30 (dd, 1H), 2.75 (dd, 1H), 3.05 (m, 1H), 3.20 (m, 1H), 3.50 (m, 4H), 4.10 (m, 1H), 6.99 (m, 2H), 7.23 (m, 3H), 7.37 (m, 4H).

Compound 16
  LC: 92.5%
  MS: m/z 231.2 (M+1)
  ¹H—NMR (CDCl₃): d d 1.20 (d, 3H), 1.75 (m, 1H), 2.10 (dt, 1H), 2.25 (b, 1H), 2.30 (dd, 1H), 2.75 (dd, 1H), 3.05 (m, 1H), 3.20 (m, 1H), 3.50 (m, 2H), 4.10 (m, 1H), 6.99 (m, 2H), 7.23 (m, 3H), 7.37 (m, 4H).

EXAMPLE 7

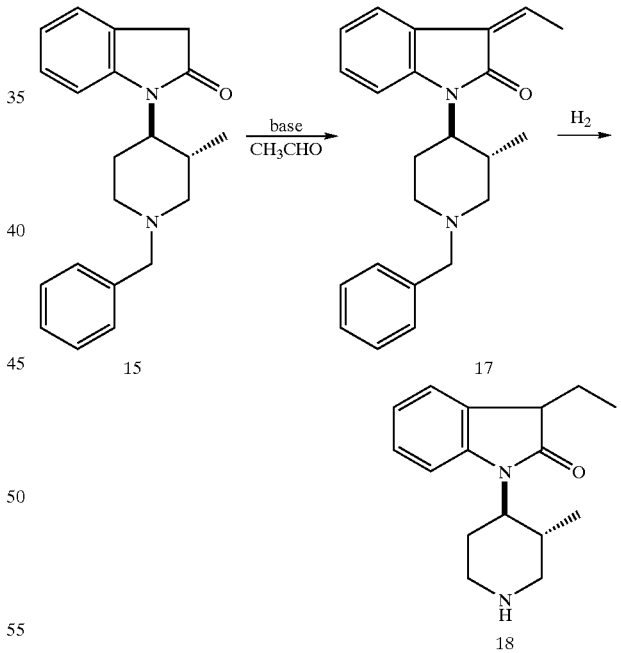

Procedure:
  In a manner similar to the preparation of 11, compound 18 was prepared.

Compound 17
  MS: m/z 347.3 (M+1)

Compound 18
  LC: 82.6%
  MS: m/z 259.3 (M+1)
  ¹H—NMR (CDCl₃): d 0.80 (t, 3H), 1.20 (d, 3H), 2.00 (m, 2H), 2.30 (m, 1H), 2.65 (m, 1H), 2.82 (m, 1H), 3.15–3.25

(m, 1H), 3.32 (m, 1H), 3.45 (m, 1H), 3.65 (m, 1H), 3.75 (m, 1H) 4.25 (m, 1H), 6.90 (d, 1H), 7.05 (t, 1H), 7.25 (m, 2H).

EXAMPLE 8

Attachment of Tail Groups

Tail groups were attached to the head groups according to the following procedures:

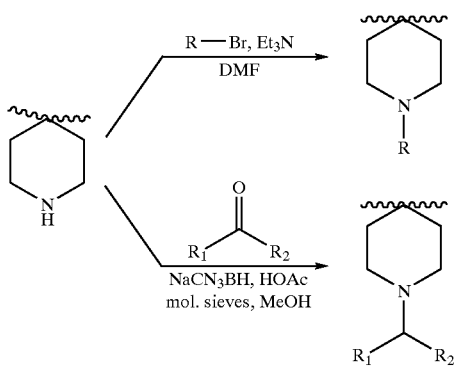

General Procedure for Alkylation:

To a solution of the amine (1 eq) and triethylamine (1 eq) in dimethylformamide, was added 1 eq of alkyl bromide or chloride in one portion. The mixture was stirred and heated at 80° C. over night. TLC indicated the reaction was complete. The reaction was quenched by the addition of water followed by 1 N NaOH to pH 10. The mixture was extracted 2× with $Et_2O$. The combined organic extracts were dried over potassium carbonate and the solvent evaporated, followed by chromatography to give the pure product.

General Procedure for Reductive Amination:

To a mixture of ketone or aldehyde (1 eq), amine (1 eq), and acetic acid (1 eq) in methanol, was added sodium cyanoborohydride (1.4 eq) in one portion. The mixture was stirred over night at room temperature. TLC indicated the reaction was complete. The reaction was quenched by the addition of water followed by 1 N NaOH to pH 10. The mixture was extracted 2× with $Et_2O$. The combined organic extracts were dried over potassium carbonate and the solvent evaporated, followed by chromatography to give the pure product.

The following compounds were prepared by attaching the tail groups using the general procedures described:

1-[1-(naphth-1-yl-methyl)-4-piperidinyl]-1,3-dihydro-2H-indole-2-one
  MS: m/z 357.2 (M+1).
1-[1-(naphth-2-yl-methyl)-4-piperidinyl]-1,3-dihydro-2H-indole-2-one
  MS: m/z 357.3 (M+1).
1-[1-(p-phenylbenzyl)-4-piperidinyl]-1,3-dihydro-2H-indole-2-one
  MS: m/z 383.2 (M+1).
1-[1-(3,3Bis(phenyl)propyl)-4-piperidinyl]-1,3-dihydro-2H-indole-2-one
  LC: 98.7%
  MS: m/z 411.2 (M+1)
  $^1$H—NMR (CDCl$_3$): d 1.65 (bd, 2H), 2.05 (bt, 2H), 2.30 (m, 4H), 2.45 (m, 2H), 3.02 (bd, 2H), 3.50 (s, 2H), 4.01 (t, 1H), 4.30 (m, 1H), 7.00 (t, 1H), 7.15–7.35 (m, 13H).
1-[1-(p-cyanobenzyl)-4-piperidinyl]-1,3-dihydro-2H-indole-2-one
  MS: m/z 332.2 (M+1).
1-[1-(p-benzyloxybenzyl)-4-piperidinyl]-1,3-dihydro-2H-indole-2-one
  MS: m/z 413.3 (M+1)
1-[1-(1,2,3,4-tetrahydronaphth-2-yl)-4-piperidinyl]-1,3-dihydro-2H-indole-2-one
  LC: 100%
  MS: m/z 347.5 (M+1).
  $^1$H NMR (CDCl$_3$): d 1.70 (m, 3H), 2,10 (m, 1H), 2.40 (m, 4H), 2.90–3.00(m, 5H), 3.10 (m, 2H), 3.60 (s, 2H), 4.3 (m, 1H), 7.00–7.30 (m, 8H).
1-[1-(5-methylhex-2-yl)-4-piperidinyl]-1,3-dihydro-2H-indole-2-one
  LC: 100%,
  MS: m/z 315.4 (M+1).
  $^1$H NMR (CDCl$_3$): d 0.90 (m, 6H), 1.00 (m, 3H), 1.20 (m, 3H), 1.5–1.8 (m, 2H), 2.2–2.6 (m, 5H), 2.90 (m, 2H), 3.60 (s, 2H), 4.2 (m, 1H), 6.90–7.30 (m, 4H).
1-[1-(norbornan-2-yl)-4-piperidinyl]-1,3-dihydro-2H-indole-2-one
  LC: 97%
  MS: m/z 311.41 (M+1).
  $^1$H NMR (CDCl$_3$): d 0.90 (m, 1H), 1.30–2.00(m, 7H), 2.10–2.30 (m, 5H), 3.20 (m, 2H), 3.60 (s, 2H), 4.3 (m, 1H), 6.90–7.30 (m, 4H).
1-[1-(1,3-dihydroinden-2-yl)-4-piperidinyl]-1,3-dihydro-2H-indole-2-one
  LC: 100%
  MS: m/z 332.4 (M+1).
  $^1$H NMR (CDCl$_3$): d 1.80 (m, 2H), 2,40 (m, 2H), 2.50 (m, 2H), 2.90 (m, 2H), 3.10–3,40 (m, 5H), 3.60 (s, 2H), 4.20 (m, 1H), 7.10–7.30 (m, 8H).
1-[1-(cycooctylmethyl)-4-piperidinyl]-1,3-dihydro-2H-indole-2-one
  LC: 97%
  MS: m/z 341.50 (M+1).
  $^1$H NMR (CDCl$_3$): d 1.25 (m, 3H), 1–4–1.7 (m, 14H), 2.10 (m, 4H), 2.50(m, 2H), 3.10 (m, 2H), 3.60 (s, 2H), 4.3 (m, 1H), 7.10–7.20 (m, 4H).
  $^{13}$C—NMR (CDCl$_3$): d 23.07, 26.04,26.89,27.56, 28.63, 31.27,32.00, 35.30,36.33,46.63, 50.65, 54.06, 66.47, 110.90, 122.17, 124.90, 125.26, 127.94, 144.25, 175.31.
3-ethyl-1-[1-(1,2,3,4-tetrahydro-2-naphthyl)-4-piperidinyl]-1,3-dihydro-2H-indole-2-one
  MS: m/z 375.3 (M+1).
3-ethyl-1-[1-(4-propylcyclohexyl)-4-piperidinyl]-1,3-dihydro-2H-indole-2-one
  MS: m/z 369.2 (M+1).
3-ethyl-1-[1-(5-methylhex-2-yl)-4-piperidinyl]-1,3-dihydro-2H-indole-2-one
  LC: 100%
  MS: m/z 342.4 (M+1).
  $^1$H NMR (CDCl$_3$): d 0.80 (t, 3H), 0.90 (m, 6H), 1.00 (m, 3H), 1.20 (m, 3H), 1.5–1.8 (m, 2H), 2.2–2.6 (m, 5H), 2.90 (m, 2H), 3.40 (m, 1H), 4.3 (m, 1H), 6.90–7.30 (m, 4H).
3-ethyl-1-[1-(norbornan-2-yl)-4-piperidinyl]-1,3-dihydro-2H-indole-2-one
  LC: 100%
  MS: m/z 339.41 (M+1).
  $^1$H NMR (CDCl$_3$): d 0.80 (m,3H),0.90 (m, 1H),1.30–1.45 (m,5H),1.50–2.05 (m,8H), 2.10 (m, 1H), 2.20 (m, 2H), 2.50 (m, 2H), 3.10 (m, 2H), 3.40 (m,1H), 4.3 (m, 1H), 6.90–7.30 (m, 4H).
3-ethyl-1-[1-(decahydro-2-naphthyl)-4-piperidinyl]-1,3-dihydro-2H-indole-2-one
  MS: m/z 381.3 (M+1).
3-ethyl-1-[1-[4-(1-methylethyl)-cyclohexyl]-4-piperidinyl]-1,3-dihydro-2H-indole-2-one
  MS: m/z 369.3 (M+1)
  $^1$H—NMR (CDCl$_3$): d 0.88 (t, 3H), 0.92 (d, 6H), 1.17 (m, 1H), 1.40 (m, 2H), 1.50–1.70 (m, 9H), 2.05 (m, 2H), 2.25

(m, 2H), 2.32–2.55 (m, 3H), 3.15 (b, 2H), 3.43 (t, 1H), 4.35 (m, 1H), 7.05 (t, 1H), 7.22 (d, 1H), 7.28 (m, 2H).

3-ethyl-1-[1-(1,3-dihydroinden-2-yl)-4-piperidinyl]-1,3-dihydro-2H-indole-2-one
MS: m/z 361.2 (M+1).

3-ethyl-1-[1-(cyclooctylmethyl)-4-piperidinyl]-1,3-dihydro-2H-indole-2-one
LC: 97%
MS: m/z 369.50 (M+1).
$^1$H NMR (CDCl$_3$): d 0.80 (t, 3H), 1.25 (m, 3H), 1–4–1.7 (m, 14H), 2.10 (m, 6H), 2.50 (m, 2H), 33.10 (m, 2H), 3.40 (m, 1H), 4.3 (m, 1H), 7.10–7.20 (m, 4H).

3-ethylidene-1-[1-(benzyl)-4-piperidinyl]-1,3-dihydro-2H-indole-2-one
MS: m/z 333.2 (M+1)
$^1$H—NMR (CDCl$_3$): d 1.70 (m, 2H), 2.15 (dt, 2H), 2.28 (d, 3H), 2.47 (m, 2H), 3.05 (b, 2H), 3.57 (s, 2H), 4.34 (m, 1H), 7.02 (t, 1H), 7.08–7.40 (m, 8H), 7.58 (d, 1H).

3-ethylidene-1-[1-(naphth-2-yl-methyl)-4-piperidinyl]-1,3-dihydro-2H-indole-2-one
MS: m/z 405.2

3-ethylidene-1-[1-(3,3-diphenylpropyl)-4-piperidinyl]-1,3-dihydro-2H-indole-2-one
LC: >97% (2 isomers combined).
MS: m/z 437.5 (M+1).
$^1$H NMR (CDCl$_3$): d 1.70–1.80 (m, 3H), 2,10 (m, 2H), 2.20–2.40 (m, 8H), 3.10 (m, 2H), 4.10 (M, 1H), 4.3 (m, 1H), 7.00–7.30 (m, 15H).

3-ethylidene-1-[1-(p-cyanobenzyl)-4-piperidinyl]-1,3-dihydro-2H-indole-2-one
LC: >97% (2 isomers combined).
MS: m/z 358.5 (M+1).
$^1$H NMR (CDCl$_3$): d 1.80(m, 4H),2.10–2.60 (m, 5H), 3.10 (m, 2H), 3.70 s, 2H), 4.3 (m, 1H), 6.90–7.60 (m, 8H).

3-ethylidene-1-[1-(p-benzyloxybenzyl)-4-piperidinyl]-1,3-dihydro-2H-indole-2-one
MS: m/z 405.2.

3-ethylidene-1-[1-(1,2,3,4-tetrahydro-2-naphthyl)-4-piperidinyl]-1,3-dihydro-2H-indole-2-one
LC: >97% (2 isomers combined).
MS: m/z 373.5 (M+1).
$^1$H NMR (CDCl$_3$): d 1.70–3.10 (m, 18H), 4.3 (m, 1H), 7.00–7.30 (m, 9H).

3-ethylidene-1-[1-(4-propylcyclohexyl)-4-piperidinyl]-1,3-dihydro-2H-indole-2-one
LC: >97% (2 isomers combined).
MS: m/z 367.5 (M+1).
$^1$H NMR (CDCl$_3$): d 0.90 (m, 1H), 1.30–2.00(m, 7H), 2.10–2.30 (m, 5H), 3.20 (m, 2H), 3.60 (s, 2H), 4.3 (m, 1H), 6.90–7.30 (m, 5H).

3-ethylidene-1-[1-(5-methylhex-2-yl)-4-piperidinyl]-1,3-dihydro-2H-indole-2-one
LC: >97% (2 isomers combined).
MS: m/z 341.4 (M+1).
$^1$H NMR (CDCl$_3$): d 0.90–2.6 (m, 24H), 2.90 (m, 2H), 4.2 (m, 1H), 6.90–7.30 (m, 5H).

3-ethylidene-1-[1-(norbornan-2-yl)-4-piperidinyl]-1,3-dihydro-2H-indole-2-one
LC: >97% (2 isomers combined).
MS: m/z 337.41 (M+1).
$^1$H NMR (CDCl$_3$): d 0.90 (m, 1H), 1.30–2.50(m, 17H), 3.10 (m, 2H), 4.3 (m, 1H), 6.90–7.30 (m, 5H).

3-ethylidene-1-[1-(1,3-dihydroinden-2-yl)-4-piperidinyl]-1,3-dihydro-2H-indole-2-one
LC: >97% (2 isomers combined).
MS: m/z 359.4 (M+1).
$^1$H NMR (CDCl$_3$): d 1.80–3.10 (m, 17H), 4.20 (m, 1H), 7.10–7.30 (m, 9H).

3-ethylidene-1-[1-(cyclooctylmethyl)-4-piperidinyl]-1,3-dihydro-2H-indole-2-one
LC: >97% (2 isomers combined).
MS: m/z 367.50 (M+1).
$^1$H NMR (CDCl$_3$): d 1.25 (m, 3H), 1.4–1.7 (m, 21H), 2.10–2.50(m, 2H), 3.10 (m, 2H), 4.3 (m, 1H), 6.90–7.60 (m, 5H).

1-[1-(3,3-Bis(phenyl)propyl)-3-(methyl)-4-piperidinyl]-1,3-dihydro-2H-indole-2-one
LC: 100%
MS: m/z 425.3 (M+1)
$^1$H—NMR (CDCl$_3$): d 1.20 (d,3H), 1.69 (bd, 1H), 1.95 (dt, 1H),2.13–2.30 (m,5H), 2.72 (bd, 1H), 2.98 (bd, 1H), 3.15 (dq, 1H), 3.50 (s, 2H), 4.03 (dt, 1H), 4.12 (t, 1H), 6.94 (d, 1H), 7.00 (t, 1H), 7.10–7.30 (m, 12H).

1-[1-(benzyl)-3-(methyl)-4-piperidinyl]-1,3-dihydro-2H-indole-2-one
LC: 100%
MS: m/z 321.2 (M+1)
$^1$H—NMR (CDCl$_3$): d 1.20 (d,3H), 1.70 (m, 1H), 2.10 (dt, 1H), 2.23 (m, 1H), 2.35 (dd, 1H), 2.78 (d, 1H), 3.05 (m, 1H), 3.20 (dq, 1H), 3.51 (m, 4H), 4.10 (dt, 1H), 7.00 (m, 2H), 7.25 (m, 3H), 7.38 (m, 4H).

1-[1-(4-propyl-cyclohexyl)-3-(methyl)-4-piperidinyl]-1,3-dihydro-2H-indole-2-one
LC: 96.2%
MS: m/z 355.2 (M+1)
$^1$H—NMR (CDCl$_3$): d 0.85 (m, 3H), 1.15 (m, 3H), 1.22–1.85 (m, 13H), 2.05–2.90 (m, 6H), 2.95–3.20 (m, 2H), 3.50 (s, 2H), 4.05 (m, 1H), 7.00 (m, 2H), 7.22 (m, 2H).

1-[1-(5-methylhex-2-yl)-3-(methyl)-4-piperidinyl]-1,3-dihydro-2H-indole-2-one
LC: 100%
MS: m/z 329.2 (M+1)
$^1$H—NMR (CDCl$_3$): d 0.85 (m,9H), 1.15 (m, 3H), 1.20–1.75 (m, 6H), 2.25 (m, 1H),2.45–2.75 (m, 4H), 2.88 (m, 1H), 3.10 (m, 1H), 3.50 (s, 2H), 4.05 (m, 1H), 6.98 (m, 2H), 7.25 (m, 2H).

1-[1-(decahydro-2-naphthyl)-3-(methyl)-4-piperidinyl]-1,3-dihydro-2H-indole-2-one
LC: 95.3%
MS: m/z 367.2 (M+1)
$^1$H—NMR (CDCl$_3$): d 1.11 (d,3H), 1.16–1.85 (m, 16H), 2.20 (m, 1H),2.35 (m,2H),2.52 (m, 2H), 2.75 (m, 1H), 3.02 (m, 2H), 3.50 (s, 2H), 4.05 (m, 1H), 6.96 (m, 2H), 7.20 (m, 2H).

1-[1-(4-(1-methylethyl)-cyclohexyl)-3-(methyl)-4-piperidinyl]-1,3-dihydro-2H-indole-2-one
LC: 96.1%
MS: m/z 355.2 (M+1)
$^1$H—NMR (CDCl$_3$): d 0.80 (m, 6H), 1.15 (m, 3H), 1.22–1.48 (m, 3H), 1.50–1.90 (m, 6H), 2.15–2.90 (m, 4H), 2.95–3.25 (m, 2H), 3.50 (s, 2H), 4.10 (m, 1H), 6.95 (m, 2H), 7.22 (m, 2H).

1-[1-(cyclooctylmethyl)-3-(methyl)-4-piperidinyl]-1,3-dihydro-2H-indole-2-one
LC: 100%
MS: m/z 355.2 (M+1)
$^1$H—NMR (CDCl$_3$): d 1.12 (d,3H),1.15–1.75 (m, 16H), 1.92–2.10 (m,3H), 2.20 (m, 2H) 2.73 (m, 1H), 3.00 (m, 1H), 3.12 (dq, 1H), 3.50 (s, 2H), 4.05 (dt, 1H), 6.99 (m, 2H), 7.20 (m, 2H).

3-ethyl-1-[1-(3,3-Bis(phenyl)propyl)-3-(methyl)-4-piperidinyl]-1,3-dihydro-2H-indole-2-one
LC: 96.3%
MS: m/z 453.3 (M+1)
$^1$H—NMR (CDCl$_3$): d (two t, 3H), 1.18 (d, 3H), 1.70 (m, 1H), 1.90–2.05 (m, 3H), 2.12–2.30 (m, 5H), 7.73 (m, 1H), 2.97 (bd, 1H), 3.10–3.30 (m, 1H), 3.38 (t, 1H), 3.90–4.05 (m, 1H), 4.12 (q, 1H), 6.90–7.00 (two d, 1H), 7.02 (t, 1H), 7.12–7.32 (m, 12H).

3-ethyl-1-[1-(4-propylcyclohexyl)-3-(methyl)-4-piperidinyl]-1,3-dihydro-2H-indole-2-one
LC: 93.2%
MS: m/z 383.3 (M+1)
$^1$H—NMR (CDCl$_3$): d 0.75–0.95 (m, 6H), 1.05–1.20 (m, 5H), 1.20–1.35 (m, 4H), 1.35–1.75 (m, 6H), 1.75–1.90 (m, 2H), 1.95–2.05 (m, 2H), 2.15–2.45 (m, 3H), 2.55 (d, 0.5H), 2.75 (d, 0.5H), 2.95–3.15 (m, 2H), 3.38 (t, 1H), 3.90–4.10 (m, 1H), 6.90–7.05 (2H), 7.20–7.25 (d, 2H).

3-ethyl-1-[1-(5-methylhex-2-yl)-3-(methyl)-4-piperidinyl]-1,3-dihydro-2H-indole-2-one;
LC: 92.3%
MS: m/z 357.4 (M+1)
$^1$H—NMR (CDCl$_3$): d 0.75–0.95 (m, 10H), 1.10 (d, 3H), 1.15–1.40 (m, 3H), 1.40–1.75 (m, 4H), 1.97–2.10 (m, 2H), 2.20 (m, 1H), 2.43–2.75 (m, 4H), 2.80–2.95 (m, 1H), 3.00–3.25 (m, 1H), 3.40 (t, 1H), 3.90–4.10 (m, 1H), 6.90–7.05 (m, 2H), 7.25 (m, 2H).

3-ethyl-1-[1-[4-(1-methylethyl)cyclohexyl]-3-methyl-4-piperidinyl]-1,3-dihydro-2H-indole-2-one
LC: 94.7%
MS: m/z 383.4 (M+1)
$^1$H—NMR (CDCl$_3$): d 0.75–1.05 (m, 8H), 1.10–1.50 (m, 7H), 1.50–1.90 (m, 7H), 1.90–2.20 (m, 2H), 2.15–2.43 (m, 3H), 2.55 (d, 0.5H), 2.75 (d, 0.5H), 2.90–3.25 (m,3H), 3.40 (t, 1H), 3.90–4.10 (m, 1H), 6.90–7.01 (m, 2H), 7.25 (m, 2H).

3-ethyl-1-[1-(decahydro-2-naphthyl)-3-(methyl)-4-piperidinyl]-1,3-dihydro-2H-indole-2-one
LC: 94.3%
MS: m/z 395.3 (M+1)
$^1$H—NMR (CDCl$_3$): d 1.75–1.90 (two t, 3H),1.10 (d, 3H), 1.15–1.90 (m, 15H), 2.00 (m, 2H), 2.20 (bs, 1H), 2.40 (m, 2H), 2.45–2.60 (m, 2H), 2.75 (m, 1H), 2.90–3.20 (m, 2H), 3.40 (bs, 1H), 3.90–4.15 (m, 1H), 6.90–7.05 (m, 2H), 7.25 (m, 2H).

Other compounds within the scope of formula (II) or (IIA) of the present invention can be synthesized by analogous techniques.

EXAMPLE 9

Nociceptin affinity at the ORL1 receptor for preferred compounds was obtained using the following assay:

Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 ml/10 cm dish) followed by homogenization with a tissue grinder/teflon pestle. Membranes were collected by centrifugation at 30,000×g for 15 min at 4° C. and pellets resuspended in hypotonic buffer to a final concentration of 1–3 mg/ml. Protein concentrations were determined using the BioRad protein assay reagent with bovine serum albumen as standard. Aliquots of the ORL-1 receptor membranes were stored at −80° C.

Functional SGTPgS binding assays were conducted as follows. ORL-1 membrane solution was prepared by sequentially adding final concentrations of 0.066 mg/ml ORL-1 membrane protein, 10 mg/ml saponin, 3 mM GDP and 0.20 nM [$^{35}$S]GTPgS to binding buffer (100 mM NaCl, 10 mM MgCl$_2$, 20 mM HEPES, pH 7.4) on ice. The prepared membrane solution (190 ml/well) was transferred to 96-shallow well polypropylene plates containing 10 ml of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 200 ml ice-cold binding buffer (10 mM NaH$_2$PO$_4$, 10 mM Na$_2$HPO$_4$, pH 7.4). Filter plates were subsequently dried at 50° C. for 2–3 hours. Fifty ml/well scintillation cocktail (BetaScint; Wallac) was added and plates were counted in a Packard Top-Count for 1 min/well.

Data was analyzed using the curve fitting functions in GraphPad PRISMÔ, v. 3.0 and the results are set forth in table 2 below:

TABLE 2

Nociceptin Affinity

| Compound | calc K$_i$ (nM) |
| --- | --- |
| 3-ethylidene-1-[1-(5-methylhex-2-yl)-4-piperidinyl]-1,3-dihydro-2H-indole-2-one | 11.1 |
| 3-ethylidene-1-[1-(4-propylcyclohexyl)-4-piperidinyl]-1,3-dihydro-2H-indole-2-one | 19 |
| 3-ethylidene-1-[1-(1,2,3,4-tetrahydro-2-naphthyl)-4-piperidinyl]-1,3-dihydro-2H-indole-2-one | 16.7 |
| 3-ethylidene-1-[1-(1,3-dihydroinden-2-yl)-4-piperidinyl]-1,3-dihydro-2H-indole-2-one | 20.7 |
| 3-ethylidene-1-[1-(naphth-2-yl-methyl)-4-piperidinyl]-1,3-dihydro-2H-indole-2-one | 630 |
| 3-ethylidene-1-[1-(p-benzyloxybenzyl)-4-piperidinyl]-1,3-dihydro-2H-indole-2-one | 516 |
| 3-ethylidene-1-[1-(benzyl)-4-piperidinyl]-1,3-dihydro-2H-indole-2-one | 1854 |
| 3-ethylidene-1-[1-(cyclooctylmethyl)-4-piperidinyl]-1,3-dihydro-2H-indole-2-one | 22.3 |
| 3-ethylidene-1-[1-(3,3-diphenylpropyl)-4-piperidinyl]-1,3-dihydro-2H-indole-2-one | 100.7 |
| 3-ethylidene-1-[1-(norbornan-2-yl)-4-piperidinyl]-1,3-dihydro-2H-indole-2-one | 922 |
| 3-ethylidene-1-[1-(p-cyanobenzyl)-4-piperidinyl]-1,3-dihydro-2H-indole-2-one | 7652 |
| 3-ethyl-1-[1-(5-methylhex-2-yl)]-4-piperidinyl]-1,3-dihydro-2H-indole-2-one | 4 |
| 3-ethyl-1-[1-[4-(1-methylethyl)-cyclohexyl]-4-piperidinyl]-1,3-dihydro-2H-indole-2-one | .86 |
| 3-ethyl-1-[1-(4-propylcyclohexyl)-4-piperidinyl]-1,3-dihydro-2H-indole-2-one | 40 |
| 3-ethyl-1-[1-(1,2,3,4-tetrahydro-2-naphthyl)-4-piperidinyl]-1,3-dihydro-2H-indole-2-one | 124 |
| 3-ethyl-1-[1-(decahydro-2-naphthyl)-4-piperidinyl]-1,3-dihydro-2H-indole-2-one | 3.6 |
| 3-ethyl-1-[1-(1,3-dihydroinden-2-yl)-4-piperidinyl]-1,3-dihydro-2H-indole-2-one | 43 |
| 3-ethyl-1-[1-(cyclooctylmethyl)-4-piperidinyl]-1,3-dihydro-2H-indole-2-one | 9 |
| 3-ethyl-1-[1-(norbornan-2-yl)-4-piperidinyl]-1,3-dihydro-2H-indole-2-one | 82.7 |
| 1-[1-(naphth-1-ylmethyl)-4-piperidinyl]-1,3-dihydro-2H-indole-2-one | 92 |
| 1-[1-(naphth-2-yl-methyl)-4-piperidinyl]-1,3-dihydro-2H-indole-2-one | 107 |
| 1-[1-(p-phenylbenzyl)-4-piperidinyl]-1,3-dihydro-2H-indole-2-one | 1362 |
| 1-[1-(3,3-Bis(phenyl)propyl)-4-piperidinyl]-1,3-dihydro-2H-indole-2-one | 12.5 |
| 1-[1-(p-cyanobenzyl)-4-piperidinyl]-1,3-dihydro-2H-indole-2-one | 1267 |
| 1-[1-(p-benzyloxybenzyl)-4-piperidinyl]-1,3-dihydro-2H-indole-2-one | 32 |
| 1-[1-(1,2,3,4-tetrahydronaphth-2-yl)-4-piperidinyl]-1,3-dihydro-2H-indole-2-one | 28.7 |
| 1-[1-(5-methylhex-2-yl)-4-piperidinyl]-1,3-dihydro-2H-indole-2-one | 7.4 |
| 1-[1-(norbornan-2-yl)-4-piperidinyl]-1,3-dihydro-2H-indole-2-one | 215 |
| 1-[1-(1,3-dihydroinden-2-yl)-4-piperidinyl]-1,3-dihydro-2H-indole-2-one | 18.7 |

TABLE 2-continued

Nociceptin Affinity

| Compound | calc $K_i$ (nM) |
|---|---|
| 1-[1-(cycooctylmethyl)-4-piperidinyl]-1,3-dihydro-2H-indole-2-one | 54.3 |
| 1-[1-(benzyl)-3-(methyl)-4-piperidinyl]-1,3-dihydro-2H-indole-2-one | >10,000 |
| 1-[1-(4-propyl-cyclohexyl)-3-methyl-4-piperidinyl]-1,3-dihydro-2H-indole-2-one | 2435 |
| 1-[1-(5-methylhex-2-yl)-3-(methyl)-4-piperidinyl]-1,3-dihydro-2H-indole-2-one | 4335 |
| 1-[1-(decahydro-2-naphthyl)-3-(methyl)-4-piperidinyl]-1,3-dihydro-2H-indole-2-one | 366 |
| 1-[1-(4-(1-methylethyl)-cyclohexyl)-3-(methyl)-4-piperidinyl]-1,3-dihydro-2H-indole-2-one | 167 |
| 1-[1-(cyclooctylmethyl)-3-(methyl)-4-piperidinyl]-1,3-dihydro-2H-indole-2-one | 189 |

EXAMPLE 10

Synthesis of Certain Head Groups

SCHEME 1:

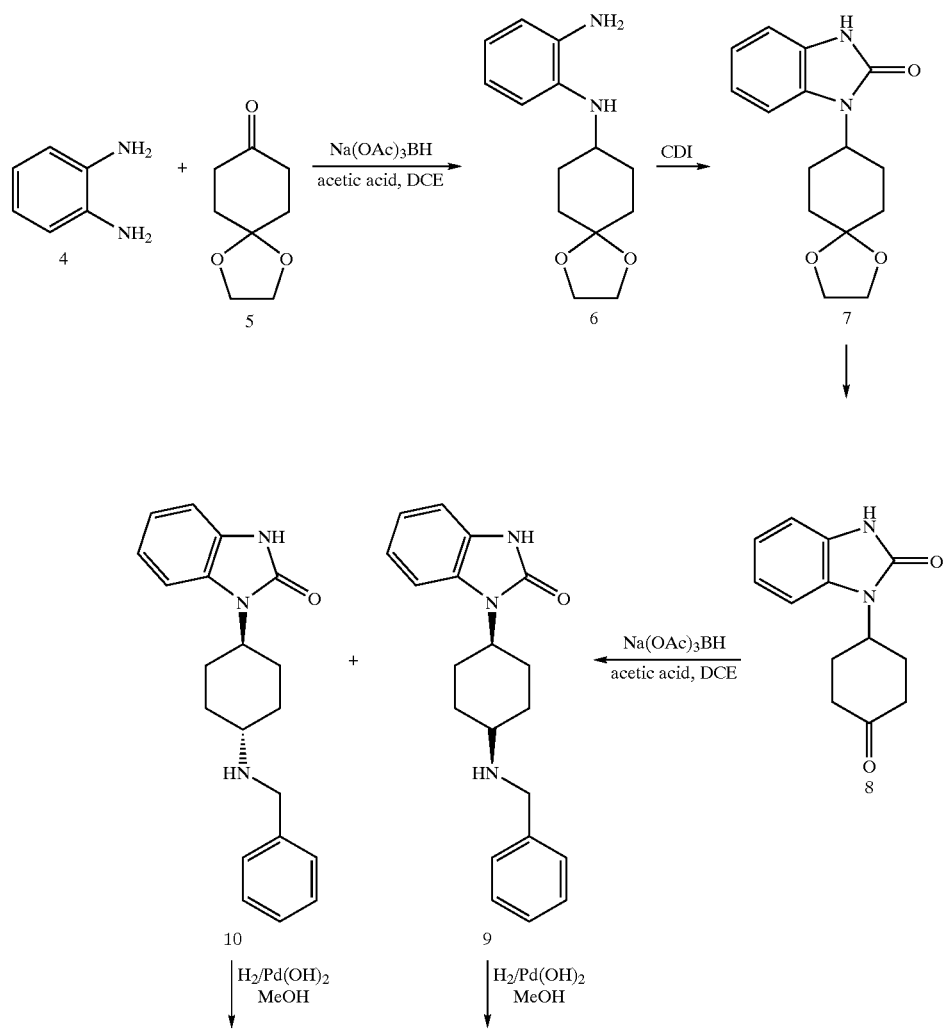

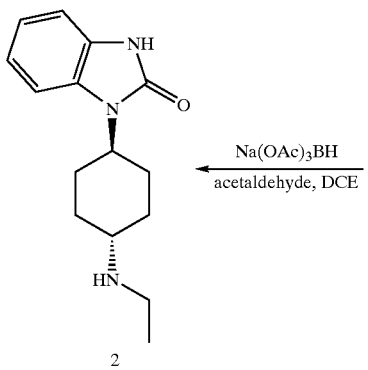 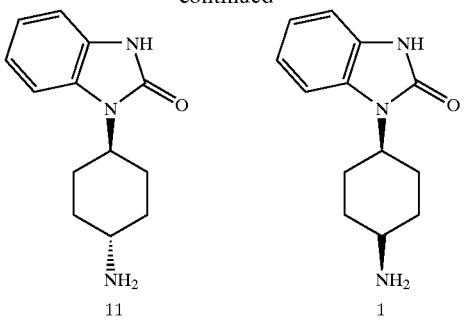

Procedure:

To a mixture of 4 (21.6 g, 0.2 mole), 5 (15.6 g, 0.1 mole), acetic acid (6 g, 0.1mole) in 500 ml of dichloroethane, 29.7 g of sodium triacetoxyborohydride (0.14 mol, 1.4 eq) was added in one portion. Gas evolves between 30 min and 1 hr. The mixture was stirred over night. TLC indicated the reaction is complete. 1 N NaOH (500 ml) was added to quench the reaction. The organic layer was separated and the aqueous layer was extracted by EtOAC (300 ml×2). The combined organics were dried over potassium carbonate and the solvent evaporated to give a red oil which was column filtrated (5% Et3N, 25% EtOAc and 70% Hexane) to give 14 g of product 6 as a white solid (54%).

Compound 6

MS: m/z 249.3 (M+1).

$^1$H NMR (CDCl$_3$): d 1.50–1.90 (m, 6H), 2.05 (m, 2H), 3.30 (m, 4H), 3.95 (s, 4H), 6.60–6.80 (m, 4H).

To a solution of 13.5 g of 6 (54.4 mmol) in 50 ml of acetonitrile, 11.02 g of carbonyldiimidazole was added in one portion. The mixture was stirred over night. Solid 4z precipitated out of solution which was filtered and washed by H$_2$O and TBME to give 7.5 g of product. The filtrate was evaporated and the crude material was dissolved in EtOAc, washed with water and saturated potassium carbonate solution. The organics were dried over potassium carbonate. The solvent was evaporated to give a second batch of solid with a pink color which was column filtrated (10% Et3N, 40% EtOAc and 50% Hexane) to give another 4.5 g of product 7 (81%, combined).

Compound 7

MS: m/z 274.7 (M+1).

$^1$H NMR (CDCl$_3$): d 1.50–1.90 (m, 7H), 2.50 (m, 2H), 4.00 (m, 4H), 4.50 (m, 1H), 7.10 (m, 3H), 7.25 (m, 1H).

A mixture of 7 (7.5 g, 27.4 mmole) and 8.26 g of PPTS in 50 ml of acetone and H$_2$O (10:1) was stirred in refluxed over night. The mixture was cooled to room temperature and acetone was evaporated. Addition of water to the mixture initiated crystalization to give 3 g of product 8 (47.4%).

Compound 8

MS: m/z 231 (M+1).

$^1$H NMR (CDCl$_3$): d 2.20 (m, 2H), 2.60 (m, 2H), 4.50 (m, 1H), 7.10 (m, 4H), 9.5 (br, 1H).

To a mixture of 8 (7.75 g, 33.65 mmole), benzylamine (3.61 g, 33.65 mmole), acetic acid (2.0 g, 33.65 mmole) in 150 ml of dichloroethane, 10.3 g of sodium triacetoxyborohydride (47.1 mmol, 1.4 eq) was added in one portion. Gas evolves between 30 min and 1 hr. The mixture was stirred over night. TLC indicated the reaction was complete. 1 N NaOH (500 ml) was added to quench the reaction. The organic layer was separated and the aqueous layer was extracted with EtOAc (300 ml×2). The combined organics were dried over potassium carbonate and the solvent was evaporated to give a brown solid, which was column filtrated (5% Et3N, 25% EtOAc and 70% Hexane to 10% Et3N, 40% EtOAc and 50% Hexane) to give 4.7 g of product 10 as a white solid (53.4%) and 3.01 g of product 9 as a white solid (34.2%).

Compound 9

MS: m/z 322 (M+1).

$^1$H NMR (CDCl$_3$): d 1.40 (m, 2H), 1.80–2.35 (m, 6H), 2.70 (m, 1H), 3.86 (s, 2H), 4.30 (m, 1H), 7.10–7.50 (m, 9H), 9.6 (br, 1H).

Compound 10

MS: m/z 322 (M+1).

$^1$H NMR (CDCl$_3$): d 1.60 (m, 4H), 1.90 (m, 2H), 2.60 (m, 2H), 3,10 (m, 1H), 3.84 (s, 2H), 4.50 (m, 1H), 7.10–7.50 (m, 9H), 9.6 (br, 1H).

2 g of Pd(OH)2 was added into a solution of 30 ml of methanol containing 4.7 g of compound 10. The resulting suspension was hydrogenated at 50 psi for 12 hrs at room temperature. TLC indicated the reaction was complete over night. The solution was filtered through a pad of celite to remove the catalyst. The celite was washed with methanol twice (20 ml). The organics were combined and solvent was removed to give a pale solid which was purified by chromatography (10% MeOH, 90% EtOAc) to give an off white product 11 (1.79 g, 50.7%).

Compound 11

MS: m/z 232 (M+1).

$^1$H NMR (CDCl$_3$): d 1.50–1.85 (m, 8H), 2.60 (m, 2H), 4.30 (m, 1H), 7.10 (m, 3H), 7.30 (m, 1H).

To a mixture of 11 (1.7 g, 7.4 mmole), acetaldehyde (0.33 g, 7.4 mmole) in 50 ml of dichloroethane, 2.2 g of sodium triacetoxyborohydride (10.36 mmol, 1.4 eq) was added in one portion. Gas evolves between 30 min and 1 hr. The mixture was stirred over night. TLC indicated the reaction was complete. 1 N NaOH (500 ml) was added to quench the reaction. The organic layer was separated and the aqueous layer was extracted with EtOAc (300 ml×2). The combined organics were dried over potassium carbonate and the solvent was evaporated to give a brown oil which was chromatographed (10% Et3N, 40% EtOAc and 50% Hexane) to give 1.5 g of product 2 as a sticky oil which recrystalized from TBME to give a white solid (78%).

Compound 2

MS: m/z 259.7 (M+1).

$^1$H NMR (CDCl$_3$): d 1.15 (t, 3H), 1.50–1.95 (m, 6H), 2.40–2.75 (m, 4H), 2.95 (m, 1H), 4.35 (m; 1H), 7.10 (m, 3H), 7.35 (m, 1H).

1.5 g of Pd(OH)$_2$ was added into a solution of 30 ml of methanol containing 3.01 g of compound 9. The resulting suspension was hydrogenated at 50 psi for 12 hrs at room temperature. TLC indicated the reaction was complete over night. The solution was filtered through a pad of celite to remove the catalyst. The celite was washed with methanol twice (20 ml). The organics were combined and solvent was removed to give a pale solid which was purified by chromatography (10% MeOH, 90% EtOAc) to give an off white product 1 (1.68 g, 77.4%).

Compound 1

MS: m/z 232(M+1).

$^1$H NMR (CDCl$_3$): d 1.50 (m,2H), 1.90–2.35 (m, 6H), 3.00 (m, 1H), 4.30 (m, 1H), 7.10–7.30 (m, 4H).

Compound 12

MS: m/z 303.3 (M+1).

$^1$H NMR (CDCl$_3$): d 1.30 (t, 3H), 1.70–1.90 (m, 6H), 2.50 (m, 2H), 3.85–4.00 (m, 6H), 4.50 (m, 1H), 7.05 (m, 3H), 7.25 (m, 1H).

A mixture of 12 (9.7 g, 32.2 mmole) and 9.72 g of PPTS in 50 ml of acetone and H2O (10:1) was refluxed over night. The mixture was cooled to room temperature and acetone was evaporated. Addition of water to the mixture initiated crystalization to give 6.85 g of product 13 (82.3%).

SCHEME 2:

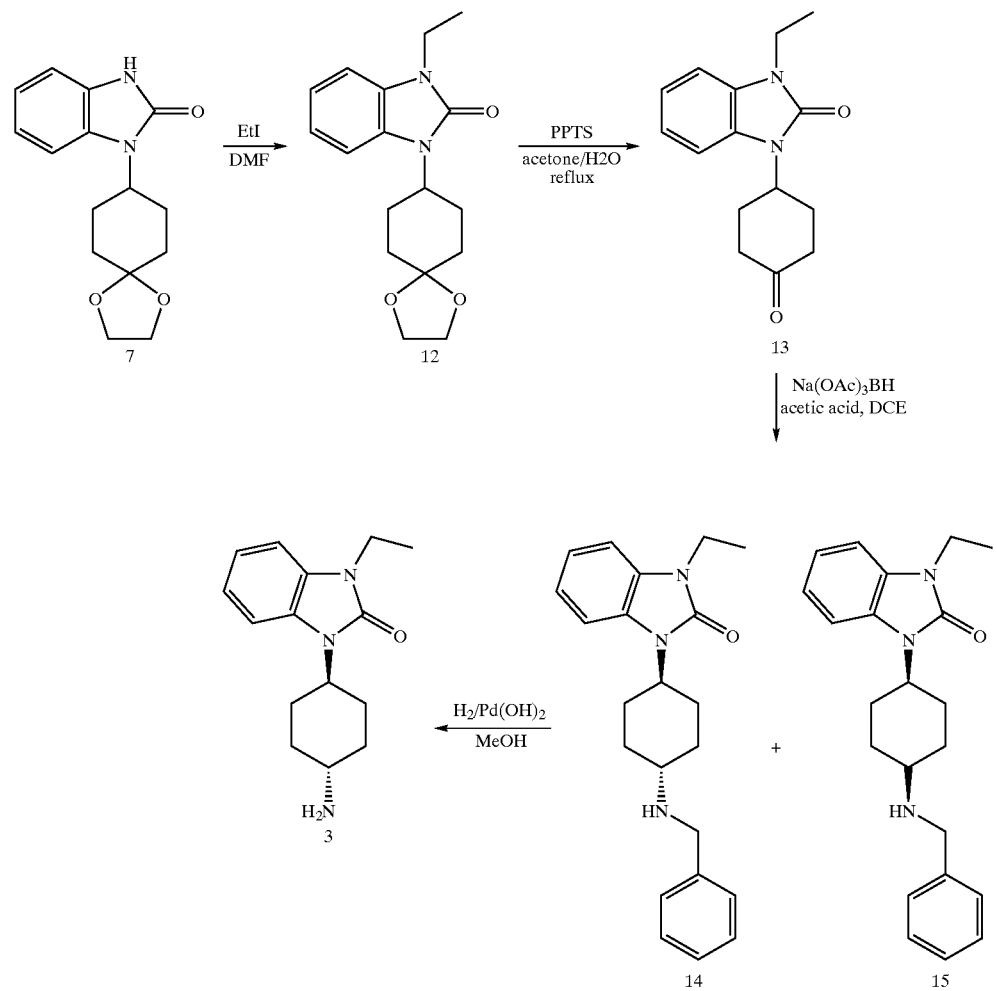

Procedure:

About 2.5 g of NaH was washed by THF twice, suspended in 100 ml of DMF, then 8.15 g of 7 (38 mmole) was added to the mixture. Gas evolves, and after 5 minutes, 7.13 g of ethyl iodide (45.7 mmole) was added. The mixture was stirred over night. LC/MS indicated that the starting material was completely consumed. The reaction was cooled down and H$_2$O was added to the mixture. The product started to precipitated out of solution. The crystals was collected by filtration to give 9.7 g of 12 (84.7%).

Compound 13

MS: m/z 259 (M+1).

$^1$H NMR (CDCl$_3$): d 1.35 (t, 3H), 2.20 (m, 2H), 2.60 (m, 6H), 3.95 (q, 2H), 4.85 (m, 1H), 7.10 (m, 4H).

To a mixture of 13(6.85 g, 26.5 mmole), benzylamine (2.84 g, 26.5 mmole), acetic acid (1.59 g, 26.5 mmole) in 150 ml of dichloroethane, 7.86 g of sodium triacetoxyborohydride (37.1 mmol, 1.4 eq) was added in one portion. Gas evolves between 30 min and 1 hr. The mixture was stirred over night. TLC indicated the reaction was complete. 1 N NaOH (500 ml) was added to quench the reaction. The organic layer was separated and the aqueous layer was extracted with EtOAc (300 ml×2). The combined organics were dried over potassium carbonate and the solvent was evaporated to give a brown solid, which was column filtrated.(5% Et3N,25% EtOAc and 70% Hexane to 10% Et3N, 40% EtOAc and 50% Hexane) to give 1.52 g of product 14 as a white solid and 1.08 g of product 15 as a white solid.

Compound 14

MS: m/z 350 (M+1).

$^1$H NMR (CDCl$_3$): d 1.35 (t, 3H), 1.50 (m, 2H), 1.65 (m, 4H), 1.95.(m, 2H), 2.60 (m, 2H), 3,02 (m, 1H), 3.83 (s, 2H), 3.95 (ddd, 2H), 4.45 (m, 1H), 7.00–7.50 (m, 9H).

Compound 15

MS: m/z 350 (M+1).

$^1$H NMR (CDCl$_3$): d 1.35 (m, 5H), 1.90 (m, 2H), 2.10–2.35 (m, 4H), 2.70 (m, 1H), 3.83 (s, 2H), 3.95 (ddd, 2H), 4.40 (m, 1H), 7.00–7.50 (m, 9H).

0.3 g of Pd(OH)2 was added into a solution of 20 ml of methanol containing 0.5 g of compound 14. The resulting suspension was hydrogenated at 50 psi for 12 hr at room temperature. TLC indicated the reaction was complete over night. The solution was filtered through a pad of celite to remove the catalyst. The celite was washed with methanol twice (20 ml). The organics were combined and solvent was removed to give a pale solid which was purified by chromatography (10% MeOH, 90% EtOAc) to give an off white product 3 (300 mg, 50%).

Compound 3

MS: m/z 232 (M+1).

$^1$H NMR (CDCl$_3$): d 1.35 (t, 3H), 1.50–1.85 (m, 8H), 2.60 (m, 2H), 3.20 (m, 1H), 3.95 (ddd, 2H), 4.30 (m, 1H), 7.10 (m, 3H), 7.30 (m, 1H).

EXAMPLE 11

Attachment of Tail Groups

Tail groups were attached to the head groups according to the following procedures:

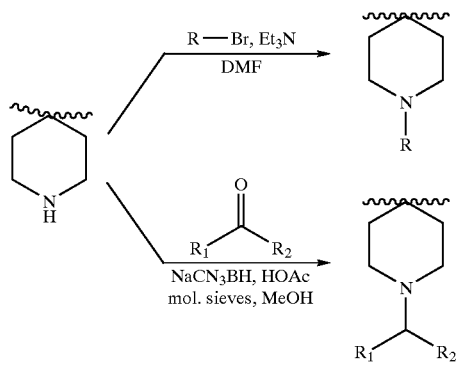

General Procedure for Alkylation:

To a solution of the amine (1 eq) and triethylamine (1 eq) in dimethylformamide, was added 1 eq of alkyl bromide or chloride in one portion. The mixture was stirred and heated at 80° C. over night. TLC indicated the reaction was complete. The reaction was quenched by the addition of water followed by 1 N NaOH to pH 10. The mixture was extracted 2× with Et$_2$O. The combined organic extracts were dried over potassium carbonate and the solvent evaporated, followed by chromatography to give the pure product.

General Procedure for Reductive Amination:

To a mixture of ketone or aldehyde (1 eq), amine (1 eq), and acetic acid (1 eq) in methanol, was added sodium cyanoborohydride (1.4 eq) in one portion. The mixture was stirred over night at room temperature. TLC indicated the reaction was complete. The reaction was quenched by the addition of water followed by 1 N NaOH to pH 10. The mixture was extracted 2× with Et$_2$O. The combined organic extracts were dried over potassium carbonate and the solvent evaporated, followed by chromatography to give the pure product.

The following compounds were prepared by attaching the tail groups using the general procedures described:

1-[4-(benzylamino)-cyclohexyl]-3-ethyl-1,3-dihydro-2H-benzimidazol-2-one

1-[4-(benzylamino)-cyclohexyl]-3-ethyl-1,3-dihydro-2H-benzimidazol-2-one

1-[4-[(naphth-2-yl-methyl)ethylamino]-cyclohexyl]-1,3-dihydro-2H-benzimidazol-2-one MS: m/z 400.2 (M+1)

1-[4-(norbornan-2-ylamino)-cyclohexyl]-1,3-dihydro-2H-benzimidazol-2-one

MS: m/z 326.3 (M+1)

1-[4-[[4-(1-methylethyl)-cyclohexyl]amino]-cyclohexyl]-1,3-dihydro-2H-benzimidazol-2-one MS: m/z 356.4 (M+1)

1-[4-[(decahydro-2-naphthyl)amino]-cyclohexyl]-1,3-dihydro-2H-benzimidazol-2-one MS: m/z 368.2 (M+1)

1-[4-(ethylamino)-cyclohexyl]-1,3-dihydro-2H-benzimidazol-2-one

1-[4-(benzylamino)-cyclohexyl]-1,3-dihydro-2H-benzimidazol-2-one

1-[4-(benzylamino)-cyclohexyl]-1,3-dihydro-2H-benzimidazol-2-one

1-[4-[(indan-2-yl)benzylamino]-cyclohexyl]-3-ethyl-1,3-dihydro-2H-benzimidazol-2-one MS: m/z 466.3 (M+1)

$^1$H—NMR (CDCl$_3$): d 1.30 (t, 3H), 1.50–1.75 (m, 2H), 1.90 (b, 2H), 2.02 (b, 2H), 2.20 (m, 2H), 2.80 (m, 1H), 2.99 (m, 4H), 3.75 (s, 2H), 3.90 (m, 3H), 4.25 (m, 1H), 6.95–7.45 (m, 13H).

1-[4-[(cyclooctylmethyl)amino]-cyclohexyl]-3-ethyl-1,3-dihydro-2H-benzimidazol-2-one

LC: 99%

MS: m/z 384.5

$^1$H NMR (CDCl$_3$): d1.40–1.90 (m,24H), 2.30(m, 2H), 2.50(m, 2H),2.90(m, 1), 3.90 (ddd, 2H) 4.20(m, 1H), 7.10 (m, 3H), 7.30(m, 1H).

1-[4-[(naphth-2-yl)amino]-cyclohexyl]-3-ethyl-1,3-dihydro-2H-benzimidazol-2-one

LC: 97%

MS: m/z 399

$^1$H NMR (CDCl$_3$): d 1.50 (t, 3H), 1.80 (m, 5H), 2.0 (m, 2H), 2.70(m, 2H), 3.10(m, 1H), 3.90(m, 2H), 4.0(m, 2H), 4.40(m, 1H), 7.10(m, 3H), 7.50(m, 4H), 7.90(m, 4H).

1-[4-[(p-benzyloxybenzyl)amino]-cyclohexyl]-3-ethyl-1,3-dihydro-2H-benzimidazol-2-one

LC: 97%

MS: m/z 455

$^1$H NMR (CDCl$_3$): d 1.40 (t, 3H), 1.70 (m,2H), 1.90 (m, 3H), 2.60(m, 4H), 3.10(m, 1H), 3.80(s, 2H), 4.0(m, 2H), 4.50(m, 1H), 5.10(s, 2H), 7.10(m, 6H), 7.50(m, 6H), 7.90(m, 1H).

1-[4-[(cyclooctylmethyl)amino]-cyclohexyl]-3-ethyl-1,3-dihydro-2H-benzimidazol-2-one

LC: 99%

MS: m/z 369

$^1$H NMR (CDCl$_3$): d1.40 (t, 3H), 1.70(m, 5H), 1.90(m, 12H),2.10(m,3H), 2.40(m,2H), 2.50(d, 2H), 3.30(m, 1H), 3.90(m, 2H), 4.20(m, 1H), 7.10(m, 1H), 7.30(m, 3H).

1-[4-[(decahydro-2-naphthyl)amino]-cyclohexyl]-3-ethyl-1,3-dihydro-2H-benzimidazol-2-one
LC: 99%
MS: m/z 395
$^{1}$H NMR (CDCl$_3$): d1.40 (t, 3H), 1.70(m, 3H), 1.80(m, 3H), 1.90(m, 12H), 2.20(m, 2H), 2.30(m, 3H), 2.50(q,2H), 3.10(m, 1H), 3.90(m,2H), 4.20(m, 1H), 4.30(m, 1H), 7.0(m, 1H), 7.30(m, 3H).

1-[4-[(p-phenylbenzyl)amino]-cyclohexyl]-5-carbamoyl-1,3-dihydro-2H-benzimidazol-2-one
LC: 100%
MS: m/z 440.8 (M+1)
$^{1}$H—NMR (MeOH-d$_4$): d 1.75 (m, 2H), 2.00 (m, 2H), 2.40–2.55 (m, 4H), 3.35–3.52 (m, 2H), 4.35 (s, 2H), 7.40 (m, 2H), 7.59 (t, 2H), 7.60–7.72 (m, 6H), 7.78 (d, 2H).

1-[4-[(1,2,3,4-tetrahydronaphthyl)amino]-cyclohexyl]-5-carbamoyl-1,3-dihydro-2H-benzimidazol-2-one
LC: 93.9%
MS: m/z 405.7 (M+1)
$^{1}$H—NMR (MeOH-d$_4$): d 1.70 (m, 2H), 1.85 (m, 1H), 2.02 (m, 2H), 2.39 (b, 3H), 2.50 (m, 2H), 2.90 (m, 1H), 3.00 (b, 2H), 3.35 (m, 1H), 3.60 (m, 1H), 3.72 (b, 1H), 4.35 (m, 1H), 7.15 (b, 4H), 7.40 (d, 1H), 7.60 (s, 1H), 7.65 (d, 1H).

1-[4-[(4-propyl-cyclohexyl)amino]-cyclohexyl]-5-carbamoyl-1,3-dihydro-2H-benzimidazol-2-one
LC: 100%
MS: m/z 399.6 (M+1)
$^{1}$H—NMR (MeOH-d$_4$): d 0.95 (t, 3H), 1.10 (m, 1H), 1.20–1.60 (m, 6H), 1.70 (b, 5H), 1.80–2.00 (m, 4H), 2.10 (m, 1H), 2.30 (b, 2H), 2.45 (m, 2H), 3.25 (m, 1H), 3.50 (m, 1H), 4.40 (m, 1H), 7.40 (d, 1H), 7.60 (s, 1H), 7.65 (d, 1H).

1-[4-[(5-methylhex-2-yl)amino]-cyclohexyl]-5-carbamoyl-1,3-dihydro-2H-benzimidazol-2-one
LC: 100%
MS: m/z 373.5 (M+1)
$^{1}$H—NMR (MeOH-d$_4$): d 0.95 (d, 6H), 1.25–1.40 (m, 5H), 1.50–1.75 (m, 4H), 1.85 (m, 1H), 1.95 (b, 2H), 2.30 (m, 2H), 2.40–2.55 (m, 2H), 3.35–3.55 (m, 2H), 4.38 (m, 1H), 7.40 (d, 1H), 7.60 (s, 1H), 7.70 (d, 1H).

1-[4-[(decahydro-2-naphthyl)amino]-cyclohexyl]-5-carbamoyl-1,3-dihydro-2H-benzimidazol-2-one
LC: 100%
MS: m/z 411.7 (M+1)
$^{1}$H—NMR (MeOH-d$_4$): d 0.90–2.10 (m, 18H),2.10–2.50 (m, 5H),2.82 (m, 1H), 3.50 (m,2H), 4.35 (m, 1H), 7.42 (d, 1H), 7.60 (s, 1H), 7.70 (d, 1H).

1-[4-(cyclooctylamino)-cyclohexyl]-5-carbamoyl-1,3-dihydro-2H-benzimidazol-2-one;
LC: 95.4%
MS: m/z 385.7 (M+1)
$^{1}$H—NMR (MeOH-d$_4$): d 1.50–2.10 (m,13H),2.30(m, 2H), 2.40–2.52 (m,3H), 2.80–2.95 (m, 3H), 3.45 (m, 2H), 3.70 (m, 1H), 4.38 (m, 1H), 7.40 (d, 1H), 7.63 (s, 1H), 7.70 (d, 1H).

1-[4-[(indan-2-yl)amino]-cyclohexyl]-5-carbamoyl-1,3-dihydro-2H-benzimidazol-2-one
LC: 100%
MS: m/z 391.6 (M+1)
$^{1}$H—NMR (MeOH-d$_4$): d 1.70 (m,2H), 2.00 (m, 2H), 2.40–2.60 (m, 4H), 3.10–3.20 (m, 2H), 3.50 (m, 3H), 4.30–4.45 (m, 2H), 7.25 (m, 2H), 7.35 (m, 2H), 7.42 (d, 1H), 7.60 (s,1H), 7.72 (d, 1H).

1-[4-(benzylamino)-cyclohexyl]-5-carbamoyl-1,3-dihydro-2H-benzimidazol-2-one
LC: 100%
MS: m/z 399.5 (M+1)
$^{1}$H—NMR (MeOH-d$_4$): d 1.40–1.85 (m, 15H), 2.00 (m, 4H), 2.25–2.50 (m, 4H), 2.93 (d, 2H), 3.30 (m, 1H), 4.30 (m, 1H), 7.36 (d, 1H), 7.60 (s, 1H), 7.65 (d, 1H).

1-[4-[(4-phenyl-cyclohexyl)amino]-cyclohexyl]-5-carbamoyl-1,3-dihydro-2H-benzimidazol-2-one
LC: 100%
MS: m/z 433.7 (M+1)
$^{1}$H—NMR (MeOH-d$_4$): d 1.65 (m, 2H), 1.85–2.20 (m, 8H), 2.25–2.50 (m, 5H), 3.90 (m, 1H), 3.50 (m, 2H), 3.58 (m, 1H), 4.30 (m, 1H), 7.15–7.40 (m, 6H), 7.60 (s, 1H), 7.65 (d, 1H).

1-[4-(dibenzylamino)-cyclohexyl]-5-carbamoyl-1,3-dihydro-2H-benzimidazol-2-one
LC: 100%
MS: m/z 455.6 (M+1)
$^{1}$H—NMR (MeOH-d$_4$): d 2.00–2.25 (m, 4H), 2.40 (m, 4H), 3.52 (m, 2H), 4.25–4.65 (m, 4H), 7.30 (d, 1H), 7.45–7.58 (m, 10H), 7.60 (s, 1H), 7.65 (d, 1H).

1-[4-[(5-methylhex-2-yl)amino]-cyclohexyl]-7-carbamoyl-1,3-dihydro-2H-benzimidazol-2-one
LC: 99.1%
MS: m/z 373.3 (M+1)
$^{1}$H—NMR (MeOH-d$_4$): d 0.95 (d, 6H), 1.30 (d, 3H), 1.45–1.68 (m, 5H), 1.75 (m, 1H), 2.00 (m, 2H), 2.18–2.32 (m, 3H), 2.60 (m, 2H), 3.20–3.40 (m, 2H), 4.30 (m, 1H), 7.05–7.20 (m, 3H).

Other compounds within the scope of formula (III) or (IIIA) of the present invention can be synthesized by analogous techniques.

EXAMPLE 12

Nociceptin affinity at the ORL1 receptor for preferred compounds was obtained using the following assay:

Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 ml/10 cm dish) followed by homogenization with a tissue grinder/teflon pestle. Membranes were collected by centrifugation at 30,000×g for 15 min at 4° C. and pellets resuspended in hypotonic buffer to a final concentration of 1–3 mg/ml.

Protein concentrations were determined using the BioRad protein assay reagent with bovine serum albumen as standard. Aliquots of the ORL-1 receptor membranes were stored at −80° C.

Functional SGTPgS binding assays were conducted as follows. ORL-1 membrane solution was prepared by sequentially adding final concentrations of 0.066 mg/ml ORL-1 membrane protein, 10 mg/ml saponin, 3 mM GDP and 0.20 nM [$^{35}$S]GTPgS to binding buffer (100 mM NaCl, 10 mM MgCl$_2$, 20 mM HEPES, pH 7.4) on ice. The prepared membrane solution (190 ml/well) was transferred to 96-shallow well polypropylene plates containing 10 ml of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 200 ml ice-cold binding buffer (10 mM NaH$_2$PO$_4$, 10 mM Na$_2$HPO$_4$, pH 7.4). Filter plates were subsequently dried at 50° C. for 2–3 hours. Fifty ml/well scintillation cocktail (BetaScint; Wallac) was added and plates were counted in a Packard Top-Count for 1 min/well.

Data was analyzed using the curve fitting functions in GraphPad PRISMÔ, v. 3.0 and the results are set forth in table 3 below:

TABLE 3

Nociceptin Affinity

| Compound | calc $K_i$ (mM) |
|---|---|
| 3-ethyl-1-(p-phenylbenzyl)-1,3-dihydro-2H-benzimidazol-2-one | 509 |
| 3-ethyl-1-(5-methylhex-2-yl)-1,3-dihydro-2H-benzimidazol-2-one | 23 |
| 3-ethyl-1-(4-propylcyclohexyl)-1,3-dihydro-2H-benzimidazol-2-one | 68 |
| 3-ethyl-1-(decahydro-2-naphthyl)-1,3-dihydro-2H-benzimidazol-2-one | 1.6 |
| 3-ethyl-1-(naphth-2-yl-methyl)-1,3-dihydro-2H-benzimidazol-2-one | 198 |
| 1-(p-benzyloxybenzyl)-3-ethyl-1,3-dihydro-2H-benzimidazol-2-one | 438 |
| 1-benzyl-3-ethyl-1,3-dihydro-2H-benzimidazol-2-one | 296 |
| 1-[4-(benzylamino)-cyclohexyl]-3-ethyl-1,3-dihydro-2H-benzimidazol-2-one | trans: 112 cis: >10,000 |
| 3-ethyl-1-(naphthylmethyl)-1,3-dihydro-2H-benzimidazol-2-one | 39 |
| 3-ethyl-1-[5-(3-fluorophenyl)-5-(4-fluorophenyl)-hexyl]-1,3-dihydro-2H-benzimidazol-2-one | 148 |
| 1-[4-[(naphth-2-yl-methyl)ethylamino]-cyclohexyl]-1,3-dihydro-2H-benzimidazol-2-one | 3598 |
| 1-[4-(norbornan-2-ylamino)-cyclohexyl]-1,3-dihydro-2H-benzimidazol-2-one | >10000 |
| 1-[4-[[4-(1-methylethyl)-cyclohexyl]amino]-cyclohexyl]-1,3-dihydro-2H-benzimidazol-2-one | >10000 |
| 1-[4-[(decahydro-2-naphthyl)amino]-cyclohexyl]-1,3-dihydro-2H-benzimidazol-2-one | >10000 |
| 1-[4-(ethylamino)-cyclohexyl]-1,3-dihydro-2H-benzimidazol-2-one | 9179 |
| 1-[4-(benzylamino)-cyclohexyl]-1,3-dihydro-2H-benzimidazol-2-one | trans: 273 cis: >10000 |
| 1-[4-[(indan-2-yl)benzylamino]-cyclohexyl]-3-ethyl-1,3-dihydro-2H-benzimidazol-2-one | >10000 |
| 1-[4-[(cyclooctylmethyl)amino]-cyclohexyl]-3-ethyl-1,3-dihydro-2H-benzimidazol-2-one | 115 |
| 1-[4-[(naphth-2-yl)amino]-cyclohexyl]-3-ethyl-1,3-dihydro-2H-benzimidazol-2-one | 961 |
| 1-[4-[(p-benzyloxybenzyl)amino]-cyclohexyl]-3-ethyl-1,3-dihydro-2H-benzimidazol-2-one | 2935 |
| 1-[4-[(cyclooctylmethyl)amino]-cyclohexyl]-3-ethyl-1,3-dihydro-2H-benzimidazol-2-one | 286 |
| 1-[4-[(decahydro-2-naphthyl)amino]-cyclohexyl]-3-ethyl-1,3-dihydro-2H-benzimidazol-2-one | 288 |
| 1-(benzylamino)-cyclohexyl]-5-carbamoyl-1,3-dihydro-2H-benzimidazol-2-one | >10000 |
| 1-[4-(dibenzylamino)-cyclohexyl]-5-carbamoyl-1,3-dihydro-2H-benzimidazol-2-one | >10000 |
| 1-[4-[(p-phenylbenzyl)amino]-cyclohexyl]-5-carbamoyl-1,3-dihydro-2H-benzimidazol-2-one | >10000 |
| 1-[4-[(1,2,3,4-tetrahydronaphthyl)amino]-cyclohexyl]-5-carbamoyl-1,3-dihydro-2H-benzimidazol-2-one | >10000 |
| 1-[4-[(4-propyl-cyclohexyl)amino]-cyclohexyl]-5-carbamoyl-1,3-dihydro-2H-benzimidazol-2-one | >10000 |
| 1-[4-[(5-methylhex-2-yl)amino]-cyclohexyl]-5-carbamoyl-1,3-dihydro-2H-benzimidazol-2-one | >10000 |
| 1-[4-[(decahydro-2-naphthyl)amino]-cyclohexyl)-5-carbamoyl-1,3-dihydro-2H-benzimidazol-2-one | >10000 |
| 1-[4-(cyclooctylamino)-cyclohexyl]-5-carbamoyl-1,3-dihydro-2H-benzimidazol-2-one | >10000 |
| 1-[4-[(indan-2-yl)amino]-cyclohexyl]-5-carbamoyl-1,3-dihydro-2H-benzimidazol-2-one | >10000 |
| 1-[4-[(4-phenyl-cyclohexyl)amino]-cyclohexyl]-5-carbamoyl-1,3-dihydro-2H-benzimidazol-2-one | >10000 |
| 1-[4-[(5-methylhex-2-yl)amino]-cyclohexyl]-7-carbamoyl-1,3-dihydro-2H-benzimidazol-2-one | >10000 |

EXAMPLE 13

Synthesis of Substituted Benzimidazole Head Groups

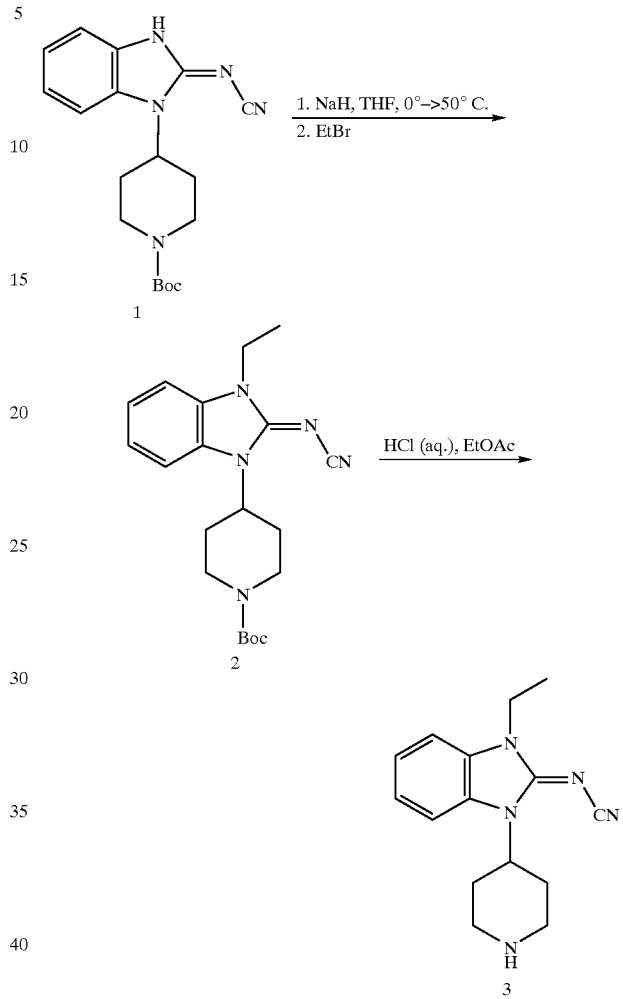

Procedure:

Sodium hydride 60% dispersion in mineral oil (0.67 g, 16.7 mmol) was washed with dry pentane and then suspended in 80 mL of dry THF under $N_2$. Compound 1 (European patent 0029707) (3.80 g, 11.1 mmol) was added, the mixture stirred at room temperature for 15 min and then warmed to 50° C. Ethyl bromide (1.06 mL, 13.3 mmol) was added and the resulting mixture stirred at 50° C. for 18 hr. TLC ($SiO_2$, $CH_2Cl_2$:MeOH 96:4) showed that the reaction was ca 40% complete. Additional sodium hydride (0.67 g) and ethyl bromide (1.06 mL) were added. After heating at 50° C. for an additional 24 hr the reaction mixture was cooled to room temperature and quenched with water. The layers were separated and the aqueous layer extracted with ethyl acetate (1×). The combined organic extracts were washed with aqueous sodium bicarbonate solution (1×), dried over $MgSO_4$ and the solvent was evaporated to give the crude product as a yellow solid. Trituration with diethyl ether gave pure 2 as a white solid (3.38 g, 82%).

$^1$H—NMR ($CDCl_3$): d 1.45–1.55 (m, 12H), 1.82 (bs, 2H), 2.30 (m, 2H), 2.87 (m, 2H), 4.30 (bs, 2H), 4.41 (q, 2H), 4.82 (m, 1H), 7.10–7.30 (m, 4H).

To a solution of 2 (3.60 g, 9.74 mmol) in 100 mL of ethyl acetate was added a 25 mL of a 1:1 mixture of ethyl acetate and concentrated HCl. The mixture was stirred vigorously at room temperature for 2 hr. and evaporated to dryness. The residue was neutralized with 50 mL of methanolic ammonia 10:1 and again evaporated to dryness. The residue was suspended in 100 mL a 1:1 mixture of MeOH and $CH_2Cl_2$, filtered and the filtrate evaporated to dryness to leave an off-white solid. Flash chromatography on silica gel, eluting with $CH_2Cl_2$:MeOH:$NH_3$ (300:10:1) gave pure 3 as a white crystalline solid (1.98 g, 76%).

$^1$H—NMR (CDCl$_3$): d 1.45 (t, 3H), 1.82 (bs, 2H), 2.33 (m, 2H), 2.80 (m, 2H), 4.40 (q, 2H), 4.80 (m, 1H), 7.10–7.30 (m, 3H), 7.45 (d, 1H).

EXAMPLE 14

Attachment of Tail Groups

Tail groups were attached to the head groups according to the following procedures.

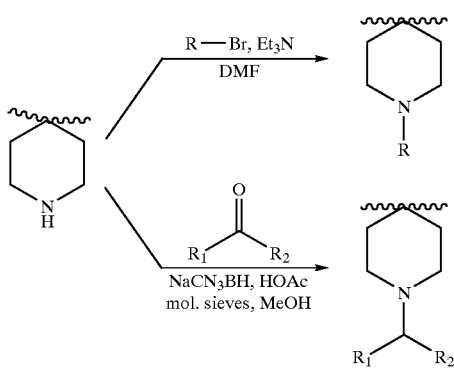

General Procedure for Alkylation:

To a solution of the amine (1 eq) and triethylamine (1 eq) in dimethylformamide, was added 1 eq of alkyl bromide or chloride in one portion. The mixture was stirred and heated at 80° C. over night. TLC indicated the reaction was complete. The reaction was quenched by the addition of water followed by 1 N NaOH to pH 10. The mixture was extracted 2× with Et$_2$O. The combined organic extracts were dried over potassium carbonate and the solvent evaporated, followed by chromatography to give the pure product.

General Procedure for Reductive Amination:

To a mixture of ketone or aldehyde (1 eq), amine (1 eq), and acetic acid (1 eq) in methanol, was added sodium cyanoborohydride (1.4 eq) in one portion. The mixture was stirred over night at room temperature. TLC indicated the reaction was complete. The reaction was quenched by the addition of water followed by 1 N NaOH to pH 10. The mixture was extracted 2× with Et$_2$O. The combined organic extracts were dried over potassium carbonate and the solvent evaporated, followed by chromatography to give the pure product.

The following compounds were prepared by attaching the tail groups using the general procedures described:

2-cyanoimino-3-ethyl-1-[1-(p-phenylbenzyl)-4-piperidinyl]-1,3-dihydro-2H-benzimidazole
$^1$H—NMR (CDCl$_3$): d 1.50 (t, 3H), 1.88 (m, 2H), 2.28 (m, 2H), 2.62 (m, 2H), 3.12 (m, 2H), 3.65 (s, 2H), 4.48 (q, 2H), 4.80 (m, 1H), 7.15–7.70 (m, 13H).

2-cyanoimino-3-ethyl-1-[1-(p-benzyloxybenzyl)-4-piperidinyl]-1,3-dihydro-2H-benzimidazole
LC: 96.5%
MS: m/z 466.5 (M+1)
$^1$H—NMR (CDCl$_3$): d 1.55 (t, 3H), 1.82 (m, 2H), 2.25 (m, 2H), 2.50 (m, 2H), 3.10 (m, 2H), 3.55 (s, 2H), 4.48 (q, 2H), 4.78 (m, 1H), 5.20 (s, 2H), 7.00 (d, 2H), 7.15–7.65 (m, 11H).

2-cyanoimino-3-ethyl-1-[1-(naphth-2-yl-methyl)-4-piperidinyl]1,3-dihydro-2H-benzimidazole
LC: 93.9%
MS: m/z
$^1$H—NMR (CDCl$_3$): d 1.55 (t, 3H), 1.80 (m, 2H), 2.30 (t, 2H), 2.52 (m, 2H), 3.18 (bd, 2H), 3.78 (s, 2H), 4.50 (q, 2H), 4.80 (m, 1H), 7.20–7.90 (m, 11H).

2-cyanoimino-3-ethyl-1-[1-(4-propylcyclohexyl)-4-piperidinyl]-1,3-dihydro-2H-benzimidazole
MS: m/z 394.4 (M+1).
$^1$H—NMR (CDCl$_3$): d 0.90–2.28 (m, 21H), 3.10 (m, 4H), 3.62 (m, 2H), 4.42 (q. 2H), 5.15 (m, 1H), 7.20 (d, 1H), 7.30 (m, 1H), 7.50 (t, 1H), 7.80 (b, 1H).

2-cyanoimino-3-ethyl-1-[1-[4-(2-propyl)-cyclohexyl]-4-piperidinyl]-1,3-dihydro-2H-benzimidazole
LC: 100%
MS: m/z 394.5 (M+1)
$^1$H—NMR (CDCl$_3$): d 0.90 (d, 3H), 0.98 (d, 3H), 1.15–2.35 (m, 14H), 3.10 (m, 5H), 3.70 (m, 2H), 3.92 (bs, 1H), 4.40 (q, 2H), 5.20 (m, 1H), 7.20 (d, 1H), 7.38 (d, 1H), 7.52 (t, 1H), 7.80 (m, 1H).

2-cyanoimino-3-ethyl-1-[1-(decahydro-2-naphthyl)-4-piperidinyl]-1,3-dihydro-2H-benzimidazole
LC: 93.9%
MS: m/z 406.6 (M+1)
$^1$H—NMR (CDCl$_3$): d 1.25–2.35 (m, 24H), 1.15 (m, 4H), 3.60 (m, 2H), 4.40 (m, 2H), 4.20 (m, 1H), 7.20–7.80 (m, 4H).

2-cyanoimino-3-ethyl-1-[1-(cyclooctyl)-4-piperidinyl]-1,3-dihydro-2H-benzimidazole
LC: 100%
MS: m/z 380.3 (M+1)
$^1$H—NMR (CDCl$_3$): d 1.50–1.80 (m, 13H), 1.90 (m, 2H), 2.10 (m,4H), 3.05 (m, 3H), 3.30 (m, 1H), 3.45 (m, 2H), 3.90 (m, 1H), 4.42 (q, 2H), 5.15 (m, 1H), 7.20 (d, 1H), 7.35 (d, 1H), 7.50 (m, 1H), 7.78 (m, 1H).

2-cyanoimino-3-ethyl-1-[1-(10,11-dihydro-5H-dibenzo[a,d]-cyclohepten-5-yl)-4-piperidinyl]-1,3-dihydro-2H-benzimidazole
LC: 94.5%
MS: m/z 462.2 (M+1)
$^1$H—NMR (CDCl$_3$): d 1.40 (t, 3H), 1.70 (bs, 2H), 2.01 (m, 2H), 2.28 (m, 2H), 2.80 (m, 4H), 3.95 (s, 1H), 4.02 (m, 2H), 4.32 (q, 2H), 4.65 (m, 1H), 7.00–7.32 (m, 12H).

2-cyanoimino-3-ethyl-1-[1-(3,3-Bis(phenyl)propyl)-4-piperidinyl]-1,3-dihydro-2H-benzimidazole
MS:. m/z 464.2 (M+1)
$^1$H—NMR (CDCl$_3$): d 1.40 (t, 3H), 1.73 (bs, 2H), 2.09 (m, 2H), 2.18–2.45 (m, 6H), 2.98 (b, 2H), 3.93 (t, 1H), 4.35 (q, 2H), 4.63 (m, 1H), 7.10–7.30 (m, 13H), 7.40 (d, 1H).

2-cyanoimino-3-ethyl-1-[1-(1,2,3,4-tetrahydronaphthyl)-4-piperidinyl]-1,3-dihydro-2H-benzimidazole
LC: 94.0%
MS: m/z 400.2 (M+1)
$^1$H—NMR (CDCl$_3$): d 1.30–1.70 (m, 6H), 1.85 (m, 2H), 2.05 (m, 1H), 2.45 (m, 3H), 2.85 (m, 4H), 3.10 (m, 2H), 4.35 (q, 2H), 4.71 (in, 1H), 7.00–7.60 (m, 8H).

2-cyanoimino-3-ethyl-1-[1-(5-methylhex-2-yl)-4-piperidinyl]-1,3-dihydro-2H-benzimidazol
LC: 94.9%
MS: m/z 368.3 (M+1)
$^1$H—NMR (CDCl$_3$): d 0.85 (d, 6H), 0.95 (d, 3H), 1.12–1.65 (m, 8H), 1.80 (m, 2H), 2.27–2.60 (m, 5H), 2.85 (m, 2H), 4.38 (m, 2H), 4.62 (m, 1H), 7.08–7.30 (m, 3H), 7.45 (m, 1H).

2-cyanoimino-3-ethyl-1-[1-(norbornan-2-yl)-4-piperidinyl]-1,3-dihydro-2H-benzimidazole LC: 99.2%
MS: m/z 364.7 (M+1)
$^1$H—NMR (CDCl$_3$): d 1.10–2.10 (m, 13H), 2.35 (m, 1H), 2.50–2.70 (m, 3H), 2.70–2.90 (m, 3H), 3.50 (m, 2H), 4.50 (q, 2H), 4.80 (m, 1H), 7.35 (m, 2H), 7.48 (m, 1H), 7.75 (m, 1H).

2-cyanoimino-3-ethyl-1-[1-(1,3-dihydroinden-2-yl)-4-piperidinyl]-1,3-dihydro-2H-benzimidazole
LC: 92.1%
MS: m/z 386.2 (M+1)
$^1$H—NMR (CDCl$_3$): d 1.42 (t, 3H), 1.82 (m, 2H), 2.21 (m, 2H), 2.43 (m, 2H), 2.88 (m, 2H), 3.02–3.19 (m, 4H), 3.23 (m, 1H), 4.38 (q, 2H), 4.80 (m, 1H), 7.08–7.30 (m, 7H), 7.45 (d, 1H).

2-cyanoimino-3-ethyl-1-[1-(cyclooctylmethyl)-4-piperidinyl]-1,3-dihydro-2H-benzimidazole
LC: 100%
MS: m/z 394.7 (M+1)
$^1$H—NMR (MeOH): d 1.35–2.00 (m, 20H), 2.60–2.85 (m, 6H), 3.40 (m, 2H), 2.52 (q, 2H), 4.90 (m, 1H), 7.35 (m, 2H), 7.48 (m, 1H), 7.70 (m, 1H).

2-cyanoimino-3-(2-hydroxy)ethyl-1-[1-(cyclooctyl)-4-piperidinyl]-1,3-dihydro-2H-benzimidazole
LC: 100%
MS: m/z 396.3 (M+1)
$^1$H—NMR (DMSO): 7.52 (dt, 1H), 7.45 (dt, 1H), 7.21 (m, 2H), 4.97 (t, 1H), 4.55 (m, 1H), 4.38 (t, 2H), 3.76 (q, 2H), 2.88 (m, 2H), 2.61 (bt, 1H), 2.33 (m, 4H), 1.76–1.37 (m, 16H).

2-cyanoimino-3-methoxycarbonylmethyl-1-[1-(cyclooctyl)-4-piperidinyl]-1,3-dihydro-2H-benzimidazole
LC: 98.3%
MS: m/z 424.2 (M+1)
$^1$H—NMR (DMSO): 7.56 (dd, 1H), 7.51 (dd, 1H), 7.25 (m, 2H), 5.26 (s, 2H), 4.56 (m, 1H), 3.72 (s, 3H), 3.34 (m, 2H), 2.78 (m, 2H), 2.62 (bt, 1H), 2.32 (m, 4H), 1.80–1.35 (m, 16H).

2-cyanoimino-3-cyanomethyl-1-[1-(cyclooctyl)-4-piperidinyl]-1,3-dihydro-2H-benzimidazole
LC: 100%
MS: m/z 391.2 (M+1)
$^1$H—NMR (DMSO): 7.60 (m, 2H), 7.31 (m, 2H), 5.48 (s, 2H), 4.77 9 m, 1H), 3.33 (d, 2H) 2.88 (m, 2H), 2.62 (bt, 1H), 2.33 (m, 4H), 1.86–1.37 (m, 16H).

2-cyanoimino-3-butyl-1-[1-(cyclooctyl)-4-piperidinyl]-1,3-dihydro-2H-benzimidazole
LC: 95.4%
MS: m/z 352.2 (M+1)
$^1$H—NMR (DMSO): 7.58 (dd, 1H), 7.49 (dd, 1H), 7.24 (m, 2H), 6.55 (s, 2H), 4.59 (m, 1H), 4.34 (t,2H),2.97 (m,2H),2.80 (m, 1H),2.55 (m, 2H),2.38 (m, 4H), 1.80–1.30 (m, 18H), 0.90 (t, 3H).

2-cyanoimino-3-(2-methanesulfonamido)ethyl-1-[1-(cyclooctyl)-4-piperidinyl]-1,3-dihydro-2H-benzimidazole
LC: 100%
MS: m/z 473.2 (M+1)
$^1$H—NMR (DMSO): 7.53 (dd, 1H), 7.44 (dd, 1H), 7.23 (m, 2H), 4.60 (m, 1H), 4.35 (t, 2H), 3.37 (t, 2H), 2.87 (m, 2H), 2.82 (s, 3H), 2.60 (bt, 1H), 2.31 (m, 4H), 1.76–1.37 (m, 15H).

2-cyanoimino-3-acetomido-1-[1-(cyclooctyl)-4-piperidinyl]-1,3-dihydro-2H-benzimidazole
LC: 100%
MS: m/z 409.2 (M+1)
$^1$H—NMR (DMSO): 7.75 (s, 1H), 7.52 (dd, 1H), 7.37 (s, 1H), 7.30 (dd, 1H), 7.20 (m, 2H), 4.96 (s, 2H), 4.55 (m, 1H), 3.33 (d, 2H), 2.88 (m, 2H), 2.62 (bt, 1H), 2.30 (m, 4H), 1.80–1.37 (m, 15H).

2-cyanoimino-3-carboxymethyl-1-[1-(cyclooctyl)-4-piperidinyl]-1,3-dihydro-2H-benzimidazole
LC: 97.5%
MS: m/z 409.9 (M+1)
$^1$H—NMR (DMSO): 7.45 (dd, 1), 7.14 (m, 3H), 4.57 (s, 2H), 4.50 (m, 1H), 2.87 (m, 2H), 2.61 (bt, 1H), 2.33 (m, 4H), 1.75–1.37 (m, 15H).

2-cyanoimino-3-(2-dimethylamino)ethyl-1-[1-(cyclooctyl)-4-piperidinyl]-1,3-dihydro-2H-benzimidazole
LC: 100%
MS: m/z 423.3 (M+1)
$^1$H—NMR (DMSO): 7.60–6.96 (m, 4H), 6.54 (2H, s), 4.65 (m, 1H), 4.40 (t, 2H), 3.90 (t, 2H), 3.05 (m, 4H), 2.90 (m, 1H), 2.63 (m, 3H), 2.56–2.37 (m, 4H), 1.85–1.35 (m, 15H).

2-cyanoimino-1-[1-(cyclooctyl)-3-hydroxymethyl-4-piperidinyl]-1,3-dihydro-2H-benzimidazole 2-cyanoimino-1-[1-(cyclooctyl)-4-piperidinyl]-1,3-dihydro-2H-7-azabenzimidazole;

2-cyanoimino-1-[1-(cyclooctyl)-2,6-ethano-4-one-4-piperidinyl]-1,3-dihydro-2H-benzimidazole Other compounds within the scope of formula (IV) or (IVA) of the present invention can be synthesized by analogous techniques.

EXAMPLE 15

Nociceptin affinity at the ORL1 receptor for preferred compounds was obtained using the following assay:

Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 ml/10 cm dish) followed by homogenization with a tissue grinder/teflon pestle. Membranes were collected by centrifugation at 30,000×g for 15 min at 4° C. and pellets resuspended in hypotonic buffer to a final concentration of 1–3 mg/ml. Protein concentrations were determined using the BioRad protein assay reagent with bovine serum albumen as standard. Aliquots of the ORL-1 receptor membranes were stored at −80° C.

Functional SGTPgS binding assays were conducted as follows. ORL-1 membrane solution was prepared by sequentially adding final concentrations of 0.066 mg/ml ORL-1 membrane protein, 10 mg/ml saponin, 3 mM GDP and 0.20 nM [$^{35}$S]GTPgS to binding buffer (100 mM NaCl, 10 mM MgCl$_2$, 20 mM HEPES, pH 7.4) on ice. The prepared membrane solution (190 ml/well)was transferred to 96-shallow well polypropylene plates containing 10 ml of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 260 ml ice-cold binding buffer (10 mM NaH$_2$PO$_4$, 10 mM Na$_2$HPO$_4$, pH 7.4). Filter plates were subsequently dried at 50° C. for 2–3 hours. Fifty ml/well scintillation cocktail (BetaScint; Wallac) was added and plates were counted in a Packard. Top-Count for 1 min/well.

Data was analyzed using the curve fitting functions in GraphPad PRISMÔ, v. 3.0 and the results are set forth in table 4 below:

TABLE 45

Nociceptin Affinity

| Compound | calc $K_i$ (nM) |
|---|---|
| 2-cyanoimino-3-ethyl-1-[1-(p-phenylbenzyl)-4-piperidinyl]-1,3-dihydro-2H-benzimidazole | 5558 |
| 2-cyanoimino-3-ethyl-1-[1-(p-benzyloxybenzyl)-4-piperidinyl]1,3-dihydro-2H-benzimidazole | 1660 |
| 2-cyanoimino-3-ethyl-1-[1-(naphth-2-yl-methyl)-4-piperidinyl]1,3-dihydro-2H-benzimidazole | 882 |
| 2-cyanoimino-3-ethyl-1-[1-(4-propylcyclohexyl)-4-piperidinyl]-1,3-dihydro-2H-benzimidazole | 241 |
| 2-cyanoimino-3-ethyl-1-[1-[4-(2-propyl)-cyclohexyl]-4-piperidinyl]-1,3-dihydro-2H-benzimidazole | 6.9 |
| 2-cyanoimino-3-ethyl-1-[1-(decahydro-2-naphthyl)-4-piperidinyl]-1,3-dihydro-2H-benzimidazole | 6.6 |
| 2-cyanoimino-3-ethyl-1-[1-(cyclooctyl)-4-piperidinyl]-1,3-dihydro-2H-benzimidazole | 5.57 |
| 2-cyanoimino-3-ethyl-1-[1-(10,11-Dihydro-5H-dibenzo[a,d]-cyclohepten-5-yl)-4-piperidinyl]-1,3-dihydro-2H-benzimidazole; | >10,000 |
| 2-cyanoimino-3-ethyl-1-[1-(3,3-Bis(phenyl)propyl)-4-piperidinyl]-1,3-dihydro-2H-benzimidazole; | 80 |
| 2-cyanoimino-3-ethyl-1-[1-(1,2,3,4-tetrahydronaphthyl)-4-piperidinyl]-1,3-dihydro-2H-benzimidazole; | 157 |
| 2-cyanoimino-3-ethyl-1-[1-(5-methylhex-2-yl)-4-piperidinyl]-1,3-dihydro-2H-benzimidazole; | 76 |
| 2-cyanoimino-3-ethyl-1-[1-(norbornan-2-yl)-4-piperidinyl]-1,3-dihydro-2H-benzimidazole | 323 |
| 2-cyanoimino-3-ethyl-1-[1-(1,3-dihydroinden-2-yl)-4-piperidinyl]-1,3-dihydro-2H-benzimidazole; and | 89 |
| 2-cyanoimino-3-ethyl-1-[1-(cyclooctylmethyl)-4-piperidinyl]-1,3-dihydro-2H-benzimidazole. | 7.1 |
| 2-cyanoimino-3-(2-hydroxy)ethyl-1-[1-(cyclooctyl)-4-piperidinyl]-1,3-dihydro-2H-benzimidazole | 6.4 |
| 2-cyanoimino-3-methoxycarbonylmethyl-1-[1-(cyclooctyl)-4-piperidinyl]-1,3-dihydro-2H-benzimidazole | 3.3 |
| 2-cyanoimino-3-cyanomethyl-1-[1-(cyclooctyl)-4-piperidinyl]-1,3-dihydro-2H-benzimidazole | .97 |
| 2-cyanoimino-3-butyl-1-[1-(cyclooctyl)-4-piperidinyl]-1,3-dihydro-2H-benzimidazole | 1.36 |
| 2-cyanoimino-3-(2-methanesulfonamido)ethyl-1-[1-(cyclooctyl)-4-piperidinyl]-1,3-dihydro-2H-benzimidazole | 78 |
| 2-cyanoimino-3-acetomido-1-[1-(cyclooctyl)-4-piperidinyl]-1,3-dihydro-2H-benzimidazole | 11 |
| 2-cyanoimino-3-carboxymethyl-1-[1-(cyclooctyl)-4-piperidinyl]-1,3-dihydro-2H-benzimidazole | 201 |
| 2-cyanoimino-3-(2-dimethylamino)ethyl-1-[1-(cyclooctyl)-4-piperidinyl]-1,3-dihydro-2H-benzimidazole | 18 |
| 2-cyanoimino-1-[1-(cyclooctyl)-3-hydroxymethyl-4-piperidinyl]-1,3-dihydro-2H-benzimidazole | 473 |
| 2-cyanoimino-1-[1-(cyclooctyl)-4-piperidinyl]-1,3-dihydro-2H-7-azabenzimidazole | 3743 |
| 2-cyanoimino-1-[1-cyclooctyl)-2,6-ethano-4-one-4-piperidinyl]-1,3-dihydro-2H-benzimidazole | 19 |

EXAMPLE 16

Affinity at the μ receptor for compounds was obtained according to the following assay:

Mu opioid receptor membrane solution was prepared by sequentially adding final concentrations of 0.075 μg/μl of the desired membrane protein, 10 μg/ml saponin, 3 μM GDP and 0.20 nM [$^{35}$S]GTPgS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at room temperature with shaking. Reactions were terminated by rapid filtration onto 96-well Unifilter GF/B filter plates (Packard) using a 96-well tissue harvester (Brandel) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2–3 hours. Fifty μl/well scintillation cocktail (MicroScint20, Packard) was added and plates were counted in a Packard Top-Count for 1 min/well.

Data were analyzed using the curve fitting functions in GraphPad PRISM®, v.3.0 and the results for several compounds are set forth in table 5 below:

TABLE 5

Mu Receptor Affinity

| Compound | calc $K_i$ (nM) |
|---|---|
| 3-[1-(naphth-1-yl-methyl)-4-piperidinyl]-2H-benzoxazol-2-one | 340 |
| 3-[1-(3,3-diphenylpropyl)-4-piperidinyl]-2H-benzoxazol-2-one | 726 |
| 3-[1-(1,2,3,4-tetrahydro-2-naphthyl)-4-piperidinyl]-2H-benzoxazol-2-one | 343 |
| 3-[1-(4-propyl-cyclohexyl)-4-piperidinyl]-2H-benzoxazol-2-one | 145 |
| 3-ethylidene-1-[1-(1,2,3,4-tetrahydro-2-naphthyl)-4-piperidinyl]-1,3-dihydro-2H-indole-2-one | 23.3 |
| 3-ethylidene-1-[1-(naphth-2-yl-methyl)-4-piperidinyl]-1,3-dihydro-2H-indole-2-one | 137 |
| 3-ethylidene-1-[1-(p-benzyloxybenzyl)-4-piperidinyl]-1,3-dihydro-2H-indole-2-one | 1150 |
| 3-ethylidene-1-[1-(3,3-diphenylpropyl)-4-piperidinyl]-1,3-dihydro-2H-indole-2-one | 24 |
| 1-[4-[(naphth-2-yl)amino]-cyclohexyl]-3-ethyl-1,3-dihydro-2H-benzimidazol-2-one | 2.1 |
| 2-cyanoimino-3-ethyl-1-[1-(4-propylcyclohexyl)-4-piperidinyl]-1,3-dihydro-2H-benzimidazole | 46 |
| 2-cyanoimino-3-ethyl-1-[1-(1,2,3,4-tetrahydronaphthyl)-4-piperidinyl]-1,3-dihydro-2H-benzimidazole | 458 |
| 2-cyanoimino-3-ethyl-1-[1-(5-methylhex-2-yl)-4-piperidinyl]-1,3-dihydro-2H-benzimidazole | 15 |
| 2-cyanoimino-3-ethyl-1-[1-(norbornan-2-yl)-4-piperidinyl]-1,3-dihydro-2H-benzimidazole | 1653 |

What is claimed is:

1. A compound of formula (IV):

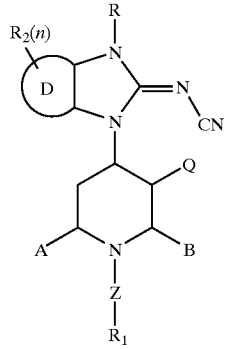

(IV)

wherein R is $C_{1-10}$ alkyl, $C_{3-12}$ cycloalkyl, $C_{3-12}$ cycloalkyl$C_{1-4}$alkyl-, $C_{1-10}$ alkoxy, $C_{3-12}$ cycloalkoxy-, $C_{1-10}$ alkyl substituted with 1–3 halogen, $C_{3-12}$ cycloalkyl substituted with 1–3 halogen, $C_{3-12}$ cycloalkyl$C_{1-4}$alkyl-substituted with 1–3 halogen, $C_{1-10}$ alkoxy substituted with 1–3 halogen, $C_{3-12}$ cycloalkoxy-substituted with 1–3 halogen, —COOV$_1$, —C$_{1-4}$COOV$_1$, —CH$_2$OH, —SO$_2$N(V$_1$)$_2$, hydroxyC$_{1-10}$alkyl-, hydroxyC$_{3-10}$cycloalkyl-, cyanoC$_{1-10}$alkyl-, cyanoC$_{3-10}$cycloalkyl-, —CON(V1)$_2$, NH$_2$SO$_2$C$_{1-4}$ alkyl-, NH$_2$SOC$_{1-4}$alkyl-, sulfonylaminoC$_{1-10}$alkyl-, diaminoalkyl-, -sulfonylC$_{1-4}$ alkyl, a 6-membered aromatic ring, a 6-membered aromaticC$_{1-4}$ alkyl-, —C$_{1-5}$(=O)W$_1$, —C$_{1-5}$(=NH)W$_1$, —C$_{1-5}$NHC(=O)W$_1$, —C$_{1-5}$NHS(=O)$_2$W$_1$, —C$_{1-5}$NHS(=O)W$_1$, wherein W$_1$ is hydrogen, $C_{1-10}$ alkyl, $C_{3-12}$ cycloalkyl, $C_{1-10}$ alkoxy, $C_{3-12}$ cycloalkoxy, —$CH_2OH$, amino, $C_{1-4}$alkylamino-, or di$C_{1-4}$alkylamino-;

wherein each $V_1$ is independently selected from H, $C_{1-6}$ alkyl, $C_{3-6}$ cycloalkyl, benzyl and phenyl;

D is a 5–8 membered cycloalkyl or a 6 membered aromatic group;

n is an integer from 0 to 3;

A, B and Q are independently hydrogen, $C_{1-10}$ alkyl, $C_{3-12}$ cycloalkyl, $C_{1-10}$ alkoxy, $C_{3-12}$ cycloalkoxy, —$CH_2OH$, —$NHSO_2$, hydroxy$C_{1-10}$alkyl-, aminocarbonyl-, $C_{1-4}$alkylaminocarbonyl-, di$C_{1-4}$ alkylaminocarbonyl-, acylamino-, acylaminoalkyl-, amide, sulfonylamino$C_{1-10}$alkyl-, or A–B can together form a $C_{2-6}$ bridge, or B–Q can together form a $C_{3-6}$ bridge, or A-Q can together form a $C_{1-5}$ bridge;

Z is selected from the group consisting of a bond, straight or branched $C_{1-6}$ alkylene, —NH—, —$CH_2O$—, —$CH_2NH$—, —$CH_2N(CH_3)$—, —$NHCH_2$—, —$CH_2CONH$—, —$NHCH_2CO$—, —$CH_2CO$—, —$COCH_2$—, —$CH_2COH_2$—, —$CH(CH_3)$—, —CH=, —O— and —HC=CH—, wherein the carbon and/or nitrogen atoms are unsubstituted or substituted with one or more lower alkyl, hydroxy, halo or alkoxy group;

$R_1$ is selected from the group consisting of hydrogen, $C_{1-10}$ alkyl, $C_{3-12}$cycloalkyl, $C_{2-10}$alkenyl, amino, $C_{1-10}$alkylamino-, $C_{3-12}$cycloalkylamino-, —$COOV_1$, —$C_{1-4}COOV_1$, cyano, cyano$C_{1-10}$alkyl-, cyano$C_{3-10}$ cycloalkyl-, $NH_2SO_2$—, $NH_2SO_2C_{1-4}$alkyl-, $NH_2SOC_{1-4}$alkyl-, aminocarbonyl-, $C_{1-4}$alkylaminocarbonyl-, di$C_{1-4}$alkylaminocarbonyl-, benzyl, $C_{3-12}$ cycloalkenyl-, a monocyclic, bicyclic or tricyclic aryl, and a spiro ring system of the formula (V):

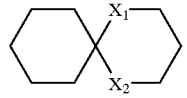

(V)

wherein $X_1$ and $X_2$ are $CH_2$; and wherein said alkyl, cycloalkyl, alkenyl, $C_{1-10}$alkylamino-, $C_{3-12}$cycloalkylamino-, or benzyl of $R_1$ is optionally substituted with 1–3 substituents selected from the group consisting of halogen, hydroxy, $C_{1-10}$ alkyl, $C_{1-10}$ alkoxy, nitro, trifluoromethyl-, cyano, —$COOV_1$, —$C_{1-4}COOV_1$, cyano$C_{1-10}$alkyl-, —$C_{1-5}(=O)W_1$, —$C_{1-5}NHS(=O)_2W_1$, —$C_{1-5}NHS(=O)W_1$, phenyl, benzyl, benzyloxy, said phenyl, benzyl, and benzyloxy optionally being substituted with 1–3 substituents selected from the group consisting of halogen, $C_{1-10}$ alkyl-, $C_{1-10}$ alkoxy-, and cyano; and wherein said $C_{3-12}$ cycloalkyl, $C_{3-12}$ cycloalkenyl, monocyclic, bicyclic or tricyclic aryl, or spiro ring system of the formula (II) is optionally substituted with 1–3 substituents selected from the group consisting of halogen, $C_{1-10}$ alkyl, $C_{1-10}$ alkoxy, nitro, trifluoromethyl-, phenyl, benzyl, phenyloxy and benzyloxy, wherein said phenyl, benzyl, phenyloxy or benzyloxy is optionally substituted with 1–3 substituents selected from the group consisting of halogen, $C_{1-10}$ alkyl, $C_{1-10}$ alkoxy, and cyano;

$R_2$ is selected from the group consisting of hydrogen, $C_{1-10}$ alkyl, $C_{3-12}$ cycloalkyl-and halogen, said alkyl or cycloalkyl optionally substituted with an oxo, amino, alkylamino or dialkylamino group;

or a pharmaceutically acceptable salt thereof or solvate thereof.

2. A compound of claim 1, wherein D is phenyl.

3. A compoun of claim 1, wherein R is selected from the group consisting of —$CH_2C=ONH_2$, —$C(NH)NH_2$, cyclopentyl, cyclohexyl, —C=$OCH_3$, —$CH_2CH_2NHC=OCH_3$, —$SO_2CH_3$, $CH_2CH_2NHSO_2CH_3$, trifluoroethyl-, hydroxyethyl-, and cyanomethyl-.

4. A compound of claim 1, wherein $ZR_1$ is selected from the group consisting of cyclohexylethyl-, cyclohexylmethyl-, cyclopentylmethyl-, dimethylcyclohexylmethyl-, phenylethyl-, cyclopentyl-, cyclohexyl-, methoxycyclohexyl-, phenyltrifluoroethyl-, hydroxyhexyl-, methoxyhexyl-, isopropoxybutyl-, and hexyl-.

5. A compound of claim 1, wherein at least one of $ZR_1$ or R is selected from the group consisting of $CH_2COOV_1$, cyanomethyl-, $NH_2SO_2$methyl-, $NH_2SO$methyl-, aminocarbonylmethyl-, $C_{1-4}$alkylaminocarbonylmethyl-, and di$C_{1-4}$alkylaminocarbonylmethyl-.

6. A compound of claim 1, wherein $ZR_1$ is 3,3 diphenyl-propyl optionally substituted at the 3 carbon of the propyl with —$COOV_1$, cyano-, aminocarbonyl-, $C_{1-4}$alkylaminocarbonyl-, or di$C_{1-4}$alkylaminocarbonyl-.

7. A compound of the formula (IVA):

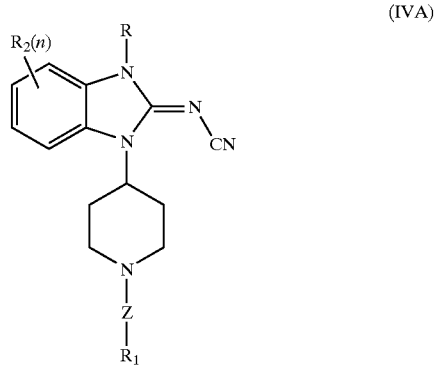

(IVA)

wherein n is an integer from 0 to 3;

Z is selected from the group consisting of a bond, —$CH_2$—, —NH—, —$CH_2O$—, —$CH_2CH_2$—, —$CH_2NH$—, —$CH_2N(CH_3)$—, —$NHCH_2$—, —$CH_2CONH$—, —$NHCH_2CO$—, —$CH_2CO$—, —$COCH_2$—, —$CH_2COCH_2$—, —$CH(CH_3)$—, —CH=, and —HC=CH—, wherein the carbon and/or nitrogen atoms are unsubstituted or substituted with a lower alkyl, halogen, hydroxy or alkoxy group;

R is selected from the group consisting of $C_{1-10}$ alkyl, $C_{1-10}$ alkoxy, and $C_{3-12}$cycloalkyl;

$R_1$ is selected from the group consisting of hydrogen, $C_{1-10}$alkyl, $C_{3-12}$cycloalkyl, $C_{2-10}$alkenyl, amino, $C_{1-10}$alkylamino, $C_{3-12}$cycloalkylamino, benzyl, $C_{3-12}$ cycloalkenyl, a monocyclic, bicyclic or tricyclic aryl, and a spiro ring system of the formula (V):

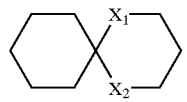

(V)

wherein $X_1$ and $X_2$ are $CH_2$;

wherein said alkyl, cycloalkyl, alkenyl, $C_{1-10}$alkylamino, $C_{3-12}$cycloalkylamino, or benzyl is optionally substituted with 1–3 substituents selected from the group consisting of halogen, $C_{1-10}$ alkyl, $C_{1-10}$ alkoxy, nitro, trifluoromethyl, cyano, phenyl, benzyl, benzyloxy, said phenyl, benzyl, and benzyloxy optionally being substituted with 1–3 substituents selected from the group consisting of halogen, $C_{1-10}$ alkyl, $C_{1-10}$ alkoxy, and cyano;

wherein said $C_{3-12}$ cycloalkyl, $C_{3-12}$ cycloalkenyl, monocyclic, bicyclic or tricyclic aryl, and spiro ring system of the formula (V) are optionally substituted with 1–3 substituents selected from the group consisting of halogen, $C_{1-10}$ alkyl, $C_{1-10}$ alkoxy, nitro, trifluoromethyl, phenyl, benzyl, phenyloxy and benzyloxy, wherein said phenyl, benzyl, phenyloxy and benzyloxy are optionally substituted with 1–3 substituents selected from the group consisting of halogen, $C_{1-10}$ alkyl, $C_{1-10}$ alkoxy, and cyano;

$R_2$ is selected from the group consisting of hydrogen, $C_{1-10}$ alkyl, $C_{3-12}$ cycloalkyl and halogen, said alkyl optionally substituted with an oxo group;

or a pharmaceutically acceptable salt thereof.

8. A compound of claim 7, wherein $R_1$ is alkyl selected from the group consisting of methyl, ethyl, propyl, butyl, pentyl and hexyl.

9. A compound of claim 7, wherein $R_1$ is cycloalkyl selected from the group consisting of cyclohexyl, cycloheptyl, cyclooctyl, cyclononyl, cyclodecyl, and norbornyl.

10. A compound of claim 7, wherein $R_1$ is tetrahydronaphthyl, decahydronaphthyl or dibenzocycloheptyl.

11. A compound of claim 7, wherein $R_1$ is phenyl or benzyl.

12. A compound of claim 7, wherein $R_1$ is a bicyclic aromatic ring.

13. A compound of claim 12, wherein said bicyclic aromatic ring is indenyl or naphthyl.

14. A compound of claim 7, wherein Z is a bond, methyl, or ethyl.

15. A compound of claim 7, wherein n is 0.

16. A compound of claim 7, wherein $X_1$ and $X_2$ are both O.

17. A compound selected from the group consisting of
2-cyanoimino-3-acetomido-1-[1-(cyclooctyl)-4-piperidinyl]-1,3-dihydro-2H-benzimidazole;
2-cyanoimino-3-ethyl-1-[1-(p-phenylbenzyl)-4-piperidinyl]-1,3-dihydro-2H-benzimidazole;
2-cyanoimino-3-ethyl-1-[1-(p-benzyloxybenzyl)-4-piperidinyl]1,3-dihydro-2H-benzimidazole;
2-cyanoimino-3-ethyl-1-[1-(naphth-2-yl-methyl)-4-piperidinyl]1,3-dihydro-2H-benzimidazole;
2-cyanoimino-3-ethyl-1-[1-(4-propylcyclohexyl)-4-piperidinyl]-1,3-dihydro-2H-benzimidazole;
2-cyanoimino-3-ethyl-1-[1-[4-(2-propyl)-cyclohexyl]-4-piperidinyl]-1,3-dihydro-2H-benzimidazole;
2-cyanoimino-3-ethyl-1-[1-(decahydro-2-naphthyl)-4-piperidinyl]-1,3-dihydro-2H-benzimidazole;
2-cyanoimino-3-ethyl-1-[1-(cyclooctyl)-4-piperidinyl]-1,3-dibydro-2H-benzimidazole;
2-cyanoimino-3-ethyl-1-[1-(10,11-dihydro-5H-dibenzo [a,d]-cyclohepten-5-yl)-4-piperidinyl]-1,3-dihydro-2H-benzimidazole;
2-cyanoimino-3-ethyl-1-[1-(3,3-Bis(phenyl)propyl)-4-piperidinyl]-1,3-dihydro-2H-benzimidazole;
2-cyanoimino-3-ethyl-1-[1-(1,2,3,4-tetrahydronaphthyl)-4-piperidinyl]-1,3-dihydro-2H-benzimidazole;
2-cyanoimino-3-ethyl-1-[1-(5-methylhex-2-yl)-4-piperidinyl]-1,3-dihydro-2H-benzimidazole;
2-cyanoimino-3-ethyl-1-[1-(norbornan-2-yl)-4-piperidinyl]-1,3-dihydro-2H-benzimidazole;
2-cyanoimino-3-ethyl-1-[1-(1,3-dihydroinden-2-yl)-4-piperidinyl]-1,3-dihydro-2H-benzimidazole;
2-cyanoimino-3-ethyl-1-[1-(cyclooctylmethyl)-4-piperidinyl]-1,3-dihydro-2H-benzimidazale; and pharmaceutically acceptable salts thereof.

18. A compound selected from the group consisting of
2-cyanoimino-3-(2-hydroxy)ethyl-1-[1-(cyclooctyl)-4-piperidinyl]-1,3-dihydro-2H-benzimidazole;
2-cyanoimino-3-methoxycarbonylmethyl-1-[1-(cyclooctyl)-4-piperidinyl]-1,3-dihydro-2H-benzimidazole;
2-cyanoimino-3-cyanomethyl-1-[1-(cyclooctyl)-4-piperidinyl]-1,3-dihydro-2H-benzimidazole;
2-cyanoimino-3-butyl-1-[1-(cyclooctyl)-4-piperidinyl]-1,3-dihydro-2H-benzimidazole;
2-cyanoimino-3-(2-methanesulfonamido)ethyl-1-[1-(cyclooctyl)-4-piperidinyl]-1,3-dihydro-2H-benzimidazole;
2-cyanoimino-3-acetomido-1-[1-(cyclooctyl)-4-piperidinyl]-1,3-dihydro-2H-benzimidazole;
2-cyanoimino-3-carboxymethyl-1-[1-(cyclooctyl)-4-piperidinyl]-1,3-dihydro-2H-benzimidazole;
2-cyanoimino-3-(2-dimethylamino)ethyl-1-[1-(cyclooctyl)-4-piperidinyl]-1,3-dihydro-2H-benzimidazole; and pharmaceutically acceptable salts thereof and solvates thereof.

19. A pharmaceutical composition comprising a compound of claim 1 and at least one pharmaceutically acceptable excipient.

20. A method of treating pain comprising administering to patient in need thereof, an effective amount of an analgesic compound according to claim 1.

21. A pharmaceutical composition comprising a compound of claim 7 and at least one pharmaceutically acceptable excipient.

22. A method of treating pain comprising administering to a patient in need thereof, an effective amount of an analgesic compound according to claim 7.

23. A compound of the formula (IVA):

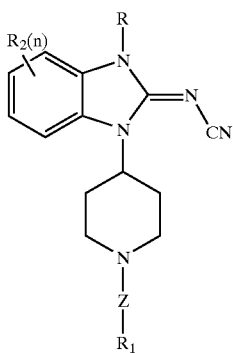

(IVA)

wherein
n is an integer from 0 to 3;
R is selected from the group consisting of $C_{1-10}$ alkyl, $C_{1-10}$ alkoxy, and $C_{3-12}$cycloalkyl;
$R_2$ is selected from the group consisting of hydrogen, $C_{1-10}$ alkyl, $C_{3-12}$ cycloalkyl and halogen, said alkyl optionally substituted with an oxo group;
$ZR_1$ is the following

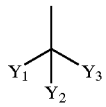

wherein
$Y_1, Y_2$ and $Y_3$, together with the carbon to which they are attached, form one of the following structures:

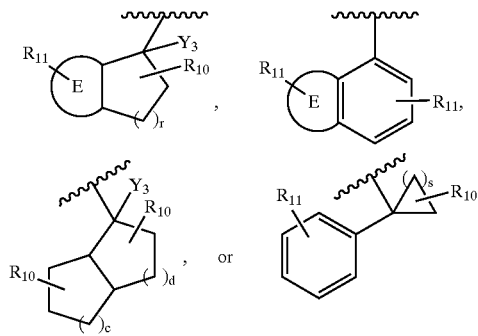

wherein r is 0 to 3; c and d are independently 1 or 2; s is 1 to 5; and ring E is a fused $R_4$-phenyl ring;

$R_{10}$ is 1 to 3 substituents independently selected from the group consisting of H, $(C_1-C_6)$alkyl, $-OR_8$, $-(C_1-C_6)$alkyl-$OR_8$, $-NR_8R_9$ and $-(C_1-C_6)$alkyl-$NR_8R_9$;

$R_{11}$ is 1 to 3 substituents independently selected from the group consisting of $R_{10}$, $-CF_3$, $-OCF_3$, $NO_2$ and halo;

$R_8$ and $R_9$ are independently selected from the group consisting of hydrogen, $(C_1-C_6)$ alkyl, $(C_3-C_{12})$ cycloalkyl, aryl and aryl$(C_1-C_6)$alkyl;

$R_4$ is 1 to 3 substituents independently selected from the group consisting of hydrogen, halo, $(C_1-C_6)$alkyl, $R_{13}$-aryl, $(C_3-C_{12})$cycloalkyl, $-CN$, $-CF_3$, $-OR_8$, $-(C_1-C_6)$alkyl-$OR_8$, $-OCF_3$, $-NR_8R_9$, $-(C_1-C_6)$alkyl-$NR_8R_9$, $-NHSO_2R_8$, $-SO_2N(R_{14})_2$, $-SO_2R_8$, $-SOR_8$, $-SR_8$, $-NO_2$, $-CONR_8R_9$, $-NR_9COR_8$, $-COR_8$, $-COCF_3$, $-OCOR_8$, $-OCO_2R_8$, $-COOR_8$, $-(C_1-C_6)$alkyl-NHCOOC$(CH_3)_3$, $-(C_1-C_6)$alkyl-NHCOCF$_3$, $-(C_1-C_6)$alkyl-NHSO$_2$—$(C_1-C_6)$alkyl, and $-(C_1-C_6)$alkyl-NHCONH—$(C_1-C_6)$-alkyl;

$R_{13}$ is 1–3 substituents independently selected from the group consisting of H, $(C_1-C_6)$alkyl, $(C_1-C_6)$alkoxy and halo;

$R_{14}$ is independently selected from the group consisting of H, $(C_1-C_6)$alkyl and $R_{13}$—$C_6H_4$—$CH_2$—;

provided that $ZR_1$ is not biphenylmethyl;

or a pharmaceutically acceptable salt thereof.

24. A pharmaceutical composition comprising a compound of claim 23 and at least one pharmaceutically acceptable excipient.

25. A method of treating pain comprising administering to a gatient in need thereof, an effective amount of an analgesic compound according to claim 23.

26. A compound of claim 1, wherein Z is a bond.

27. A compound of claim 26, wherein $R_1$ is cyclooctyl.

28. A compound of claim 1, wherein R is —$CH_2C$=$ONH_2$.

29. The compound 2-cyanoimino-3-acetomido-1-[1-(cyclooctyl)-4-piperidinyl]-1,3-dihydro-2H-benzimidazole or a pharmaceutically acceptable salt thereof.

30. A pharmaceutical composition comprising a compound of claim 29 and at least one pharmaceutically acceptable excipient.

31. A method of treating pain comprising administering to a patient in need thereof, an effective amount of an analgesic compound according to claim 29.